United States Patent [19]
Nohr et al.

[11] Patent Number: 5,782,963
[45] Date of Patent: Jul. 21, 1998

[54] COLORANT STABILIZERS

[75] Inventors: Ronald Sinclair Nohr, Alpharetta; John Gavin MacDonald, Decatur, both of Ga.

[73] Assignee: Kimberly-Clark Worldwide, Inc., Neenah, Wis.

[21] Appl. No.: 757,222

[22] Filed: Nov. 27, 1996

Related U.S. Application Data

[63] Continuation-in-part of Ser. No. 627,693, Mar. 29, 1996, abandoned.

[51] Int. Cl.⁶ .................................................. C09D 11/02
[52] U.S. Cl. .............................. 106/31.27; 106/31.43; 106/31.36; 106/31.49; 106/31.6; 106/31.68; 106/31.75; 106/31.78
[58] Field of Search ................... 106/31.49, 31.43, 106/31.27, 31.36, 31.78, 31.75, 31.6, 31.68

[56] References Cited

U.S. PATENT DOCUMENTS

| | | |
|---|---|---|
| 28,225 | 11/1860 | Heseltine et al. |
| 28,789 | 4/1860 | Chang . |
| 575,228 | 1/1897 | von Gallois . |
| 582,853 | 5/1897 | Feer . |
| 893,636 | 7/1908 | Maywald . |
| 1,013,544 | 1/1912 | Fuerth . |
| 1,325,971 | 12/1919 | Akashi . |
| 1,364,406 | 1/1921 | Olsen . |
| 1,436,856 | 11/1922 | Brenizer et al. |
| 1,744,149 | 1/1930 | Staehlin . |
| 1,803,906 | 5/1931 | Krieger et al. |
| 1,844,199 | 2/1932 | Bicknell et al. |
| 1,876,880 | 9/1932 | Drapal . |
| 1,880,572 | 10/1932 | Wendt et al. |
| 1,880,573 | 10/1932 | Wendt et al. |
| 1,916,350 | 7/1933 | Wendt et al. |
| 1,916,779 | 7/1933 | Wendt et al. |
| 1,955,898 | 4/1934 | Wendt et al. |
| 1,962,111 | 6/1934 | Bamberger . |
| 2,005,378 | 6/1935 | Kiel . |
| 2,005,511 | 6/1935 | Stoll et al. |
| 2,049,005 | 7/1936 | Gaspar . |
| 2,054,390 | 9/1936 | Rust et al. |
| 2,058,489 | 10/1936 | Murch et al. |
| 2,062,304 | 12/1936 | Gaspar . |
| 2,090,511 | 8/1937 | Crossley et al. |
| 2,097,119 | 10/1937 | Eggert . |
| 2,106,539 | 1/1938 | Schnitzspahn . |
| 2,111,692 | 3/1938 | Saunders et al. |
| 2,125,015 | 7/1938 | Gaspar . |
| 2,130,572 | 9/1938 | Wendt . |
| 2,132,154 | 10/1938 | Gaspar . |
| 2,145,960 | 2/1939 | Wheatley et al. |
| 2,154,996 | 4/1939 | Rawling . |
| 2,159,280 | 5/1939 | Mannes et al. |
| 2,171,976 | 9/1939 | Erickson . |
| 2,181,800 | 11/1939 | Crossley et al. |
| 2,185,153 | 12/1939 | Lecher et al. |
| 2,220,178 | 11/1940 | Schneider . |
| 2,230,590 | 2/1941 | Eggert et al. |
| 2,237,885 | 4/1941 | Markush et al. |
| 2,243,630 | 5/1941 | Houk et al. |
| 2,268,324 | 12/1941 | Polgar . |
| 2,281,895 | 5/1942 | van Poser et al. |
| 2,328,166 | 8/1943 | Poigar et al. |
| 2,346,090 | 4/1944 | Staehle . |
| 2,349,090 | 5/1944 | Haddock . |
| 2,356,618 | 8/1944 | Rossander et al. |
| 2,361,301 | 10/1944 | Libby, Jr. et al. |
| 2,364,359 | 12/1944 | Kienle et al. |
| 2,381,145 | 8/1945 | von Glahn et al. |
| 2,382,904 | 8/1945 | Federsen . |
| 2,386,646 | 10/1945 | Adams et al. |
| 2,402,106 | 6/1946 | von Glahn et al. |
| 2,416,145 | 2/1947 | Biro . |
| 2,477,165 | 7/1949 | Bergstrom . |
| 2,527,347 | 10/1950 | Bergstrom . |

(List continued on next page.)

FOREIGN PATENT DOCUMENTS

| | | |
|---|---|---|
| 103085 | 4/1937 | Australia . |
| 12624/88 | 9/1988 | Australia . |
| 620075 | 5/1962 | Belgium . |
| 637169 | 3/1964 | Belgium . |
| 413257 | 10/1932 | Canada . |
| 458808 | 12/1936 | Canada . |
| 460268 | 10/1949 | Canada . |
| 461082 | 11/1949 | Canada . |
| 463021 | 2/1950 | Canada . |
| 463022 | 2/1950 | Canada . |
| 465495 | 5/1950 | Canada . |
| 465496 | 5/1950 | Canada . |

(List continued on next page.)

OTHER PUBLICATIONS

Derwent World Patents Index, CS 120380(Kocourek, Jan), Oct. 15, 1966.
Derwent World Patents Index,JP 54117536(Kawashima F), Sep. 12, 1979.
Derwent World Patents Index, JP 5117105(Mitsui Toatsu Chem Inc.) May 14, 1993.
Derwent World Patents Index, SU 1219612(AS USSR Non-AQ Soln), Mar. 23, 1986.
Derwent World Patents Index, JP 61027288 (Sumitomo Chem Ind KK), Feb. 6, 1986.
Patent Abstracts of Japan, JP 03184896(Dainippon Printing Co Ltd.) Aug. 12, 1991.
Patent Abstracts of Japan, JPP 02141287(Dainippon Printing Co Ltd.) May 30, 1990.
Kubat et al. "Photophysical properties of metal complexes of meso–tetrakis (40sulphonatophenyl) porphyrin." *J. Photochem. and Photobiol.* 96 93–97 1996, no month.

(List continued on next page.)

*Primary Examiner*—Helene Klemanski
*Attorney, Agent, or Firm*—Jones & Askew, LLP

[57] ABSTRACT

The present invention comprises colorant stabilizers and a colorant composition which includes a colorant and a colorant stabilizer. The colorant stabilizer imparts light-stability to the colorant so that the colorant does not fade when exposed to electromagnetic radiation such as sunlight or artificial light.

36 Claims, No Drawings

U.S. PATENT DOCUMENTS

| | | |
|---|---|---|
| 2,580,461 | 1/1952 | Pearl . |
| 2,601,669 | 6/1952 | Tullsen . |
| 2,612,494 | 9/1952 | von Glahn et al. . |
| 2,612,495 | 9/1952 | von Glahn et al. . |
| 2,628,959 | 2/1953 | von Glahn et al. . |
| 2,647,080 | 7/1953 | Joyce . |
| 2,680,685 | 6/1954 | Ratchford . |
| 2,728,784 | 12/1955 | Tholstrup et al. . |
| 2,732,301 | 1/1956 | Robertson et al. . |
| 2,744,103 | 5/1956 | Koch . |
| 2,757,090 | 7/1956 | Meugebauer et al. . |
| 2,763,550 | 9/1956 | Lovick . |
| 2,768,171 | 10/1956 | Clarke et al. . |
| 2,773,056 | 12/1956 | Helfaer . |
| 2,798,000 | 7/1957 | Monterman . |
| 2,809,189 | 10/1957 | Stanley et al. . |
| 2,827,358 | 3/1958 | Kaplan et al. . |
| 2,834,773 | 5/1958 | Scalera et al. . |
| 2,875,045 | 2/1959 | Lurie . |
| 2,892,865 | 6/1959 | Giraldi et al. . |
| 2,897,187 | 7/1959 | Koch . |
| 2,936,241 | 5/1960 | Sharp et al. . |
| 2,940,853 | 6/1960 | Sagura et al. . |
| 2,955,067 | 10/1960 | McBurney et al. . |
| 2,992,129 | 7/1961 | Gauthier . |
| 2,992,198 | 7/1961 | Funahashi . |
| 3,030,208 | 4/1962 | Schellenberg et al. . |
| 3,071,815 | 1/1963 | MacKinnon . |
| 3,075,014 | 1/1963 | Palopoli et al. . |
| 3,076,813 | 2/1963 | Sharp . |
| 3,104,973 | 9/1963 | Sprague et al. . |
| 3,114,634 | 12/1963 | Brown et al. . |
| 3,121,632 | 2/1964 | Sprague et al. . |
| 3,123,647 | 3/1964 | Duennenberger et al. . |
| 3,133,049 | 5/1964 | Hertel et al. . |
| 3,140,949 | 7/1964 | Sprague et al. . |
| 3,154,416 | 10/1964 | Fidelman . |
| 3,155,509 | 11/1964 | Roscow . |
| 3,175,905 | 3/1965 | Wiesbaden . |
| 3,178,285 | 4/1965 | Anderau et al. . |
| 3,238,163 | 3/1966 | O'Neill . |
| 3,242,215 | 3/1966 | Heitmiller . |
| 3,248,337 | 4/1966 | Zirker et al. . |
| 3,266,973 | 8/1966 | Crowley . |
| 3,282,886 | 11/1966 | Gadecki . |
| 3,284,205 | 11/1966 | Sprague et al. . |
| 3,300,314 | 1/1967 | Rauner et al. . |
| 3,304,297 | 2/1967 | Wegmann et al. . |
| 3,305,361 | 2/1967 | Gaynor et al. . |
| 3,313,797 | 4/1967 | Kissa . |
| 3,330,659 | 7/1967 | Wainer . |
| 3,341,492 | 9/1967 | Champ et al. . |
| 3,359,109 | 12/1967 | Harder et al. . |
| 3,361,827 | 1/1968 | Biletch . |
| 3,363,969 | 1/1968 | Brooks . |
| 3,385,700 | 5/1968 | Willems et al. . |
| 3,397,984 | 8/1968 | Williams et al. . |
| 3,415,875 | 12/1968 | Luethi et al. . |
| 3,418,118 | 12/1968 | Thommes et al. . |
| 3,445,234 | 5/1969 | Cescon et al. . |
| 3,453,258 | 7/1969 | Parmerter et al. . |
| 3,453,259 | 7/1969 | Parmerter et al. . |
| 3,464,841 | 9/1969 | Skofronick . |
| 3,479,185 | 11/1969 | Chambers . |
| 3,502,476 | 3/1970 | Kohei et al. . |
| 3,503,744 | 3/1970 | Itano et al. . |
| 3,514,597 | 5/1970 | Haes et al. . |
| 3,541,142 | 11/1970 | Cragoe, Jr. . |
| 3,546,161 | 12/1970 | Wohlheim . |
| 3,547,646 | 12/1970 | Hori et al. . |
| 3,549,367 | 12/1970 | Chang et al. . |
| 3,553,710 | 1/1971 | Lloyd et al. . |
| 3,563,931 | 2/1971 | Horiguchi . |
| 3,565,753 | 2/1971 | Yurkowitz . |
| 3,574,624 | 4/1971 | Reynolds et al. . |
| 3,579,533 | 5/1971 | Yalman . |
| 3,595,655 | 7/1971 | Robinson et al. . |
| 3,595,657 | 7/1971 | Robinson et al. . |
| 3,595,658 | 7/1971 | Gerlach et al. . |
| 3,595,659 | 7/1971 | Gerlach et al. . |
| 3,607,639 | 9/1971 | Krefeld et al. . |
| 3,607,693 | 9/1971 | Heine et al. . |
| 3,607,863 | 9/1971 | Dosch . |
| 3,615,562 | 10/1971 | Harrison et al. . |
| 3,617,288 | 11/1971 | Hartman et al. . |
| 3,617,335 | 11/1971 | Kumura et al. . |
| 3,619,238 | 11/1971 | Kimura et al. . |
| 3,619,239 | 11/1971 | Osada et al. . |
| 3,637,337 | 1/1972 | Pilling . |
| 3,637,581 | 1/1972 | Horioguchi et al. . |
| 3,642,472 | 2/1972 | Mayo . |
| 3,647,467 | 3/1972 | Grubb . |
| 3,652,275 | 3/1972 | Baum et al. . |
| 3,660,542 | 5/1972 | Adachi et al. . |
| 3,667,954 | 6/1972 | Itano et al. . |
| 3,668,188 | 6/1972 | King et al. . |
| 3,669,925 | 6/1972 | King et al. . |
| 3,671,096 | 6/1972 | Mackin . |
| 3,671,251 | 6/1972 | Houle et al. . |
| 3,676,690 | 7/1972 | McMillin et al. . |
| 3,678,044 | 7/1972 | Adams . |
| 3,689,565 | 9/1972 | Hoffmann et al. . |
| 3,694,241 | 9/1972 | Guthrie et al. . |
| 3,695,879 | 10/1972 | Laming et al. . |
| 3,697,280 | 10/1972 | Strilko . |
| 3,705,043 | 12/1972 | Zablak . |
| 3,707,371 | 12/1972 | Files . |
| 3,729,313 | 4/1973 | Smith . |
| 3,737,628 | 6/1973 | Azure . |
| 3,765,896 | 10/1973 | Fox . |
| 3,775,130 | 11/1973 | Enomoto et al. . |
| 3,788,849 | 1/1974 | Taguchi et al. . |
| 3,799,773 | 3/1974 | Watari er al. . |
| 3,800,439 | 4/1974 | Sokolski et al. . |
| 3,801,329 | 4/1974 | Sandner et al. . |
| 3,817,752 | 6/1974 | Laridon et al. . |
| 3,840,338 | 10/1974 | Zviak et al. . |
| 3,844,790 | 10/1974 | Chang et al. . |
| 3,870,524 | 3/1975 | Watanabe et al. . |
| 3,873,500 | 3/1975 | Kato et al. . |
| 3,876,496 | 4/1975 | Lozano . |
| 3,887,450 | 6/1975 | Gilano et al. . |
| 3,895,949 | 7/1975 | Akamatsu . |
| 3,901,779 | 8/1975 | Mani . |
| 3,910,993 | 10/1975 | Avar et al. . |
| 3,914,165 | 10/1975 | Gaske . |
| 3,914,166 | 10/1975 | Rudolph et al. . |
| 3,915,824 | 10/1975 | McGinnis . |
| 3,919,323 | 11/1975 | Houlihan et al. . |
| 3,926,641 | 12/1975 | Rosen . |
| 3,928,264 | 12/1975 | Young, Jr. et al. . |
| 3,933,682 | 1/1976 | Bean . |
| 3,952,129 | 4/1976 | Matsukawa et al. . |
| 3,960,685 | 6/1976 | Sano et al. . |
| 3,965,157 | 6/1976 | Harrison . |
| 3,978,132 | 8/1976 | Houlihan et al. . |
| 3,984,248 | 10/1976 | Sturmer . |
| 3,988,154 | 10/1976 | Sturmer . |
| 4,004,998 | 1/1977 | Rosen . |
| 4,012,256 | 3/1977 | Levinos . |
| 4,017,652 | 4/1977 | Gruber . |
| 4,022,674 | 5/1977 | Rosen . |

| | | | | | | |
|---|---|---|---|---|---|---|
| 4,024,324 | 5/1977 | Sparks . | | 4,306,014 | 12/1981 | Kunikane et al. . |
| 4,039,332 | 8/1977 | Kokelenberg et al. . | | 4,307,182 | 12/1981 | Dalzell et al. . |
| 4,043,819 | 8/1977 | Baumann . | | 4,308,400 | 12/1981 | Felder et al. . |
| 4,048,034 | 9/1977 | Martan . | | 4,315,807 | 2/1982 | Felder et al. . |
| 4,054,719 | 10/1977 | Cordes, III . | | 4,318,705 | 3/1982 | Nowak et al. . |
| 4,056,665 | 11/1977 | Tayler et al. . | | 4,318,791 | 3/1982 | Felder et al. . |
| 4,058,400 | 11/1977 | Crivello . | | 4,321,118 | 3/1982 | Felder et al. . |
| 4,067,892 | 1/1978 | Thorne et al. . | | 4,335,054 | 6/1982 | Blaser et al. . |
| 4,071,424 | 1/1978 | Dart et al. . | | 4,335,055 | 6/1982 | Blaser et al. . |
| 4,073,968 | 2/1978 | Miyamoto et al. . | | 4,336,323 | 6/1982 | Winslow . |
| 4,077,769 | 3/1978 | Johnston . | | 4,343,891 | 8/1982 | Aasen et al. . |
| 4,079,183 | 3/1978 | Green . | | 4,345,011 | 8/1982 | Drexhage . |
| 4,090,877 | 5/1978 | Streeper . | | 4,347,111 | 8/1982 | Gehlhaus et al. . |
| 4,100,047 | 7/1978 | McCarty . | | 4,349,617 | 9/1982 | Kawashira et al. . |
| 4,105,572 | 8/1978 | Gorondy . | | 4,350,753 | 9/1982 | Shelnut et al. . |
| 4,107,733 | 8/1978 | Schickedanz . | | 4,351,893 | 9/1982 | Anderson . |
| 4,110,112 | 8/1978 | Roman et al. . | | 4,356,255 | 10/1982 | Tachikawa et al. . |
| 4,111,699 | 9/1978 | Krueger . | | 4,357,468 | 11/1982 | Szejtli et al. . |
| 4,114,028 | 9/1978 | Baio et al. . | | 4,359,524 | 11/1982 | Masuda et al. . |
| 4,126,412 | 11/1978 | Masson et al. . | | 4,362,806 | 12/1982 | Whitmore . |
| 4,141,807 | 2/1979 | Via . | | 4,367,072 | 1/1983 | Vogtle et al. . |
| 4,144,156 | 3/1979 | Kuesters et al. . | | 4,367,280 | 1/1983 | Kondo et al. . |
| 4,148,658 | 4/1979 | Kondoh et al. . | | 4,369,283 | 1/1983 | Altschuler . |
| 4,162,162 | 7/1979 | Dueber . | | 4,370,401 | 1/1983 | Winslow et al. . |
| 4,171,977 | 10/1979 | Hasegawa et al. . | | 4,372,582 | 2/1983 | Geisler . |
| 4,179,577 | 12/1979 | Green . | | 4,373,017 | 2/1983 | Masukawa et al. . |
| 4,181,807 | 1/1980 | Green . | | 4,373,020 | 2/1983 | Winslow . |
| 4,190,671 | 2/1980 | Vanstone et al. . | | 4,374,984 | 2/1983 | Eichler et al. . |
| 4,197,080 | 4/1980 | Mee . | | 4,376,887 | 3/1983 | Greenaway et al. . |
| 4,199,420 | 4/1980 | Photis . | | 4,383,835 | 5/1983 | Preuss et al. . |
| 4,229,172 | 10/1980 | Baumann et al. . | | 4,390,616 | 6/1983 | Sato et al. . |
| 4,232,106 | 11/1980 | Iwasaki et al. . | | 4,391,867 | 7/1983 | Derick et al. . |
| 4,238,492 | 12/1980 | Majoie . | | 4,399,209 | 8/1983 | Sanders et al. . |
| 4,239,843 | 12/1980 | Hara et al. . | | 4,400,173 | 8/1983 | Beaven . |
| 4,239,850 | 12/1980 | Kita et al. . | | 4,401,470 | 8/1983 | Bridger . |
| 4,241,155 | 12/1980 | Hara et al. . | | 4,416,961 | 11/1983 | Drexhage . |
| 4,242,430 | 12/1980 | Hara et al. . | | 4,421,559 | 12/1983 | Owatari . |
| 4,242,431 | 12/1980 | Hara et al. . | | 4,424,325 | 1/1984 | Tsunoda et al. . |
| 4,245,018 | 1/1981 | Hara et al. . | | 4,425,162 | 1/1984 | Sugiyama . |
| 4,245,995 | 1/1981 | Hugl et al. . | | 4,425,424 | 1/1984 | Atland et al. . |
| 4,246,330 | 1/1981 | Hara et al. . | | 4,426,153 | 1/1984 | Libby et al. . |
| 4,248,949 | 2/1981 | Hara et al. . | | 4,434,035 | 2/1984 | Eichler et al. . |
| 4,250,096 | 2/1981 | Kvita et al. . | | 4,447,521 | 5/1984 | Tiers et al. . |
| 4,251,622 | 2/1981 | Kimoto et al. . | | 4,450,227 | 5/1984 | Holmes et al. . |
| 4,254,195 | 3/1981 | Hara et al. . | | 4,460,676 | 7/1984 | Fabel . |
| 4,256,493 | 3/1981 | Yokoyama et al. . | | 4,467,112 | 8/1984 | Matsuura et al. . |
| 4,256,817 | 3/1981 | Hara et al. . | | 4,475,999 | 10/1984 | Via . |
| 4,258,123 | 3/1981 | Nagashima et al. . | | 4,477,681 | 10/1984 | Gehlhaus et al. . |
| 4,258,367 | 3/1981 | Mansukhani . | | 4,489,334 | 12/1984 | Owatari . |
| 4,259,432 | 3/1981 | Kondoh et al. . | | 4,495,041 | 1/1985 | Goldstein . |
| 4,262,936 | 4/1981 | Miyamoto . | | 4,496,447 | 1/1985 | Eichler et al. . |
| 4,268,605 | 5/1981 | Hara et al. . | | 4,500,355 | 2/1985 | Shimada et al. . |
| 4,268,667 | 5/1981 | Anderson . | | 4,508,570 | 4/1985 | Fugii et al. . |
| 4,269,926 | 5/1981 | Hara et al. . | | 4,510,392 | 4/1985 | Litt et al. . |
| 4,270,130 | 5/1981 | Houle et al. . | | 4,523,924 | 6/1985 | Lacroix . |
| 4,271,252 | 6/1981 | Hara et al. . | | 4,524,122 | 6/1985 | Weber et al. . |
| 4,271,253 | 6/1981 | Hara et al. . | | 4,534,838 | 8/1985 | Lin et al. . |
| 4,272,244 | 6/1981 | Schlick . | | 4,548,896 | 10/1985 | Sabongi et al. . |
| 4,276,211 | 6/1981 | Singer et al. . | | 4,555,474 | 11/1985 | Kawamura . |
| 4,277,497 | 7/1981 | Fromantin . | | 4,557,730 | 12/1985 | Bennett et al. . |
| 4,279,653 | 7/1981 | Makishima et al. . | | 4,565,769 | 1/1986 | Dueber et al. . |
| 4,279,982 | 7/1981 | Iwasaki et al. . | | 4,567,171 | 1/1986 | Mangum . |
| 4,279,985 | 7/1981 | Nonogaki et al. . | | 4,571,377 | 2/1986 | McGinniss et al. . |
| 4,284,485 | 8/1981 | Berner . | | 4,595,745 | 6/1986 | Nakano et al. . |
| 4,288,631 | 9/1981 | Ching . | | 4,604,344 | 8/1986 | Irving et al. . |
| 4,289,844 | 9/1981 | Specht et al. . | | 4,605,442 | 8/1986 | Kawashita et al. . |
| 4,290,870 | 9/1981 | Kondoh et al. . | | 4,613,334 | 9/1986 | Thomas et al. . |
| 4,293,458 | 10/1981 | Gruenberger et el. . | | 4,614,723 | 9/1986 | Schmidt et al. . |
| 4,298,679 | 11/1981 | Shinozaki et al. . | | 4,617,380 | 10/1986 | Hinson et al. . |
| 4,300,123 | 11/1981 | McMillin et al. . | | 4,620,875 | 11/1986 | Shimada et al. . |
| 4,301,223 | 11/1981 | Nakamura et al. . | | 4,620,876 | 11/1986 | Fugii et al. . |
| 4,302,606 | 11/1981 | Barabas et al. . | | 4,622,286 | 11/1986 | Sheets . |

| | | |
|---|---|---|
| 4,631,085 | 12/1986 | Kawanishi et al. . |
| 4,632,891 | 12/1986 | Banks et al. . |
| 4,632,895 | 12/1986 | Patel et al. . |
| 4,634,644 | 1/1987 | Irving et al. . |
| 4,638,340 | 1/1987 | Iiyama et al. . |
| 4,647,310 | 3/1987 | Shimada et al. . |
| 4,655,783 | 4/1987 | Reinert et al. . |
| 4,663,275 | 5/1987 | West et al. . |
| 4,663,641 | 5/1987 | Iiyama et al. . |
| 4,668,533 | 5/1987 | Miller . |
| 4,672,041 | 6/1987 | Jain . |
| 4,698,291 | 10/1987 | Koibuchi et al. . |
| 4,701,402 | 10/1987 | Patel et al. . |
| 4,702,996 | 10/1987 | Griffing et al. . |
| 4,704,133 | 11/1987 | Reinert et al. . |
| 4,707,161 | 11/1987 | Thomas et al. . |
| 4,707,425 | 11/1987 | Sasagawa et al. . |
| 4,707,430 | 11/1987 | Ozawa et al. . |
| 4,711,668 | 12/1987 | Shimada et al. . |
| 4,713,113 | 12/1987 | Shimada et al. . |
| 4,720,450 | 1/1988 | Ellis . |
| 4,721,531 | 1/1988 | Wildeman et al. . |
| 4,721,734 | 1/1988 | Gehlhaus et al. . |
| 4,724,021 | 2/1988 | Martin et al. . |
| 4,724,201 | 2/1988 | Okazaki et al . |
| 4,725,527 | 2/1988 | Robillard . |
| 4,727,824 | 3/1988 | Ducharme et al. . |
| 4,732,615 | 3/1988 | Kawashita et al. . |
| 4,737,190 | 4/1988 | Shimada et al. . |
| 4,737,438 | 4/1988 | Ito et al. . |
| 4,740,451 | 4/1988 | Kohara . |
| 4,745,042 | 5/1988 | Sasago et al. . |
| 4,746,735 | 5/1988 | Kruper, Jr. et al. . |
| 4,752,341 | 6/1988 | Rock . |
| 4,755,450 | 7/1988 | Sanders et al. . |
| 4,761,181 | 8/1988 | Suzuki . |
| 4,766,050 | 8/1988 | Jerry . |
| 4,766,055 | 8/1988 | Kawabata et al. . |
| 4,770,667 | 9/1988 | Evans et al. . |
| 4,771,802 | 9/1988 | Tannenbaum . |
| 4,772,291 | 9/1988 | Shibanai et al. . |
| 4,772,541 | 9/1988 | Gottschalk . |
| 4,775,386 | 10/1988 | Reinert et al. . |
| 4,786,586 | 11/1988 | Lee et al. . |
| 4,789,382 | 12/1988 | Neumann et al. . |
| 4,790,565 | 12/1988 | Steed . |
| 4,800,149 | 1/1989 | Gottschalk . |
| 4,803,008 | 2/1989 | Ciolino et al. . |
| 4,808,189 | 2/1989 | Oishi et al. . |
| 4,812,139 | 3/1989 | Brodmann . |
| 4,812,517 | 3/1989 | West . |
| 4,813,970 | 3/1989 | Kirjanov et al. . |
| 4,822,714 | 4/1989 | Sanders . |
| 4,831,068 | 5/1989 | Reinert et al. . |
| 4,834,771 | 5/1989 | Yamauchi et al. . |
| 4,837,106 | 6/1989 | Ishikawa et al. . |
| 4,837,331 | 6/1989 | Yamanishi et al. . |
| 4,838,938 | 6/1989 | Tomida et al. . |
| 4,839,269 | 6/1989 | Okazaki et al. . |
| 4,849,320 | 7/1989 | Irving et al. . |
| 4,853,037 | 8/1989 | Johnson et al. . |
| 4,853,398 | 8/1989 | Carr et al. . |
| 4,854,971 | 8/1989 | Gane et al. . |
| 4,857,438 | 8/1989 | Loerzer et al. . |
| 4,861,916 | 8/1989 | Kohler et al. . |
| 4,865,942 | 9/1989 | Gottschalk et al. . |
| 4,874,391 | 10/1989 | Reinert . |
| 4,874,899 | 10/1989 | Hoelderich et al. . |
| 4,885,395 | 12/1989 | Hoelderich . |
| 4,886,774 | 12/1989 | Doi . |
| 4,892,941 | 1/1990 | Dolphin et al. . |
| 4,895,880 | 1/1990 | Gottschalk . |
| 4,900,581 | 2/1990 | Stuke et al. . |
| 4,902,299 | 2/1990 | Anton . |
| 4,902,725 | 2/1990 | Moore . |
| 4,902,787 | 2/1990 | Freeman . |
| 4,911,732 | 3/1990 | Neumann et al. . |
| 4,911,899 | 3/1990 | Hagiwara et al. . |
| 4,917,956 | 4/1990 | Rohrbach . |
| 4,921,317 | 5/1990 | Suzuki et al. . |
| 4,925,770 | 5/1990 | Ichiura et al. . |
| 4,925,777 | 5/1990 | Inoue et al. . |
| 4,926,190 | 5/1990 | Lavar . |
| 4,933,265 | 6/1990 | Inoue et al. . |
| 4,933,948 | 6/1990 | Herkstroeter . |
| 4,937,161 | 6/1990 | Kita et al. . |
| 4,942,113 | 7/1990 | Trundle . |
| 4,950,304 | 8/1990 | Reinert et al. . |
| 4,952,478 | 8/1990 | Miyagawa et al. . |
| 4,952,680 | 8/1990 | Schmeidl . |
| 4,954,380 | 9/1990 | Kanome et al. . |
| 4,956,254 | 9/1990 | Washizu et al. . |
| 4,964,871 | 10/1990 | Reinert et al. . |
| 4,965,294 | 10/1990 | Ohngemach et al. . |
| 4,966,607 | 10/1990 | Shinoki et al. . |
| 4,966,833 | 10/1990 | Inoue . |
| 4,968,596 | 11/1990 | Inoue et al. . |
| 4,968,813 | 11/1990 | Rule et al. . |
| 4,985,345 | 1/1991 | Hayakawa et al. . |
| 4,987,056 | 1/1991 | Imahashi et al. . |
| 4,988,561 | 1/1991 | Wason . |
| 4,997,745 | 3/1991 | Kawamura et al. . |
| 5,001,330 | 3/1991 | Koch . |
| 5,002,853 | 3/1991 | Aoai et al. . |
| 5,002,993 | 3/1991 | West et al. . |
| 5,003,142 | 3/1991 | Fuller . |
| 5,006,758 | 4/1991 | Gellert et al. . |
| 5,013,959 | 5/1991 | Kogelschatz . |
| 5,017,195 | 5/1991 | Satou et al. . |
| 5,023,129 | 6/1991 | Morganti et al. . |
| 5,025,036 | 6/1991 | Carson et al. . |
| 5,026,425 | 6/1991 | Hindagolla et al. . |
| 5,026,427 | 6/1991 | Mitchell et al. . |
| 5,028,262 | 7/1991 | Barlow, Jr.et al. . |
| 5,028,792 | 7/1991 | Mullis . |
| 5,030,243 | 7/1991 | Reinert . |
| 5,030,248 | 7/1991 | Meszaros . |
| 5,034,526 | 7/1991 | Bonham et al. . |
| 5,037,726 | 8/1991 | Kojima et al. . |
| 5,045,435 | 9/1991 | Adams et al. . |
| 5,045,573 | 9/1991 | Kohler et al. . |
| 5,047,556 | 9/1991 | Kohler et al. . |
| 5,049,777 | 9/1991 | Mechtersheimer . |
| 5,053,320 | 10/1991 | Robbillard . |
| 5,055,579 | 10/1991 | Pawlowski et al. . |
| 5,057,562 | 10/1991 | Reinert . |
| 5,069,681 | 12/1991 | Bouwknegt et al. . |
| 5,070,001 | 12/1991 | Stahlhofen . |
| 5,073,448 | 12/1991 | Vieira et al. . |
| 5,074,885 | 12/1991 | Reinert . |
| 5,076,808 | 12/1991 | Hahn et al. . |
| 5,085,698 | 2/1992 | Ma et al. . |
| 5,087,550 | 2/1992 | Blum et al. . |
| 5,089,050 | 2/1992 | Vieira et al. . |
| 5,089,374 | 2/1992 | Saeva . |
| 5,096,456 | 3/1992 | Reinert et al. . |
| 5,096,489 | 3/1992 | Laver . |
| 5,096,781 | 3/1992 | Vieira et al. . |
| 5,098,477 | 3/1992 | Vieira et al. . |
| 5,098,793 | 3/1992 | Rohrbach et al. . |
| 5,098,806 | 3/1992 | Robillard . |
| 5,106,723 | 4/1992 | West et al. . |
| 5,108,505 | 4/1992 | Moffat . |
| 5,108,874 | 4/1992 | Griffing et al. . |

| | | |
|---|---|---|
| 5,110,706 | 5/1992 | Yumoto et al. . |
| 5,110,709 | 5/1992 | Aoai et al. . |
| 5,114,832 | 5/1992 | Zertani et al. . |
| 5,124,723 | 6/1992 | Laver . |
| 5,130,227 | 7/1992 | Wade et al. . |
| 5,133,803 | 7/1992 | Moffatt . |
| 5,135,940 | 8/1992 | Belander et al. . |
| 5,139,572 | 8/1992 | Kawashima . |
| 5,139,687 | 8/1992 | Borgher, Sr. et al. . |
| 5,141,556 | 8/1992 | Matrick . |
| 5,141,797 | 8/1992 | Wheeler . |
| 5,144,964 | 9/1992 | Demain . |
| 5,147,901 | 9/1992 | Rutsch et al. . |
| 5,153,104 | 10/1992 | Rossman et al. . |
| 5,153,105 | 10/1992 | Sher et al. . |
| 5,153,166 | 10/1992 | Jain et al. . |
| 5,160,346 | 11/1992 | Fuso et al. . |
| 5,160,372 | 11/1992 | Matrick . |
| 5,166,041 | 11/1992 | Murofushi et al. . |
| 5,169,436 | 12/1992 | Matrick . |
| 5,169,438 | 12/1992 | Matrick . |
| 5,173,112 | 12/1992 | Matrick et al. . |
| 5,176,984 | 1/1993 | Hipps, Sr. et al. . |
| 5,178,420 | 1/1993 | Shelby . |
| 5,180,425 | 1/1993 | Matrick et al. . |
| 5,180,652 | 1/1993 | Yamaguchi et al. . |
| 5,181,935 | 1/1993 | Reinert et al. . |
| 5,185,236 | 2/1993 | Shiba et al. . |
| 5,187,045 | 2/1993 | Bonham et al. . |
| 5,187,049 | 2/1993 | Sher et al. . |
| 5,190,565 | 3/1993 | Berenbaum et al. . |
| 5,190,710 | 3/1993 | Kletecka . |
| 5,190,845 | 3/1993 | Hashimoto et al. . |
| 5,193,854 | 3/1993 | Borowski, Jr. et al. . |
| 5,196,295 | 3/1993 | Davis . |
| 5,197,991 | 3/1993 | Rembold . |
| 5,198,330 | 3/1993 | Martic et al. . |
| 5,202,211 | 4/1993 | Vercoulen . |
| 5,202,212 | 4/1993 | Shin et al. . |
| 5,202,213 | 4/1993 | Nakahara et al. . |
| 5,202,215 | 4/1993 | Kanakura et al. . |
| 5,202,221 | 4/1993 | Imai et al. . |
| 5,256,193 | 10/1993 | Winnik et al. ............ 106/31.43 |
| 5,258,274 | 11/1993 | Helland et al. . |
| 5,261,953 | 11/1993 | Vieira et al. . |
| 5,262,276 | 11/1993 | Kawamura . |
| 5,268,027 | 12/1993 | Chan et al. . |
| 5,270,078 | 12/1993 | Walker et al. . |
| 5,271,764 | 12/1993 | Winnik et al. ............ 106/31.46 |
| 5,271,765 | 12/1993 | Ma . |
| 5,272,201 | 12/1993 | Ma et al. . |
| 5,275,646 | 1/1994 | Marshall et al. . |
| 5,279,652 | 1/1994 | Kaufmann et al. . |
| 5,282,894 | 2/1994 | Albert et al. . |
| 5,284,734 | 2/1994 | Blum et al. . |
| 5,286,286 | 2/1994 | Winnik et al. ............ 106/31.43 |
| 5,286,288 | 2/1994 | Tobias et al. . |
| 5,294,528 | 3/1994 | Furutachi . |
| 5,296,275 | 3/1994 | Goman et al. . |
| 5,296,556 | 3/1994 | Frihart . |
| 5,298,030 | 3/1994 | Burdeska et al. . |
| 5,300,403 | 4/1994 | Angelopolus et al. . |
| 5,300,654 | 4/1994 | Nakajima et al. . |
| 5,302,195 | 4/1994 | Helbrecht . |
| 5,302,197 | 4/1994 | Wickramanayke et al. . |
| 5,310,778 | 5/1994 | Shor et al. . |
| 5,312,713 | 5/1994 | Yokoyama et al. . |
| 5,312,721 | 5/1994 | Gesign . |
| 5,324,349 | 6/1994 | Sano et al. . |
| 5,328,504 | 7/1994 | Ohnishi . |
| 5,330,860 | 7/1994 | Grot et al. . |
| 5,334,455 | 8/1994 | Noren et al. . |
| 5,338,319 | 8/1994 | Kaschig et al. . |
| 5,340,631 | 8/1994 | Matsuzawa et al. . |
| 5,340,854 | 8/1994 | Martic et al. . |
| 5,344,483 | 9/1994 | Hinton . |
| 5,356,464 | 10/1994 | Hickman et al. . |
| 5,362,592 | 11/1994 | Murofushi et al. . |
| 5,368,689 | 11/1994 | Agnemo . |
| 5,372,387 | 12/1994 | Wajda . |
| 5,372,917 | 12/1994 | Tsuchida et al. . |
| 5,374,335 | 12/1994 | Lindgren et al. . |
| 5,376,503 | 12/1994 | Audett et al. . |
| 5,383,961 | 1/1995 | Bauer et al. . |
| 5,384,186 | 1/1995 | Trinh . |
| 5,393,580 | 2/1995 | Ma et al. . |
| 5,401,303 | 3/1995 | Stoffel et al. . |
| 5,401,562 | 3/1995 | Akao . |
| 5,415,686 | 5/1995 | Kurabayashi et al. . |
| 5,415,976 | 5/1995 | Ali . |
| 5,424,407 | 6/1995 | Tanaka et al. . |
| 5,425,978 | 6/1995 | Berneth et al. . |
| 5,426,164 | 6/1995 | Babb et al. . |
| 5,427,415 | 6/1995 | Chang . |
| 5,429,628 | 7/1995 | Trinh et al. . |
| 5,431,720 | 7/1995 | Nagai et al. . |
| 5,432,274 | 7/1995 | Luong et al. . |
| 5,445,651 | 8/1995 | Thoen et al. . |
| 5,445,842 | 8/1995 | Tanaka et al. . |
| 5,455,143 | 10/1995 | Zaki . |
| 5,459,014 | 10/1995 | Nishijima et al. . |
| 5,464,472 | 11/1995 | Horn et al. . |
| 5,466,283 | 11/1995 | Kondo et al. . |
| 5,474,691 | 12/1995 | Severns . |
| 5,475,080 | 12/1995 | Gruber et al. . |
| 5,476,540 | 12/1995 | Shields et al. . |
| 5,479,949 | 1/1996 | Battard et al. . |
| 5,489,503 | 2/1996 | Toan . |
| 5,498,345 | 3/1996 | Jollenbeck et al. . |
| 5,501,774 | 3/1996 | Burke . |
| 5,503,664 | 4/1996 | Sano et al. . |
| 5,509,957 | 4/1996 | Toan et al. . |
| 5,531,821 | 7/1996 | Wu ............................. 106/464 |
| 5,532,112 | 7/1996 | Kohler et al. . |
| 5,541,633 | 7/1996 | Winnik et al. ............ 106/31.43 |
| 5,543,459 | 8/1996 | Hartmann et al. ............ 525/54.3 |
| 5,571,313 | 11/1996 | Mafune et al. ............ 106/22 H |
| 5,575,891 | 11/1996 | Trokhan et al. ............ 102/111 |
| 5,580,369 | 12/1996 | Belding et al. ............ 96/125 |

FOREIGN PATENT DOCUMENTS

| | | |
|---|---|---|
| 465499 | 5/1950 | Canada . |
| 483214 | 5/1952 | Canada . |
| 517364 | 10/1955 | Canada . |
| 537687 | 3/1957 | Canada . |
| 552565 | 2/1958 | Canada . |
| 571792 | 3/1959 | Canada . |
| 779239 | 2/1968 | Canada . |
| 930103 | 7/1973 | Canada . |
| 2053094 | 4/1992 | Canada . |
| 94118 | 5/1958 | Czech Rep. . |
| 0003884 | 9/1979 | European Pat. Off. . |
| 0029284 | 5/1981 | European Pat. Off. . |
| 0127574 | 12/1984 | European Pat. Off. . |
| 0223587 | 5/1987 | European Pat. Off. . |
| 0262533 | 4/1988 | European Pat. Off. . |
| 0280458 | 8/1988 | European Pat. Off. . |
| 0308274 | 3/1989 | European Pat. Off. . |
| 0351615 | 1/1990 | European Pat. Off. . |
| 0371304 | 6/1990 | European Pat. Off. . |
| 0373662 | 6/1990 | European Pat. Off. . |
| 0375160 | 6/1990 | European Pat. Off. . |
| 0390439 | 10/1990 | European Pat. Off. . |
| 0458140A1 | 10/1991 | European Pat. Off. . |

| | | | | | | |
|---|---|---|---|---|---|---|
| 0458140 | 11/1991 | European Pat. Off. | | 61-128973 | 6/1986 | Japan . |
| 0468465 | 1/1992 | European Pat. Off. | | 61-97025 | 9/1986 | Japan . |
| 0542286 | 5/1993 | European Pat. Off. | | 61-222789 | 10/1986 | Japan . |
| 000571190 | 11/1993 | European Pat. Off. | | 61-247703 | 11/1986 | Japan . |
| 0608433 | 8/1994 | European Pat. Off. | | 62-285403 | 12/1986 | Japan . |
| 0609159 | 8/1994 | European Pat. Off. | | 62-7703 | 1/1987 | Japan . |
| 0639664 | 2/1995 | European Pat. Off. | | 62-97881 | 5/1987 | Japan . |
| 2245010 | 4/1975 | France . | | 62-100557 | 5/1987 | Japan . |
| 2383157 | 10/1978 | France . | | 62-127281 | 6/1987 | Japan . |
| 1047787 | 12/1957 | Germany . | | 63-43959 | 2/1988 | Japan . |
| 1022801 | 1/1958 | Germany . | | 63-48370 | 3/1988 | Japan . |
| 1039835 | 9/1958 | Germany . | | 63-95439 | 4/1988 | Japan . |
| 1040562 | 10/1958 | Germany . | | 63-95440 | 4/1988 | Japan . |
| 1045414 | 12/1958 | Germany . | | 63-95445 | 4/1988 | Japan . |
| 1047013 | 12/1958 | Germany . | | 63-95446 | 4/1988 | Japan . |
| 1132450 | 7/1962 | Germany . | | 63-95447 | 4/1988 | Japan . |
| 1132540 | 7/1962 | Germany . | | 63-95448 | 4/1988 | Japan . |
| 1154069 | 9/1963 | Germany . | | 63-95449 | 4/1988 | Japan . |
| 1240811 | 5/1967 | Germany . | | 63-95450 | 4/1988 | Japan . |
| 2202497 | 8/1972 | Germany . | | 63-151946 | 6/1988 | Japan . |
| 2432563 | 2/1975 | Germany . | | 63-164953 | 7/1988 | Japan . |
| 2437380 | 2/1975 | Germany . | | 63-165498 | 7/1988 | Japan . |
| 2444520 | 3/1975 | Germany . | | 63-223077 | 9/1988 | Japan . |
| 2416259 | 10/1975 | Germany . | | 63-223078 | 9/1988 | Japan . |
| 2714978 | 10/1977 | Germany . | | 63-243101 | 10/1988 | Japan . |
| 2722264 | 11/1978 | Germany . | | 63-199781 | 12/1988 | Japan . |
| 158237 | 1/1983 | Germany . | | 64-15049 | 1/1989 | Japan . |
| 3126433 | 1/1983 | Germany . | | 64-29337 | 1/1989 | Japan . |
| 3415033 | 10/1984 | Germany . | | 64-40948 | 2/1989 | Japan . |
| 3921600 | 1/1990 | Germany . | | 89014948 | 3/1989 | Japan . |
| 3833437 | 4/1990 | Germany . | | 1-128063 | 5/1989 | Japan . |
| 3833438 | 4/1990 | Germany . | | 1146974 | 6/1989 | Japan . |
| 004036328 | 7/1991 | Germany . | | 01210477 | 8/1989 | Japan . |
| 4132288 | 4/1992 | Germany . | | 1288854 | 11/1989 | Japan . |
| 4126461 | 2/1993 | Germany . | | 2-58573 | 2/1990 | Japan . |
| 662500 | 4/1964 | Italy . | | 292957 | 4/1990 | Japan . |
| 42-4756 | 1/1967 | Japan . | | 2179642 | 7/1990 | Japan . |
| 4315663 | 7/1968 | Japan . | | 2282261 | 11/1990 | Japan . |
| 4726653 | 7/1972 | Japan . | | 3-134072 | 6/1991 | Japan . |
| 4745409 | 11/1972 | Japan . | | 03163566 | 7/1991 | Japan . |
| 49-8909 | 2/1974 | Japan . | | 3-170415 | 7/1991 | Japan . |
| 50-65592 | 6/1975 | Japan . | | 3-206439 | 9/1991 | Japan . |
| 51-17802 | 2/1976 | Japan . | | 5134447 | 11/1991 | Japan . |
| 53-104321 | 9/1978 | Japan . | | 3-203694 | 12/1991 | Japan . |
| 55-62059 | 5/1980 | Japan . | | 3284668 | 12/1991 | Japan . |
| 55-90506 | 7/1980 | Japan . | | 4023884 | 1/1992 | Japan . |
| 0014233 | 2/1981 | Japan . | | 4023885 | 1/1992 | Japan . |
| 56-14569 | 2/1981 | Japan . | | 4-45174 | 2/1992 | Japan . |
| 56-24472 | 3/1981 | Japan . | | 4100801 | 4/1992 | Japan . |
| 56-36556 | 4/1981 | Japan . | | 4-136075 | 5/1992 | Japan . |
| 57-61055 | 4/1982 | Japan . | | 04356087 | 12/1992 | Japan . |
| 57-128283 | 8/1982 | Japan . | | 543806 | 2/1993 | Japan . |
| 57-171775 | 10/1982 | Japan . | | 561220 | 3/1993 | Japan . |
| 58-124452 | 7/1983 | Japan . | | 5080506 | 4/1993 | Japan . |
| 58-125770 | 7/1983 | Japan . | | 05119506 | 5/1993 | Japan . |
| 58-222164 | 12/1983 | Japan . | | 5-140498 | 6/1993 | Japan . |
| 59-89360 | 5/1984 | Japan . | | 2-219869 | 9/1993 | Japan . |
| 29219270 | 12/1984 | Japan . | | 5263067 | 10/1993 | Japan . |
| 59-219270 | 4/1985 | Japan . | | 68-0915 | 3/1994 | Japan . |
| 60-192729 | 10/1985 | Japan . | | 6116555 | 4/1994 | Japan . |
| 60-239739 | 11/1985 | Japan . | | 6116556 | 4/1994 | Japan . |
| 60-239740 | 11/1985 | Japan . | | 6116557 | 4/1994 | Japan . |
| 60-239741 | 11/1985 | Japan . | | 6-175584 | 6/1994 | Japan . |
| 60-239743 | 11/1985 | Japan . | | 6214339 | 8/1994 | Japan . |
| 61-14994 | 1/1986 | Japan . | | 6256494 | 9/1994 | Japan . |
| 61-14995 | 1/1986 | Japan . | | 6256633 | 9/1994 | Japan . |
| 61-21184 | 1/1986 | Japan . | | 7113828 | 4/1972 | Netherlands . |
| 61-288 | 1/1986 | Japan . | | 603767 | 8/1978 | Switzerland . |
| 61-3781 | 1/1986 | Japan . | | 197808 | 5/1988 | Switzerland . |
| 61-25885 | 2/1986 | Japan . | | 1310767 | 5/1987 | U.S.S.R. . |
| 61-30592 | 2/1986 | Japan . | | 1772118 | 10/1992 | U.S.S.R. . |
| 61-40366 | 2/1986 | Japan . | | 275245 | 10/1928 | United Kingdom . |

| | | |
|---|---|---|
| 349339 | 5/1931 | United Kingdom . |
| 355686 | 8/1931 | United Kingdom . |
| 399753 | 10/1933 | United Kingdom . |
| 441085 | 1/1936 | United Kingdom . |
| 463515 | 4/1937 | United Kingdom . |
| 492711 | 9/1938 | United Kingdom . |
| 518612 | 3/1940 | United Kingdom . |
| 539912 | 9/1941 | United Kingdom . |
| 626727 | 7/1947 | United Kingdom . |
| 600451 | 4/1948 | United Kingdom . |
| 616362 | 1/1949 | United Kingdom . |
| 618616 | 2/1949 | United Kingdom . |
| 779389 | 7/1957 | United Kingdom . |
| 1372884 | 11/1974 | United Kingdom . |
| 2146357 | 4/1985 | United Kingdom . |
| 92/11295 | 7/1992 | WIPO . |
| 93/06597 | 4/1993 | WIPO . |
| 94/01503 | 1/1994 | WIPO . |
| 94/22500 | 10/1994 | WIPO . |
| 94/22501 | 10/1994 | WIPO . |
| 95/04955 | 2/1995 | WIPO . |
| 96/00740 | 1/1996 | WIPO . |
| 96/19502 | 6/1996 | WIPO . |
| 96/22335 | 7/1996 | WIPO . |

OTHER PUBLICATIONS

Abstract for WO 95/00343 –A1 *Textiles: Paper: Cellulose* p. 7 1995, no month.

Maki, Y. et al. "A novel heterocyclic N–oxide, pyrimido[5, 4–g]pteridinetetrone 5–oxide, with multifunctional photooxidative properties" *Chemical Abstracts* 122 925 [no 122:31350 F] 1995, no month.

Abstract of patent , JP 6–80915 (Canon Inc.), Mar. 22, 1994.

Abstract of patent, JP 06–43573 (Iku Meji) (Feb. 18, 1994).

Pitchumani, K. et al. "Modification of chemical reactivity upon cyclodextrin encapsulation" *Chemical Abstracts* 121 982 [no. 121:13362 4v] 1994, no month.

Derwent Publications Ltd., London, 1993 JP 05297627 (Fujitsu Ltd.), Nov. 12, 1993. (Abstract).

Patent Abstract of Japan, JP 5241369 (Bando Chem Ind Ltd et al.), Sep. 21, 1993. (Abstract).

Derwent Publications Ltd., London, JP 05232738 (Yamazaki, T.), Sep. 10, 1993 (Abstract).

Derwent Publications Ltd., London, EP 000559310 (Zeneca Ltd.), Sep. 8, 1993.

Derwent Publications Ltd., London, J.A, 5–230410 (Seiko Epson Corp), Sep. 7, 1993.

Derwent Publications Ltd., London, JP 5–230407 (Mitsubishi Kasei Corp), Sep. 7, 1993. (Abstract).

Abstracts Of Patent, JP 405230410 (Seiko Epson Corp.), Sep. 7, 1993. (Abstract).

Abstracts Of Patent, JP 405230407 (Mitsubishi Kasei Corp.), Sep. 7, 1993. (Abstract).

Patent Abstracts of Japan, JP 5197198 (Bando Chem Ind Ltd et al.), Aug. 6, 1993. (Abstract).

Database WPI–Derwent Publications Ltd., London, J.A. 5197069 (Bando Chem), Aug. 6, 1993. (Abstract).

Abstract of patent, JP 5–195450 (Nitto Boseki Co. Ltd), Aug. 3, 1993.

Patent Abstracts of Japan, JP5181308 (Bando Chem Ind Ltd et al.), Jul. 23, 1993. (Abstract).

Patent Abstracts of Japan, JP 5181310 (Bando Chem Ind Ltd et al.), Jul. 23, 1993. (Abstract).

Derwent Publications Ltd., London, JP 5–132638 (Mitsubishi Kasei Corp), May 28, 1993. (Abstract).

Abstract Of Patent, JP 405132638 (Mitsubishi Kasei Corp.), May 28, 1993. (Abstract).

Derwent Publications Ltd., London, JP 5–125318 (Mitsubishi Kasei Corp), May 21, 1993. (Abstract).

Abstract Of Patent, JP 405125318 (Mitsubishi Kasei Corp.), May 21, 1993. (Abstract).

Abstract of patent, JP 05–117200 (Hidefumi Hirai et al.) (May 14, 1993).

Derwent Publications Ltd., London, JP 05061246 (Ricoh KK), Mar. 12, 1993. (Abstract).

Husain, N. et al. "Cyclodextrins as mobile–phase additives in reversed–phase HPLC"*American Laboratory* 82 80–87 1993, no month.

Hamilton D.P. "Tired of Shredding? New Ricoh Method Tries Different Tack" *Wall Street Journal* B2 1993, no month.

"Cyclodextrins: A Breakthrough for Molecular Encapsulation" *American Maize Products Co.(AMAIZO)* 1993, no month.

Duxbury "The Photochemistry and Photophysics of Triphenylmethane Dyes in Solid Liquid Media" *Chemical Review* 93 381–433 1993, no month.

Abstract of patent, JP 04–351603 (Dec. 7, 1992).

Abstract of patent, JP 04–351602 1992, no month.

Derwent Publications Ltd., London, JP 404314769 (Citizen Watch Co. Ltd.), Nov. 5, 1992. (Abstract).

Abstract of patent, JP 04315739 1992, no month.

Derwent Publications Ltd., London, JP 04300395 (Funai Denki KK), Oct. 23, 1992. (Abstract).

Derwent Publications Ltd., London, JP 404213374 (Mitsubishi Kasei Corp), Aug. 4, 1992 (Abstract).

Abstract of patent, JP 04–210228 1992, no month.

Abstract Of Patent, JP 404202571 (Canon Inc.), Jul. 23, 1992 (Abstract).

Abstract Of Patent, JP 404202271 (Mitsubishi Kasei Corp.), Jul. 23, 1992 (Abstract).

Derwent Publications Ltd., London, JP 4–189877 (Seiko Epson Corp), Jul. 8, 1992 (Abstract).

Derwent Publications Ltd., London, JP 404189876 (Seiko Epson Corp), Jul. 8, 1992. (Abstract).

Abstract Of Patent, JP 404189877 (Seiko Epson Corp.), Jul. 8, 1992. (Abstract).

Derwent Publications Ltd., London, J.A. 4–170479 (Seiko Epson Corp), Jun. 18, 1992. (Abstract).

Abstract of patent , JP 04–81402 1992, no month.

Abstract of patent , JP 04–81401 1992, no month.

Kogelschatz "Silent–discharge driven excimer UV sources and their applications" *Applied Surface Science* 410–423 1992, no month.

Derwent Publications, Ltd., London, JP 403269167 (Japan Wool Textile KK), Nov. 29, 1991 (Abstract).

Derwent Publications Ltd., London, Jo 3247676 (Canon KK), Nov. 5, 1991 (Abstract).

Abstract of patent, JP 03–220384 1991, no month.

Derwent Publications Ltd., London, JP 3167270 (Mitsubishi Kasei Corp), Jul. 19, 1991. (Abstract).

Derwent Publications Ltd., London, Jo 3167270 (Mitsubishi Kasei Corp.), Jul. 19, 1991 (Abstract).

Derwent Publications Ltd., London, Jo 3093780 (Dainippon Ink Chem KK.), Apr. 18, 1991 (Abstract).

Abstract of patent, JP 06369890 1991, no month.

Kogelschatz, U. et al. "New Excimer UV Sources for Industrial Applications" *ABB Review* 1–10 1991, no month.

Abstract of patent, JP 03–41165 1991, no month.

"Coloring/Decoloring Agent for Tonor Use Developed" *Japan Chemical Week* 1991, no month.

Braithwaite, M., "Formulation" *Chemistry & Technology of UV & EB Formulation for Coatings, Inks & Paints* IV 11–12 1991, no month.

*Scientific Polymer Products, Inc. Brochure* 24–31 1991, no month.

Dietliker, K. "Photoiniators for Free Radical and Cationinc Polymerisation" *Chem & Tech of UV & EB Formulation for Coatings Inks & Paints* III 280 1991, no month.

Dietliker, K. "Photoiniators for Free Radical and Cationinc Polymerisation" *Chem & Tech of UV & EB Formulation for Coatings, Inks & Paints* III 61, 63, 229–232, 405, 414, 1991, no month.

Esrom et al. "Large area Photochemical Dry Etching of Polymers with Incoherent Excimer UV Radiation" *MRS Materials Research Society* 1–7 1991, no month.

"New Excimer UV Sources for Industrial Applications" *ABB Review* 391 1–10 1991, no month.

Esrom et al. Excimer Laser–Induced Decomposition of Aluminum Nitride *Materials Research Society Fall Meeting* 1–6 1991, no month.

Esrom et al. "Metal deposition with a windowless VUV excimer source" *Applied Surface Science* 1–5 1991, no month.

Esrom "Excimer Laser–Induced Surface Activation of Aln for Electroless Metal Deposition" *Mat. Res. Sco.lSymp. Proc.* 204 457–465 1991, no month.

Zhang et al. "UV–induced decomposition of absorbed Cu–acetylacetonate films at room temperature for electroless metal plating" *Applied Surface Science* 1–6 1991, no month.

"German company develops reuseable paper" *Pulp & Paper* 1991, no month.

Abstract of patent, JP 02289652 1990, no month.

Ohashi et al. "Molecular Mechanics Studies on Inclusion Compounds of Cyanine Dye Monomers and Dimers in Cyclodextrin Cavities," *J. Am. Chem. Soc.* 112 5824–5830 1990, no month.

Kogelschatz et al. "New Incoherent Ultraviolet Excimer Sources for Photolytic Material Deposition," *Laser Und Optoelektronik* 1990, no month.

Abstract of Patent, JP 0297957, (Fuji Xerox Co., Ltd.) 1990, no month.

Derwent Publications Ltd., London, JP 2091166 (Canon KK), Mar. 30, 1990. (Abstract).

Esrom et al. "Metal Deposition with Incoherent Excimer Radiation" *Mat. Res. Soc. Symp. Proc.* 158 189–198 1990, no month.

Esrom "UV Excimer Laser–Induced Deposition of Palladium from palladiym Acetate Films" *Mat. Res. Soc. Symp. Proc.* 158 109–117 1990, no month.

Kogelschatz, U. "Silent Discharges for the Generation of ultraviolet and vacuum ultraviolet excimer radiation" *Pure & Applied Chem* 62 1667–74 1990, no month.

Esrom et al. "Investigation of the mechanism of the UV–induced palladium depostions processf from thin solid palladium acetate films" *Applied Surface Science* 46 158–162 1990, no month.

Zhang et al. "VUV synchrotron radiation processing of thin palladium acetate spin–on films for metallic surface patterning" *Applied Surface Science* 46 153–157 1990, no month.

Brennan et al. "Tereoelectronic effects in ring closure reactions: the 2'–hydroxychalcone –flavanone equilibrium, and related systems," *Canadian J. Chem.* 68 pp. 1780–1785 (10), no month.

Abstract of patent, JP 01–299083 1989, no month.

Derwent Publications Ltd., London, J.O. 1182379 (Canon KK), Jul. 20, 1989. (Abstract).

Derwent Publications Ltd., London, JP 1011171 (Mitsubishi Chem Ind. KK.), Jan. 13, 1989 (Abstract).

Gruber, R.J., et al. "Xerographic Materials" *Encyclopedia of Polymer Science and Engineering* 17 918–943 1989, no month.

Pappas, S.P. "Photocrosslinking" *Comph. Pol. Sci.* 6 135–148 1989, No Month.

Pappas, S.P. "Photoinitiated Polymerization" *Comph. Pol. Sci.* 4 337–355 1989, No Month.

Kirilenko, G.V. "An analog of the vesicular process with amplitude modulation of the incident light beam" *Chemical Abstracts* 111 569 [No. 111:12363 3b] 1989, No Month.

Esrom et al. "UV excimer laser–induced pre–nucleation of surfaces followed by electroless metallization" *Chemtronics* 4 216–223 1989, No Month.

Esrom et al. "VUV light–induced deposition of palladium using an incoherent Xe2* excimer source" *Chemtronics* 4 1989, No Month.

Esrom et al. "UV Light–Induced Deposition of Copper Films" C5–719–C5–725 1989, No Month.

Falbe et al. *Rompp Chemie Lexikon* 9 270 1989, No Month.

Derwent Publications, Ltd., London, SU 1423656 (Kherson Ind Inst), Sep. 15, 1988 (Abstract) 1988, No Month.

Derwent Publications, Ltd., London, EP 0280653 (Ciba Geigy AG), Aug. 31, 1988 (Abstract) 1988.

Abstract of patent, JP 63–190815 1988, No Month.

Furcone, S.Y. et al. "Spin–on B14Sr3Ca3Cu4O16+x superconducting thin films from citrate precursors," *Appl. Phys. Lett.* 52(2 2180–2182 5) 1988, No Month.

Abstract of patent, JP 63–144329 1988, No Month.

Abstract of patent, JP 63–130164 1988, No Month.

Derwent Publications, Ltd., London, J6 3112770 (Toray Ind Inc), May 17, 1988 (Abstract) 1988.

Derwent Publications, Ltd., London, J6 3108074 (Konishiroku Photo KK), May 12, 1988 (Abstract) 1988.

Derwent Publications, Ltd., London, J6 3108073 (Konishiroku Photo KK), May 12, 1988 (Abstract) 1988.

Abstract of patent, JP 61–77846 1988, No Month.

Abstract of patent, JP 63–73241 1988, No Month.

Abstract of patent, JP 6347762, 1988, No Month.

Abstract of patent, JP 63–47763, 1988, No Month.

Abstract of patent, JP 63–47764, 1988, No Month.

Abstract of patent, JP 63–47765, 1988, No Month.

Eliasson, B., et al. "UV Excimer Radiation from Dielectric–Barrier Discharges" *Applied Physics B* 46 299–303 1988, No Month.

Eliasson et al. "New Trends in High Intensity UV Generation" *EPA Newsletter* (32) 29–40 1988, No Month.

Cotton, F.A. "Oxygen: Group Via(16)" *Advanced Inorganic Chemistry* 5th ed. 473–474 1988, No Month.

Derwent Publications, Ltd., London, J6 2270665 (Konishiroku Photo KK), Nov. 25, 1987 (Abstract) 1987.

Abstract of patent, JP 62–215261 1987, No Month.

Database WPI, Derwent Publications Ltd., London, JP 62032082 (Mitsubishi Denki KK), Feb. 12, 1987. (Abstract) 1987.

Abstract of patent, JP 62–32082 1987, No Month.

Derwent Publications Ltd., London, J6 2007772 (Alps Electric KK), Jan. 14, 1987 (Abstract) 1987.

Gross et al. "Laser direct–wire metallization in thin palladium acetate films" *J. App. Phys.* 61 1628–1632 (4) 1987, No Month.

Al-Ismail et al. "Some experimental results on thin polypropylene films loaded with finely-dispersed copper" *Journal of Materials Science* 415–418 1987, No Month.

Baufay et al. "Optical self-regulation during laser-induced oxidation of copper" *J. Appl. Phys.* 61(9) 4640–4651 1987, No Month.

Al-Ismail et al. "Some experimental results on thin poly-propylene films loaded with finely-dispersed copper" *Journal of Materials Science* 415–418 1987, No Month.

Derwent Publications Ltd., London, JA 0284478 (Sanyo Chem Ind Ltd.), Dec. 15, 1986 (Abstract) 1986.

Abstract of patent, JP 61251842 1986, No Month.

Database WPI, Derwent Publications Ltd., London, GB; SU, A. 1098210 (Kutulya L A) 23 Jun. 1986.

Abstract of patent, JP 61-97025 1986, No Month.

Abstract of patent, JP 61-87760 1986, No Month.

Derwent Publications Ltd., London, DL 0234731 (Karl Marx Univ. Leipzig), Apr. 9, 1986 (Abstract).

Derwent Publications, Ltd., London, J6 1041381 (Osaka Prefecture), Feb. 27, 1986 (Abstract).

Sakai et al. "A Novel and Practical Synthetic Method of 3(2H)-Furanone Derivatives," *J. Heterocyclie Chem.* 23 pp. 1199–1201 1986, No Month.

Jellinek, H.H.G. et al. "Evolution of H2O and CO2 During the Copper-Catalyzed Oxidation of Isotactic Polypropylene," *J. Polymer Sci.* 24 389–403 1986, No Month.

Jellinek, H.H.G. et al. "Diffusion of Ca2+ Catalysts from Cu-Metal Polymer or Cu-Oxide/Polymer Interfaces into Isotactic Polypropylene," *J. Polymer Sci.* 24 503–510 1986, No Month.

Derwent Publications Ltd., London, J6 0226575 (Sumitomo Chem Ind Ltd.), Oct. 11, 1985 (Abstract).

Abstract of patent, JP 60-156761 1985, No Month.

Derwent Publications Ltd., London, J.A. 0011451 (Fugi Photo Film KK), Jan. 21, 1985. (Abstract).

Derwent Publications, Ltd., London J6 0011–449–A (Taoka Chemical KK) Jan. 21, 1985 (abstract).

Roos, G. et al. "Textile applications of photocrosslinkable polymers" *Chemical Abstracts* 103 57 [No. 103:23690j] 1985, No Month.

Derwent Publications, Ltd., London, JP 0198187 (Canon KK), Nov. 9, 1984. (Abstract).

Derwent Publications, Ltd., London, J.A. 0169883 (Ricoh KK), Sep. 25, 1984. (Abstract).

Derwent Publications, Ltd., London, JA 0169883 (Ricoh KK), Sep. 25, 1984 (Abstract).

Derwent Publications, Ltd., London, JA 0198187 (Canon KK), Sep. 11, 1984 (Abstract).

Derwent Publications, Ltd., London, J.A. 0053563 (Dainippon Toryo KK), Mar. 28, 1984. (Abstract).

Derwent Publications, Ltd., London, J.A. 0053562 (Dainippon Toryo KK), Mar. 28, 1984. (Abstract).

Derwent Publications, Ltd., London, J.A. 0053562 (Dainippon Toryo KK, Mar. 28, 1984. (Abstract).

Abstract of Patent, JA 0053563 (Dainippon Toryo KK), Mar. 28, 1984 (Abstract).

Abstract of Patent, JA 0053562 (Dainippon Toryo KK), Mar. 28, 1984 (Abstract).

Derwent Publications, Ltd., London, J.A. 0051961 (Dainippon Toryo KK), Mar. 26, 1984). (Abstract).

Abstract of Patent, JA 0051961 (Dainippon Toryo KK), Mar. 26, 1984 (Abstract).

Saenger, W. "Structural Aspects of Cyclodextrins and Their Inclusion Complexes" *Inculsion Compounds—Structural Aspects of Inclusion Compounds formed by Organic Host* 2 231–259 1984, No Month.

Szejtli "Industrial Applications of Cyclodextrins" *Inclusion Compounds: Physical Prop. & Applns* 3 331–390 1984, No Month.

Kano et al. "Three-Component Complexes of Cyclodextrins. Exciplex Formation in Cyclodextrin Cavity," *J. Inclusion Phenomena* 2 pp. 737–746 1984, No Month.

Suzuki et al. "Spectroscopic Investigation of Cyclodextrin Monomers, Derivatives, Polymers and Azo Dyes," *J. Inclusion Phenomena* 2, pp. 715–724 1984, No Month.

Abstract of Patent, JA 0222164 (Ricoh KK), Dec. 23, 1983 (Abstract).

Abstract of patent, JP 58211426 (Sekisui Plastics KK), (Dec. 8, 1983).

Derwent Publications, Ltd., London, EP 0072775 (Ciba Geigy AG), Feb. 23, 1983 (Abstract).

van Beek, H.C.A. "Light-Induced Colour Changes in Dyes and Materials" *Color Res. and Appl.* 8 176–181 1983, No Month.

Connors, K.A. "Application of a stoichiometric model of cyclodextrin complex formation" *Chemical Abstracts* 98 598 [No. 98:53067g] 1983, No Month.

Abstract of Patent, EP 0065617 (IBM Corp.), Dec. 1, 1982 (Abstract).

Derwent Publications, Ltd., London, J.A. 0187289 (Honshu Paper Mfg KK), Nov. 17, 1982. (Abstract).

Abstract of Patent, JA 0187289 (Honsho Paper Mfg KK), Nov. 17, 1982 (Abstract).

Abstract of Patent JA 0185364 (Ricoh KK), Nov. 15, 1982 (Abstract).

Derwent Publications, Ltd., London, J5 7139–146 (Showa Kako KK) Aug. 27, 1982 (Abstract).

Abstract of Patent, JA 0090069 (Canon KK), Jun. 4, 1982 (Abstract).

Derwent Publications, Ltd., London, JA 0061785 (Nippon Senka KK), Apr. 14, 1982 (Abstract).

Fischer, "Submicroscopic contact imaging with visible light by energy transfer" *Appl. Phys. Letter,* 40 (3 1982, No Month.

Abstract of Patent, JA 0010659 (Canon KK), Jan. 2, 1982 (Abstract).

Abstract of Patent, JA 0010661 (Canon KK), Jan. 2, 1982 (Abstract).

Christen "Carbonylverbindungen: Aldehyde und Ketone," *Grundlagen der Organischen Chemie* 255 1982, No Month.

Derwent Publications Ltd., London, J.A. 0155263 (Canon KK), Dec. 1, 1981, (Abstract).

Abstract of Patent, JA 0155263 (Canon KK), Dec. 1, 1981 (Abstract).

Abstract of Patent, JA 0147861 (Canon KK), Nov. 17, 1981 (Abstract).

Derwent Publications Ltd., London, J.A. 0143273 (Canon KK), Nov. 7, 1981, (Abstract).

Abstract of Patent, JA 0143272 (Canon KK), Nov. 7, 1981 (Abstract).

Abstract of Patent, JA 0136861 (Canon KK), Oct. 26, 1981 (Abstract).

Abstract of Patent, JA 6133378 (Canon KK), Oct. 19, 1981 (Abstract).

Abstract of Patent, JA 6133377 (Canon KK), Oct. 19, 1981 (Abstract).

Abstract of Patent, JA 6093775 (Canon KK), Jul. 29, 1981 (Abstract).

Derwent Publications Ltd., London, J.A. 0008135 (Ricoh KK), Jan. 27, 1981. (Abstract).

Derwent Publications Ltd., London, J.A. 0004488 (Canon KK), Jan. 17, 1981. (Abstract).

Abstract of Patent, JA 0004488 (Canon KK), Jan. 17, 1981 (Abstract).

Kirk–Othmer "Metallic Coatings," *Encyclopedia of Chemical Technology* 15 241–274 1981, No Month.

Komiyama et al. "One–Pot Preparation of 4–Hydroxychalcone β–Cyclodextrin as Catalyst," *Makromol. Chem.* 2 733–734 1981, No Month.

Derwent Publications, Ltd., London CA 1086–719 (Sherwood Medical) Sep. 30, 1980 (abstract).

Rosanske et al. "Stoichiometric Model of Cyclodextrin Complex Formation" *Journal of Pharmaceutical Sciences* 69 564–567 (5) 1980, No Month.

Semple et al. "Synthesis of Functionalized Tetrahydrofurans," *Tetrahedron Letters* 81 pp. 4561–4564 1980, No Month.

Kirk–Othmer "Film Deposition Techniques," *Encyclopedia of Chemical Technology* 10 247–283 1980, No Month.

Derwent World Patents Index, Derwent Info. Ltd., JP 54158941 (Toyo Pulp KK), Dec. 15, 1979. (Abstract).

Derwent Publications Ltd., London, J.A. 0005422 (Fuji Photo Film KK), Jan. 16, 1979. (Abstract).

Drexhage et al. "Photo–bleachable dyes and processes" *Research Disclosure* 85–87 1979, No Month.

"Color imaging devices and color filter arrays using photo–bleachable dyes" *Research Disclosure* 22–23 1979, No Month.

Wolff, N.E., et al. "Electrophotography" *Kirk–Othmer Encyclopedia of Chemical Technology* 8 794–826 1979, No Month.

Derwent Publications Ltd., London, J.A. 0012037 (Pentel KK), Jan. 29, 1977. (Abstract).

Abstract of Patent, JA 0012037 (Pentel KK), Jan. 29, 1977 (Abstract).

Jenkins, P.W. et al. "Photobleachable dye material" *Research Disclosure* 18 [No. 12932] 1975, No Month.

Lamberts, R.L. "Recording color grid patterns with lenticules" *Research Disclosure* 18–19 [No. 12923] 1975, No Month.

Karmanova, L.S. "Light stabilizers of daytime fluorescent paints" *Chemical Abstracts* 82 147 [No. 59971p] 1975, No Month.

Prokopovich, B. "Selection of effective photoinducers for rapid hardening of polyester varnish PE–250" *Chemical Abstracts* 83 131 [No. 81134a] 1975, No Month.

"Variable Contrast Printing System" *Research Disclosure* 19 [No. 12931] 1975.

Lakshman "Electronic Absorption Spectrum of Copper Formate Tetrahydrate" *Chemical Physics Letters* 31 331–334 (2) 1975, No Month.

Derwent Publications, Ltd., London J4 9131–226 (TNational Cash Register C) Dec. 16, 1974 (abstract).

Chang, I.F., et al. "Color Modulated Dye Ink Jet Printer" *IBM Technical Disclosure Bulletin* 17(5) 1520–1521 1974, No Month.

"Darocur 1173: Liquid Photoiniator for Ultraviolet Curing of Coatings" 1974.

Hosokawa et al. "Ascofuranone, an antibiotic from Ascochyta," Japan Kokai 73 91,278 (Nov. 28, 1973) *Merck Index* 80 p. 283; abstract 94259t 1974, No Month.

Abstract of patent, NL 7112489 (Dec. 27, 1971). No Month.

Gafney et al. "Photochemical Reactions of Copper (II)–1,3–Diketonate Complexes" *Journal of the Americqal Chemical Society* 1971, No Month.

Derwent Publications, Ltd., London SU 292698–S Jan. 15, 1971 (abstract).

Rigdon, J.E. "In Search of Paper that Spies Can't Copy" *Wall Street Journal*, No Date.

Chatterjee, S. et al. "Photochemistry of Carbocyanine Alkyltriphenylborate Salts: Intra–Ion–Pair Electron Transfer and the Chemistry of Boranyl Radicals" *J. Am. Chem. Soc.* 112 6329–6338, No Date.

"Assay—Physical and Chemical Analysis of Complexes" *Amaizo*, No Date.

"Cyclodextrin" *Amaizo*, No Date.

"Beta Cyclodextrin Polymer (BCDP)" *Amaizo*, No Date.

"Chemically Modified Cyclodextrins" *Amaizo*, No Date.

"Cyclodextrin Complexation" *American Maize Products Co.*, No Date.

"Monomers" *Scientific Polymer Products Inc.*, No Date.

Suppan, Paul "Quenching of Excited States" *Chemistry and Light* 65–69, No Date.

Yamaguchi, H. "Supersensitization. Aromatic ketones as supersensitizes" *Chemical Abstracts* 53 107 (d), No Date.

Stecher, H. "Ultraviolet–absorptive additives in adhesives, lacquers and plastics" *Chemical Abstracts* 53 14579 (c), No Date.

Maslennikov, A. S. "Coupling of diazonium salts with ketones" *Chemical Abstracts* 60 3128e, No Date.

Derwent Publications Ltd., London, 4 9128022, No Date.

Abstract of Patent, JP 405195450, No Date.

Rose, Philip I. "Gelatin," *Encyclopedia of Chemical Technology* 7 488–513, No Date.

COLORANT STABILIZERS

CROSS-REFERENCE TO RELATED PATENT APPLICATION

This patent application is a continuation-in-part patent application of U.S. patent application Ser. No. 08/627,693 filed on Mar. 29, 1996, now abandoned which is incorporated herein by reference.

TECHNICAL FIELD

The present invention relates to a family of colorant stabilizers. The colorant stabilizers, according to the present invention, are capable of stabilizing a colorant when it is exposed to electromagnetic radiation.

BACKGROUND OF THE INVENTION

A major problem with colorants is that they tend to fade when exposed to electromagnetic radiation such as sunlight or artificial light and the like. It is believed that most of the fading of colorants when exposed to light is due to photodegradation mechanisms. These degradation mechanisms include oxidation or reduction of the colorants depending upon the environmental conditions in which the colorant is placed. Fading of a colorant also depends upon the substrate upon which they reside.

Product analysis of stable photoproducts and intermediates has revealed several important modes of photodecomposition. These include electron ejection from the colorant, reaction with ground-state or excited singlet state oxygen, cleavage of the central carbon-phenyl ring bonds to form amino substituted benzophenones, such as triphenylmethane dyes, reduction to form the colorless leuco dyes and electron or hydrogen atom abstraction to form radical intermediates.

Various factors such as temperature, humidity, gaseous reactants, including $O_2$, $O_3$, $SO_2$, and $NO_2$, and water soluble, nonvolatile photodegradation products have been shown to influence fading of colorants. The factors that effect colorant fading appear to exhibit a certain amount of interdependence. It is due to this complex behavior that observations for the fading of a particular colorant on a particular substrate cannot be applied to colorants and substrates in general.

Under conditions of constant temperature it has been observed that an increase in the relative humidity of the atmosphere increases the fading of a colorant for a variety of colorant-substrate systems (e.g., McLaren, K., J. Soc. Dyers Colour, 1956, 72, 527). For example, as the relative humidity of the atmosphere increases, a fiber may swell because the moisture content of the fiber increases. This aids diffusion of gaseous reactants through the substrate structure.

The ability of a light source to cause photochemical change in a colorant is also dependent upon the spectral distribution of the light source, in particular the proportion of radiation of wavelengths most effective in causing a change in the colorant and the quantum yield of colorant degradation as a function of wavelength. On the basis of photochemical principles, it would be expected that light of higher energy (short wavelengths) would be more effective at causing fading than light of lower energy (long wavelengths). Studies have revealed that this is not always the case. Over 100 colorants of different classes were studied and found that generally the most unstable were faded more efficiently by visible light while those of higher lightfastness were degraded mainly by ultraviolet light (McLaren, K., J. Soc. Dyers Colour, 1956, 72, 86).

The influence of a substrate on colorant stability can be extremely important. Colorant fading may be retarded or promoted by some chemical group within the substrate. Such a group can be a ground-state species or an excited-state species. The porosity of the substrate is also an important factor in colorant stability. A high porosity can promote fading of a colorant by facilitating penetration of moisture and gaseous reactants into the substrate. A substrate may also act as a protective agent by screening the colorant from light of wavelengths capable of causing degradation.

The purity of the substrate is also an important consideration whenever the photochemistry of dyed technical polymers is considered. For example, technical-grade cotton, viscose rayon, polyethylene, polypropylene, and polyisoprene are known to contain carbonyl group impurities. These impurities absorb light of wavelengths greater than 300 nm, which are present in sunlight, and so, excitation of these impurities may lead to reactive species capable of causing colorant fading (van Beek, H. C. A., Col. Res. Appl., 1983, 8(3), 176).

Therefore, there exists a need for methods and compositions which are capable of stabilizing a wide variety of colorants from the effects of both sunlight and artificial light.

SUMMARY OF THE INVENTION

The present invention addresses the needs described above by providing compositions and methods for stabilizing colorants against radiation including radiation in the visible wavelength range.

The present invention also relates to colorant compositions having improved stability, wherein the colorant is associated with a colorant stabilizer. In one embodiment, the colorant stabilizer of the present invention is an aryliminealkene having the following general formula:

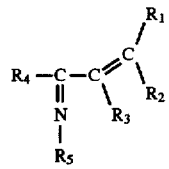

wherein $R_1$ is hydrogen, an alkyl, alkenyl, cycloalkyl, heterocycloalkyl, aryl, heteroaryl group, or substituted aryl group;

$R_2$ is hydrogen, an alkyl, alkenyl, cycloalkyl, heterocycloalkyl, aryl, heteroaryl group, or substituted aryl group;

$R_3$ is hydrogen, an alkyl, alkenyl, cycloalkyl, heterocycloalkyl, aryl, heteroaryl group, or substituted aryl group;

$R_4$ is hydrogen, an alkyl, alkenyl, cycloalkyl, heterocycloalkyl, aryl, heteroaryl, or substituted aryl group; and $R_5$ is an aryl, heteroaryl, polyalkene, or substituted aryl group;

wherein $R_1$, $R_2$, or $R_4$ is an aryl, heteroaryl, or substituted aryl group.

Desirably, the alkene group is in the trans configuration.

In another embodiment of the present invention, heavy atoms are added to conventional dyes to stabilize the dyes. These heavy atoms include Group VII ions including iodide ions. It has further been determined that the counterion is desirably a large ion with a relatively low charge density.

These counterions should be sodium or larger. The counterions also include relatively large organic counterions such as tetramethylammonium.

In yet another embodiment of the present invention, highly effective dye stabilizers include derivatives of phenols with the following general formula:

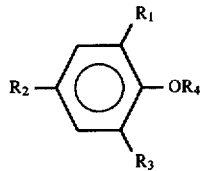

wherein $R_1$ is iodine, or an alkyl group having between 1 and 5 carbon atoms;

$R_2$ is an iodine, or an alkyl group having between 1 and 5 carbon atoms;

$R_3$ is iodine, or an alkyl group having between 1 and 5 carbon atoms; and $R_4$ is a sugar, polyhydroxy compound, sulfonic acid salt compound, carboxylic acid salt compound, polyether compound, or hydrogen, wherein the sugar includes, but is not limited to, glucose, fructose, polyether sugars, monosaccharides, polysaccharides, cyclodextrins, including but not limited to, α-cyclodextrin, β-cyclodextrin, γ-cyclodextrin, hydroxypropyl β-cyclodextrin, hydroxyethyl β-cyclodextrin, hydroxyethyl α cyclodextrin, carboxymethyl α cyclodextrin, carboxymethyl β cyclodextrin, carboxymethyl γ cyclodextrin, octyl succinated α cyclodextrin, octyl succinated β cyclodextrin, octyl succinated γ cyclodextrin and sulfated β cyclodextrin and sulfated γ-cyclodextrin. In particular, the triiodophenols and trimethylphenols and the water soluble derivatives thereof are particularly effective in stabilizing a wide variety of dyes.

In yet another embodiment, the colorant stabilizer of the present invention is a reducing agent. The reducing agent includes, but is not limited to, sodium thiosulfate ($Na_2S_2O_3$), sodium sulfite ($Na_2SO_3$), cysteine, sodium nitrite, sodium phosphite, and citric acid. A desired reducing agent is sodium thiosulfate. In this embodiment, the stabilizer may be admixed with the colorant, or it may be applied to a substrate to which the colorant will be applied. Although the reducing agent alone stabilizes a colorant, it is desirable that the reducing agent is combined with one or more of the above stabilizers.

In another embodiment, the colorant stabilizer of the present invention is a molecular includant having a chemical structure which defines at least one cavity. The molecular includant may be on or in a substrate to which the colorant will be applied, or it may be present in a colorant solution. The molecular includant may be, but is not limited to, clathrates, zeolites, crown ethers, calixarenes, valinomycin type natural antibiotics, various polyether compounds, nigericin type natural antibiotics, and cyclic compounds containing a plurality of pyranose rings. The cyclic compounds include, but are not limited to, cyclodextrins such as α-cyclodextrin, β-cyclodextrin, γ-cyclodextrin, δ-cyclodextrin, and derivatives thereof. A desired molecular includant is cyclodextrin. A more desired molecular includant is γ-cyclodextrin. Desirably, the molecular includant is present on or in the substrate to which the colorant will be applied.

The substrates to which the colorant stabilizers are applied include, but are not limited to, paper, wood, a wood product or composite, woven fabric, nonwoven fabric, textile, plastic, glass, metal, or any other substrate that would benefit from having a stabilized colorant thereon.

Although the molecular includant in or on the substrate stabilizes a colorant that is applied thereto, it is desirable that the colorant is combined with one or more of the above stabilizers. Additionally, in the embodiment where the molecular includant is present in a colorant solution, the colorant stabilizing molecules can be associated with one or more molecular includants. Additionally, the includants can have multiple colorant stabilizing molecules associated therewith. In some embodiments, the colorant is at least partially included within a cavity of the molecular includant and the colorant stabilizing molecules are associated with the molecular includant outside of the cavity. In some embodiments, the colorant stabilizing molecules are covalently coupled to the outside of the molecular includant.

In another embodiment, a colorant stabilizer, such as a molecular includant, is present in a polymer coating of a heat transfer product, such as is used for transferring graphic images onto clothing.

In another embodiment, a colorant stabilizer comprises one or more porphines that have an extremely short triplet state lifetime. (See e.g., Kubát, et al., Photophysical properties of metal complexes of meso-tetrakis (4-sulphonatophenyl) porphyrin, *J. Photochem. and Photbio. A: Chemistry* 96 (1996), pgs 93–97 which is incorporated herein by reference). An example of such a porphine is represented by Cu-meso-tetra-(4-sulfanatophenyl)-porphine (designated CuTPPS4) and Cu-meso-tetra-(N-methyl-4-pyridyl)-porphine, having the following structures:

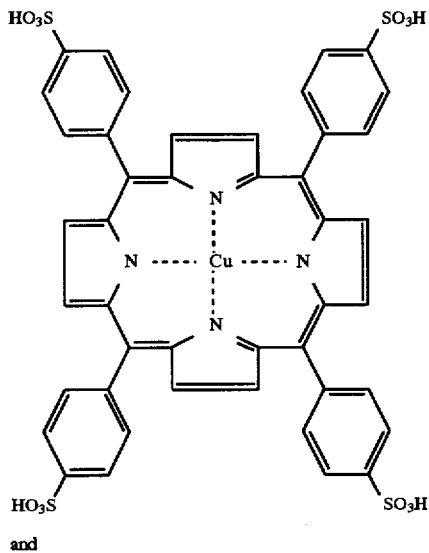

and

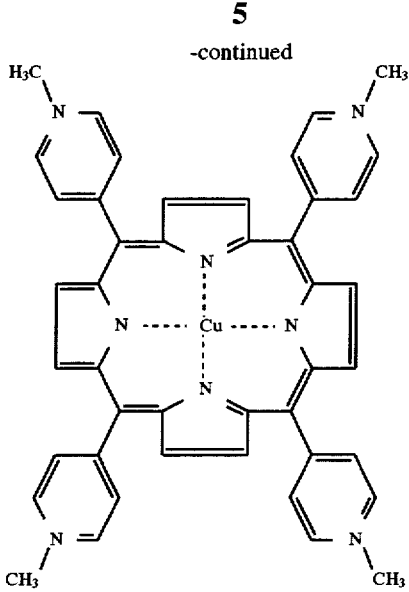

wherein the copper ion can also be substituted with a cobalt ion. Other metal ions, such as an iron ion, can be substituted in the porphine molecule as long as the molecule has a relatively short-lived triplet state.

The colorant stabilizing additive can also optionally be dimethyl amino benzoic acid quat (designated DMABAQ), represented by the following structure:

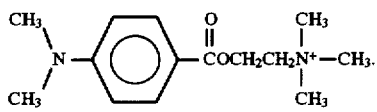

The colorant stabilizing additive can also optionally be a basic fuschin hydrazone, represented by the following structure:

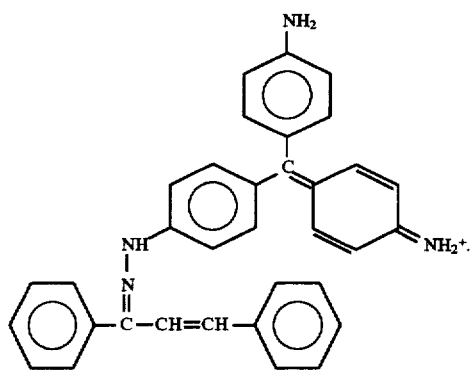

In addition, the colorant stabilizing additive of this invention is a benzophenone, of the general formula:

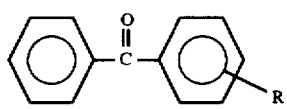

wherein R represents any substituents which permit the benzophenone to function as a colorant stabilizer.

Accordingly, each of these embodiments of the present invention provide stabilizing molecules that, when one or more of the stabilizing molecules are associated with a colorant, stabilizes the colorant. Therefore, the stabilizing molecules can be used as an additive to any colorant composition. For example, as certain of the stabilizing molecules are poorly soluble in water, they can be directly added to solvent or oil based (not water based) colorant compositions. Additionally, the stabilizing molecules can be added to other colorant compositions that contain additives enabling the solubilization of the stabilizing molecule therein. Further, the stabilizing molecules can be solubilized in an aqueous solution by attaching the molecule to a large water soluble molecule, such as a cyclodextrin.

The colorant stabilizers are particularly effective in ink jet inks. Use of the colorant stabilizers, as described herein, intensifies the colors and stabilizes the colors when exposed to light. Additionally, the colorant stabilizers are particularly effective in paper such as ink jet paper. Use of the colorant stabilizers in a substrate, as described herein, stabilizes a colorant to which it is applied. Also, colorant stabilizers in a substrate has been found to have the unexpected result of reducing the yellowing of the substrate itself upon exposure to light.

These and other features and advantages of the present invention will become apparent after a review of the following detailed description of the disclosed embodiments and the appended claims.

DETAILED DESCRIPTION OF THE INVENTION

This application is directed to compositions and methods for stabilizing colorants against radiation including radiation in the visible wavelength range. The compositions and methods relating to stabilizing a colorant by admixing a stabilizing molecule with a colorant solution will first be addressed below. Subsequently, the compositions and methods relating to stabilizing a colorant by applying the colorant to a treated substrate containing a stabilizing molecule will be discussed.

Admixing Stabilizing Molecules into Colorant Solutions

The present invention relates to colorant compositions having improved stability, wherein the colorant stabilizer is associated with a colorant solution. Desirably, the colorant stabilizer is admixed with a colorant solution. The colorant stabilizer is desirably an arylimineaIkene compound. Other desired colorant stabilizers are heavy atoms such as the iodide ion and phenol derivatives such as triiodophenol, trimethylphenol, and derivatives thereof. Additional colorant stabilizers include reducing agents such as sodium thiosulfate. Furthermore, colorant stabilizers include porphines, hydrazones, and benzophenones. The colorant stabilizers of the present invention are admixed with a colorant to stabilize the colorant when the admixture is exposed to electromagnetic radiation such as artificial light or sunlight.

The present invention further relates to a method of stabilizing a colorant comprising associating one or more of the colorant stabilizers with the colorant solution. Optionally, the colorant stabilizer may be associated with a molecular includant.

The present invention is particularly useful for stabilizing inks to be used in ink jet printers. Inks used in ink jet printers are described in U.S. patent application Ser. No. 08/461,365 filed on Jun. 5, 1995, which is incorporated herein by reference.

Thus, in one embodiment, the arylimineaIkene stabilizing composition is shown by the following general formula:

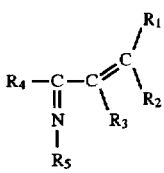

wherein $R_1$ is hydrogen, an alkyl, alkenyl, cycloalkyl, heterocycloalkyl, aryl, heteroaryl group, or substituted aryl group;

$R_2$ is hydrogen, an alkyl, alkenyl, cycloalkyl, heterocycloalkyl, aryl, heteroaryl group, or substituted aryl group;

$R_3$ is hydrogen, an alkyl, alkenyl, cycloalkyl, heterocycloalkyl, aryl, heteroaryl group, or substituted aryl group;

$R_4$ is hydrogen, an alkyl, alkenyl, cycloalkyl, heterocycloalkyl, aryl, heteroaryl, or substituted aryl group; and $R_5$ is an aryl, heteroaryl, or substituted aryl group;

wherein $R_1$, $R_2$, or $R_4$ is an aryl, heteroaryl, or substituted aryl group.

Desirably, the alkene group is in the trans configuration.

Desirably, the ariliminealkene stabilizing compound has one of the following formulae.

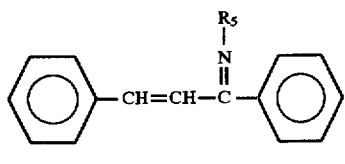

or

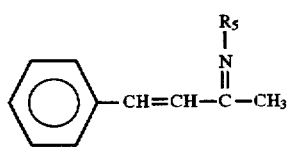

or

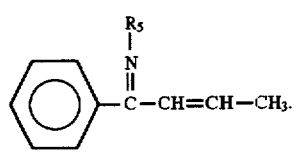

Accordingly, this embodiment of the present invention provides a stabilizing molecule, the above ariliminealkene, which when associated with a colorant, stabilizes the colorant. Therefore, the above ariliminealkene can be used as an additive to any colorant composition. For example, as certain of the ariliminealkene compounds are poorly water soluble, they can be directly added to solvent or oil based (not water based) colorant compositions. Additionally, the ariliminealkene compound can be added to other colorant compositions that contain additives enabling the solubilization of the compound therein. Further, the ariliminealkene stabilizing compounds can be solubilized in an aqueous solution by associating the compound with a large water soluble molecule, such as a cyclodextrin.

The term "composition" and such variations as "colored composition" are used herein to mean a colorant and one or more colorant stabilizers of the present invention. The composition can optionally include molecular includant.

As used herein, the term "colorant" is meant to include, without limitation, any material which typically will be an organic material, such as an organic colorant or dye. The term is meant to include a single material or a mixture of two or more materials.

The term "light-stable" is used herein to mean that the colorant, when associated with one of the colorant stabilizing molecules of the present invention, is more stable to electromagnetic radiation, including, but not limited to, sunlight or artificial light, than when the colorant is not associated with such a compound.

The term "molecular includant," as used herein, is intended to mean any substance having a chemical structure which defines at least one cavity. That is, the molecular includant is a cavity-containing structure. As used herein, the term "cavity" is meant to include any opening or space of a size sufficient to accept at least a portion of the colorant.

The term "functionalized molecular includant" is used herein to mean a molecular includant to which one or more molecules of a colorant stabilizer are covalently coupled to each molecule of the molecular includant. The term "degree of substitution" is used herein to refer to the number of these molecules or leaving groups (defined below) which are covalently coupled to each molecule of the molecular includant.

The term "derivatized molecular includant" is used herein to mean a molecular includant having more than two leaving groups covalently coupled to each molecule of molecular includant. The term "leaving group" is used herein to mean any leaving group capable of participating in a bimolecular nucleophilic substitution reaction. Examples of molecular includants include, but are not limited to, the cyclodextrins.

The term "artificial light" is used herein to mean light having a relatively broad bandwidth that is produced from conventional light sources, including, but not limited to, conventional incandescent light bulbs and fluorescent light bulbs.

The term "thereon" is used herein to mean thereon or therein. For example, the present invention includes a substrate having a colored composition thereon. According to the definition of "thereon" the colored composition may be present on the substrate or it may be in the substrate.

In several embodiments, the colorant stabilizer may be optionally associated with a molecular includant. It is to be noted that in all the compositions that contain a molecular includant, the number of such stabilizer molecules can be between approximately 1 and approximately 21 molecules per molecular includant. Of course, in certain situations, there can be more than 21 molecules per molecular includant molecule. Desirably, there are more than three of such stabilizer molecules per molecular includant.

The degree of substitution of the functionalized molecular includant may be in a range of from 1 to approximately 21. As another example, the degree of substitution may be in a range of from 3 to about 10. As a further example, the degree of substitution may be in a range of from about 4 to about 9.

In some embodiments of the present invention, the colorant is associated with the molecular includant. The term "associated" in its broadest sense means that the colorant is at least in close proximity to the molecular includant. For example, the colorant may be maintained in close proximity to the molecular includant by hydrogen bonding, van der Waals forces, or the like. Alternatively, the colorant may be covalently bonded to the molecular includant, although this normally is neither desired nor necessary. As a further example, the colorant may be at least partially included within the cavity of the molecular includant.

The dye or colorant, for example, may be an organic dye. Organic dye classes include, by way of illustration only, triarylmethyl dyes, such as Malachite Green Carbinol base {4-(dimethylamino)-α-[4-(dimethylamino)phenyl]-α-phenyl-benzene-methanol }, Malachite Green Carbinol hydrochloride {N-4-[[4-(dimethylamino)phenyl]phenyl-methylene]-2,5-cyclohexyldien-1-ylidene]-N-methyl-methanaminium chloride or bis[p-(dimethylamino)phenyl] phenylmethylium chloride }, and Malachite Green oxalate {N-4-[[4-(dimethylamino)-phenyl]-phenylmethylene]-2,5-cyclohexyldien-1-ylidene]-N-methyl-methanaminium chloride or bis[p-(dimethylamino)-phenyl]phenylmethylium oxalate}; monoazo dyes, such as Cyanine Black, Chrysoidine [Basic Orange 2; 4-(phenylazo)-1,3-benzenediamine monohydrochloride], Victoria Pure Blue BO, Victoria Pure Blue B, basic fuschin and β-Naphthol Orange; thiazine dyes, such as Methylene Green, zinc chloride double salt [3,7-bis (dimethylamino)-6-nitrophenothiazin-5-ium chloride, zinc chloride double salt]; oxazine dyes, such as Lumichrome (7,8-dimethylalloxazine); naphthalimide dyes, such as Lucifer Yellow CH {6-amino-2-[(hydrazino-carbonyl)amino]-2,3-dihydro-1,3-dioxo-1H-benz[de]iso-quinoline-5,8-disulfonic acid dilithium salt}; azine dyes, such as Janus Green B {3-(diethylamino)-7-[[4-(dimethylamino)phenyl] azo]-5-phenylphenazinium chloride}; cyanine dyes, such as Indocyanine Green {Cardio-Green or Fox Green; 2-[7-[1,3-dihydro-1,1-dimethyl-3-(4-sulfobutyl)-2H-benz[e]indol-2-ylidene]-1,3,5-heptatrienyl]-1,1-dimethyl-3-(4-sulfobutyl)-1H-benz[e]indolium hydroxide inner salt sodium salt}; indigo dyes, such as Indigo {Indigo Blue or Vat Blue 1; 2-(1,3-dihydro-3-oxo-2H-indol-2-ylidene)-1,2-dihydro-3H-indol-3-one}; coumarin dyes, such as 7-hydroxy-4-methylcoumarin (4-methylumbelliferone); benzimidazole dyes, such as Hoechst 33258 [bisbenzimide or 2-(4-hydroxyphenyl)-5-(4-methyl-1-piperazinyl)-2,5-bi-1H-benzimidazole trihydrochloride pentahydrate]; paraquinoidal dyes, such as Hematoxylin {Natural Black 1; 7,11b-dihydrobenz[b]-indeno[1,2-d]pyran-3,4,6a,9,10(6H)-pentol}; fluorescein dyes, such as Fluoresceinamine (5-aminofluorescein); diazonium salt dyes, such as Diazo Red RC (Azoic Diazo No. 10 or Fast Red RC salt; 2-methoxy-5-chlorobenzenediazonium chloride, zinc chloride double salt); azoic diazo dyes, such as Fast Blue BB salt (Azoic Diazo No. 20; 4-benzoylamino-2,5-diethoxybenzene diazonium chloride, zinc chloride double salt); phenylenediamine dyes, such as Disperse Yellow 9 [N-(2,4-dinitrophenyl)-1,4-phenylenediamine or Solvent Orange 53]; diazo dyes, such as Disperse Orange 13 [Solvent Orange 52; 1-phenylazo-4-(4-hydroxyphenylazo) naphthalene]; anthraquinone dyes, such as Disperse Blue 3 [Celliton Fast Blue FFR; 1-methylamino-4-(2-hydroxyethylamino)-9, 10-anthraquinone], Disperse Blue 14 [Celliton Fast Blue B; 1,4-bis(methylamino)-9,10-anthraquinone], and Alizarin Blue Black B (Mordant Black 13); trisazo dyes, such as Direct Blue 71 {Benzo Light Blue FFL or Sirius Light Blue BRR; 3-[(4-[(4-[(6-amino-1-hydroxy-3-sulfo-2-naphthalenyl)azo]-6-sulfo-1-naphthalenyl)-azo]-1-naphthalenyl)azo]-1,5-naphthalenedisulfonic acid tetrasodium salt}; xanthene dyes, such as 2,7-dichlorofluorescein; proflavine dyes, such as 3,6-diaminoacridine hemisulfate (Proflavine); sulfonaphthalein dyes, such as Cresol Red (o-cresolsulfonaphthalein); phthalocyanine dyes, such as Copper Phthalocyanine {Pigment Blue 15; (SP-4-1)-[29H,3 1H-phthalocyanato(2-)-$N^{29}$, $N^{30}$,$N^{31}$,$N^{32}$]copper}; carotenoid dyes, such as trans-β-carotene (Food Orange 5); carminic acid dyes, such as Carmine, the aluminum or calcium-aluminum lake of carminic acid (7-a-D-glucopyranosyl-9,10-dihydro-3,5,6,8-tetrahydroxy-1-methyl-9,10-dioxo-2-anthracenecarbonylic acid); azure dyes, such as Azure A [3-amino-7-(dimethylamino)phenothiazin-5-ium chloride or 7-(dimethylamino)-3-imino-3H-phenothiazine hydrochloride]; and acridine dyes, such as Acridine Orange [Basic Orange 14; 3,8-bis(dimethylamino)acridine hydrochloride, zinc chloride double salt] and Acriflavine (Acriflavine neutral; 3,6-diamino-10-methylacridinium chloride mixture with 3,6-acridinediamine).

In preparing the aryliminealkene colorant stabilizer of the present invention, one can, for example, start with a chalcone which is represented by the following formula:

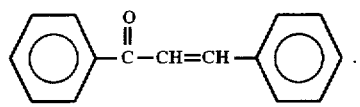

It is to be understood that the phenyl groups on the chalcone can be substituted with a wide variety of substituents. The chalcone is then reacted with a primary amine having the following general formula:

$NH_2$—R wherein R is an aryl, heteroaryl, or substituted aryl group. A desirable primary amine is 2 amino benzene sulfonic acid. The reaction is carried out in a nonaqueous solvent such as absolute alcohol. The resulting compound has the following general structure:

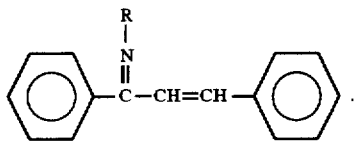

Accordingly, the colorant stabilizer of the present invention is an aryliminealkene having the following general formula:

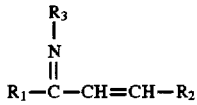

wherein if $R_1$ is an aryl group, then $R_2$ is a hydrogen; heterocyclic; alkyl; aryl, or a phenyl group, the phenyl group optionally being substituted with an alkyl, halo, amino, or a thiol group; and if $R_2$ is an aryl group, then $R_1$ is hydrogen; heterocyclic; alkyl; aryl, or a phenyl group, the phenyl group optionally being substituted with an alkyl, halo, amino, or a thiol group. $R_3$ is an aryl, heteroaryl, or substituted aryl group. Desirably, the alkene group is in the trans configuration.

Desirably, the aryliminealkene stabilizing compound has one of the following formulae:

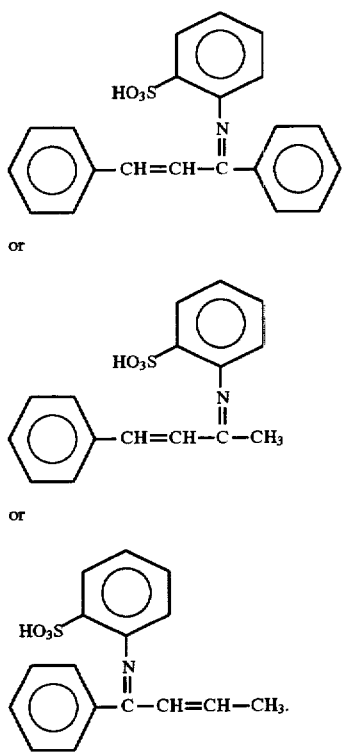

or

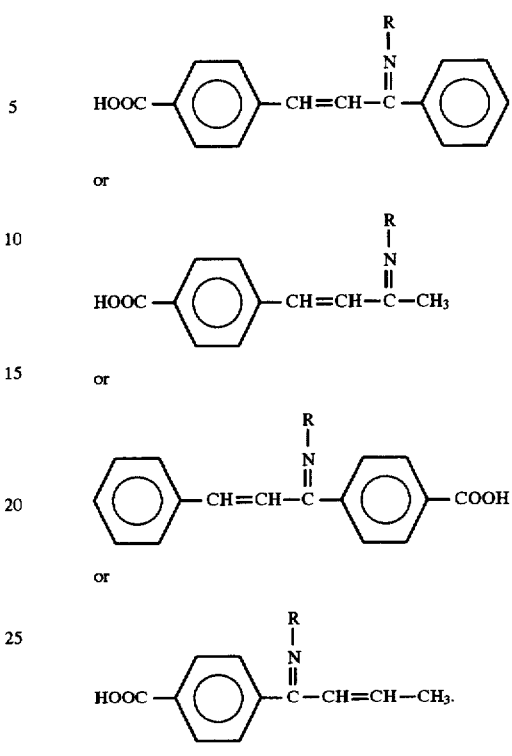

The SO₃H group can be in the ortho, meta or para position.

Yet another embodiment of the arylimineaIkene compound is an imine adduct of basic fuschin and is shown in the following formula:

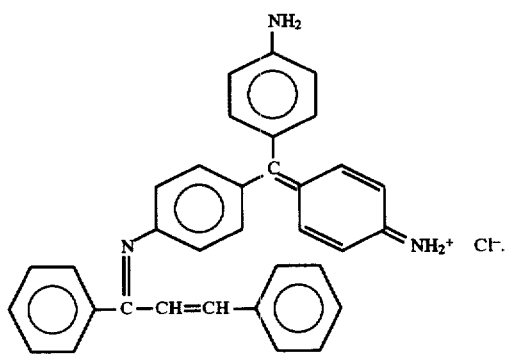

The imine adduct of basic fuschin can be synthesized according to Example 7 below.

In the embodiment where the arylimineaIkene compound is covalently attached to another molecule, whichever $R_1$ or $R_2$ that is an aryl group will have a group including, but not limited to, a carboxylic acid group, an aldehyde group, an amino group, a haloalkyl group, a hydroxyl group, or a thioalkyl group attached thereto to allow the arylimineaIkene to be covalently bonded to the other molecule. Accordingly, the arylimineaIkene stabilizing compound is represented by one of the following formulae:

wherein R is an aryl, heteroaryl, or substituted aryl group. Although it is preferred that the group attached to the aryl group is para to the remainder of the stabilizer molecule, the group may also be ortho or meta to the remainder of the molecule.

Accordingly, this embodiment of the present invention provides a stabilizing arylimineaIkene which, when associated with a colorant, stabilizes the colorant. Therefore, the above arylimineaIkenes can be used as an additive to any colorant composition. For example, if the arylimineaIkene compound is not water soluble or is poorly water soluble, it can be directly added to solvent or oil colorant compositions. Additionally, the arylimineaIkene compound can be added to other colorant compositions that contain additives enabling the solubilization of the compound therein.

This embodiment provides a method for stabilizing a colorant by admixing the arylimineaIkene compound with the colorants in an amount effective to stabilize the colorant. The arylimineaIkene desirably should be present in the colorant solution at a concentration of approximately 0.1 to 50% by weight, desirably between approximately 20% and 30% by weight. In other words, the arylimineaIkene should be equivalent in concentration to the colorant or should be at a higher concentration than the colorant. If no cyclodextrin or derivatized cyclodextrin is used, the desirable range is approximately 1 part dye to approximately 20 parts arylimineaIkene.

Although the arylimineaIkene compound need only be associated with the colorant, in some embodiments of the present invention, the arylimineaIkene compound may be covalently bonded to the colorant.

Another embodiment of the present invention is amino sulfonic acid represented by the following formula:

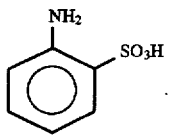

The SO₃H group can be in the ortho, meta or para position.

Another embodiment of colorant stabilizers include derivatives of phenols with the following general formula:

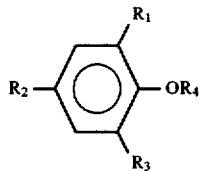

wherein $R_1$ is iodine, or an alkyl group having between 1 and 5 carbon atoms;

$R_2$ is an iodine, or an alkyl group having between 1 and 5 carbon atoms;

$R_3$ is iodine, or an alkyl group having between 1 and 5 carbon atoms; and $R_4$ is a hydrogen, sugar, polyhydroxy compound, sulfonic acid salt compound, carboxylic acid salt compound, polyether compound, or hydrogen, wherein the sugar includes, but is not limited to, glucose, fructose, polyether sugars, monosaccharides, polysaccharides, cyclodextrins, including but not limited to, α-cyclodextrin, β-cyclodextrin, γ-cyclodextrin, hydroxypropyl β-cyclodextrin, hydroxyethyl β-cyclodextrin, hydroxyethyl α cyclodextrin, carboxymethyl α cyclodextrin, carboxymethyl β cyclodextrin, carboxymethyl γ cyclodextrin, octyl succinated α cyclodextrin, octyl succinated β cyclodextrin, octyl succinated δ cyclodextrin and sulfated β cyclodextrin and sulfated γ-cyclodextrin.

The phenol derivatives are desirably added to the colorant solution at a concentration of between 0.5 and 10 molar equivalents to the concentration of the colorant.

A desired colorant stabilizer is triiodophenol (Aldrich). The triiodophenol has the following formula:

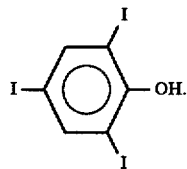

The triiodophenolates are desirably added to the colorant solution at a concentration of between 0.5 and 10 equivalents to the concentration of the colorant.

A desired colorant stabilizer includes trimethylphenol and derivatives thereof. The trimethylphenols have the following formula, wherein one or more of the methyl groups may be substituted with another alkyl or alkenyl group:

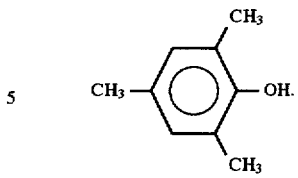

The trimethylphenols are desirably added to the colorant solution at a concentration of between 0.5 and 10 equivalents to the concentration of the colorant. Similarly, another desired colorant stabilizer is triiodophenol, which is desirably added to the colorant solution at a concentration of between 0.5 and 10 equivalents to the concentration of the colorant.

Further, the water solubility of the stabilizing compounds, including but not limited to the ariliminealkenes or triiodophenols or the trimethyphenols, can be increased by a variety of means. The desirable means of increasing the water solubility of the phenol-based stabilizing compounds is to add a water soluble moiety to the hydroxyl group on the phenol. In this embodiment, $R_4$ of the above phenol figure is a sugar, polyhydroxy compound, sulfonic acid salt compound, carboxylic acid salt compound, or polyether compound, wherein the sugar includes, but is not limited to, glucose, fructose, polyether sugars, monosaccharides, polysaccharides, cyclodextrins, including but not limited to, α-cyclodextrin, β-cyclodextrin, γ-cyclodextrin, hydroxypropyl β-cyclodextrin, hydroxyethyl β-cyclodextrin, hydroxyethyl α cyclodextrin, carboxymethyl α cyclodextrin, carboxymethyl β cyclodextrin, carboxymethyl γ cyclodextrin, octyl succinated α cyclodextrin, octyl succinated β cyclodextrin, octyl succinated γ cyclodextrin and sulfated β cyclodextrin and sulfated γ-cyclodextrin.

Accordingly, in one embodiment of the present invention the means of increasing the water solubility of the stabilizing compounds of the present invention is to react the phenol with a sugar, to produce the following representative compounds:

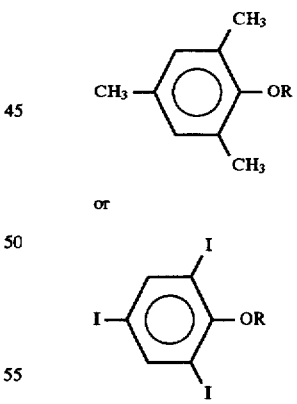

wherein R is any group capable of rendering the phenol more water soluble. More particularly, the R group may be, but is not limited to a sugar, polyhydroxy compound, sulfonic acid salt compound, carboxylic acid salt compound, or polyether compound, wherein the sugar includes, but is not limited to, glucose, fructose, polyether sugars, monosaccharides, polysaccharides, cyclodextrins, including but not limited to, α-cyclodextrin, β-cyclodextrin, γ-cyclodextrin, hydroxypropyl β-cyclodextrin, hydroxyethyl β-cyclodextrin, hydroxyethyl α cyclodextrin, carboxymethyl α cyclodextrin, carboxymethyl β cyclodextrin, carboxymethyl γ cyclodextrin, octyl succinated α cyclodextrin, octyl succinated β cyclodextrin, octyl succinated γ cyclodextrin and sulfated β cyclodextrin and sulfated γ-cyclodextrin. A desired R group is 1,2-o-isopropylidene-D-glucofuranose. The resultant desired stabilization compound is represented by one of the following formulae:

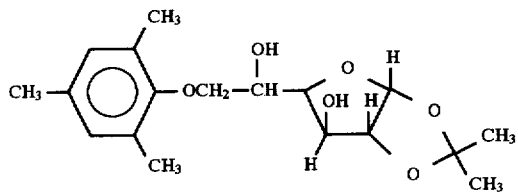

or

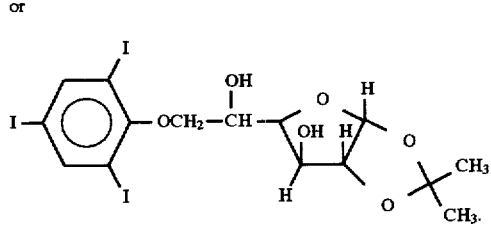

Examples 21, 22 and 24 describe how to prepare the above water soluble phenols. A more desired R group is glucose, where the ketal group of the above phenol-sugar compounds has been removed as described in Examples 23 and 25 producing the stabilizing compounds shown below:

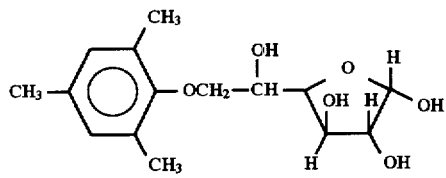

or

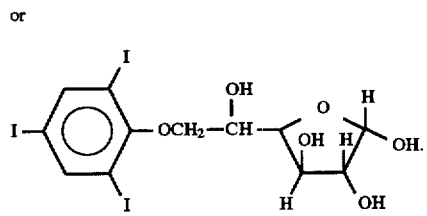

The colorant stabilizer compounds above in which the ketal group has been removed is a more desired stabilizer compound as it is more water soluble than if the ketal group is present.

Another desired colorant stabilizing compound is 3-(2,4,6-triiodophenoxy)-1,2-propanediol, as shown below:

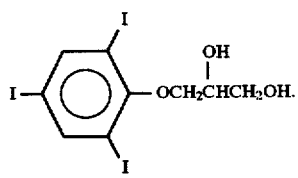

Another means of increasing the water solubility of the stabilizing compounds of the present invention is to associate the compound to a large water soluble molecule, such as a cyclodextrin or desirably a derivatized cyclodextrin. Desirably, the derivatized cyclodextrin is ethylhydroxy β-cyclodextrin. An example of such a covalent association of the stabilizing compounds is the triiodophenol or the trimethylphenol covalently bound with an ethylhydroxy β-cyclodextrin as represented in the following formulae:

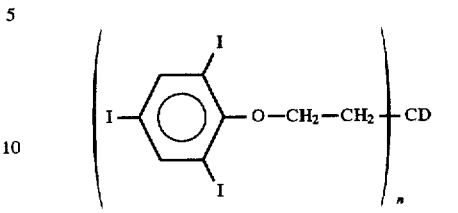

or

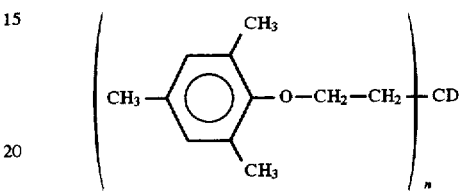

wherein n=1 to 21 and CD=cyclodextrin. The aryliminealkenes can be covalently attached to the β-cyclodextrin via any suitable functional group. An example of such an association is represented in the following formula:

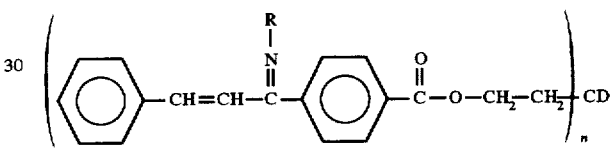

wherein R is an aryl, heteroaryl, or substituted aryl group, n=1 to 21 and β-cyclodextrin. It is to be understood that any of the aryliminealkenes can be covalently attached to the derivatized cyclodextrin through the appropriate functional groups. The water solubility of the triiodophenols or the trimethyphenols can be increased by adding a soluble compound to the molecule.

The association can be an admixture or can be a covalent attachment. Desirably, between about 1 and 12 stabilizing molecules can be attached to a cyclodextrin molecule. More desirably, between about 4 to about 9 stabilizing molecules are attached to a cyclodextrin molecule. Accordingly, the stabilizing compound attached to cyclodextrin can be added to any aqueous colorant system to stabilize the colorant therein. It is to be understood that the stabilizing aryliminealkenes do not have to be attached to the molecular includants to exhibit their stabilizing activity.

Although not wanting to be limited by the following, it is thought that the stabilizer compounds of the present invention exhibit excellent stabilizing properties as their high water solubility maintains the amount of additive present in solution over time, so that the additive continues to provide its stabilization properties to the admixture. A stabilizing additive precipitating out of a colorant composition negatively impacts the composition as less of the stabilizer remains in the solution, and therefore the colorant composition is less stabilized. Further, if the stabilizing additive is used in ink jet inks and cartridges, such precipitation can clog the ink jet printer and can other wise negatively impact the printing quality of the ink. A surprising and unexpected feature of the present invention is that the stabilizing compound is extremely water soluble, and does not precipitate out of ink solutions over time.

A third class of colorant stabilizers that are considered part of the present invention are heavy atoms such as iodide. These compounds are desirably associated with large counterions such as sodium or larger. It has been determined that smaller counterions, such as potassium, provide poor stabilization of the colorants. The desirable salt is sodium iodide. Another desirable salt is tetramethyl ammonium iodide. The preferred concentration of the heavy atoms is between approximately 0.5 to 5 mole equivalents. The iodide salt is added to the colorant before exposure to the electromagnetic radiation.

Examples 26 and 27 report the fade testing results of Hewlett Packard magenta ink admixed with various combinations of stabilizing compounds of the present invention. More particularly, 3 molar equivalents of the trimethylphenol sugar produced in Example 23, 4 molar equivalents of the triiodophenol sugar produced in Example 25, and two molar equivalents of sodium iodide were admixed with HP magenta ink having already admixed therein 2% by weight β-hydroxyethyl cyclodextrin. It is to be understood that the molar equivalents of the various stabilizing compounds can be varied. In comparison with the ink on the control sheets of paper and transparencies, the above described ink on paper and transparencies was much more stable. (See the tables in Example 26, and Example 27).

It is desirable that a colorant solution be stabilized with one or more of the following components in the following amounts: 2 to 10% wt/wt cyclodextrin or derivative thereof; 4–6% wt/wt of an arylimineallkene stabilizer of the present invention; 0.25 to 2 molar equivalents (eq) of an iodide; 2 to 7 eq of a triiodophenol sugar; 2 to 7 eq of a trialkyl phenol sugar; and 2 to 3 eq of ascorbic acid. More desirably, the colorant solution is to be stabilized with 2 to 10% wt/wt hydroxyethyl cyclodextrin; 4–6% wt/wt of an arylimineallkene stabilizer of the present invention; 0.25 to 2 molar equivalents (eq) of sodium iodide or tetramethyl amine iodide; 2 to 7 eq of a triiodophenol sugar; 2 to 7 eq of a trimethyl phenol sugar; and 2 to 3 eq of ascorbic acid. It is to be understood that units of "eq" or "molar equivalents" for stabilizing additives refers to molar equivalents of the stabilizing additives with respect to the dye. Additionally, it is to be understood that units of "wt/wt" for stabilizing additives refers to the weight of the additive with respect to the weight of the ink or colorant solution.

In another embodiment, a colorant solution is stabilized with the following: 4–10% fuschin imine adduct (Example 7); 0.25 to 2 eq of an iodide ion; and 2–10% β-cyclodextrin, desirably hydroxyethyl β-cyclodextrin.

In another embodiment described in Example 37, a colorant stabilizer, such as a molecular includant, is present in a polymer coating of a heat transfer product, such as is used for transferring graphic images onto clothing.

In another embodiment described in Example 38, a colorant stabilizer is represented by the porphines Cu-meso-tetra-(4-sulfanatophenyl)-porphine (designated CuTPPS4) and Cu-meso-tetra-(N-methyl-4-pyridyl)-porphine (designated CuTMPS4), having the following structure:

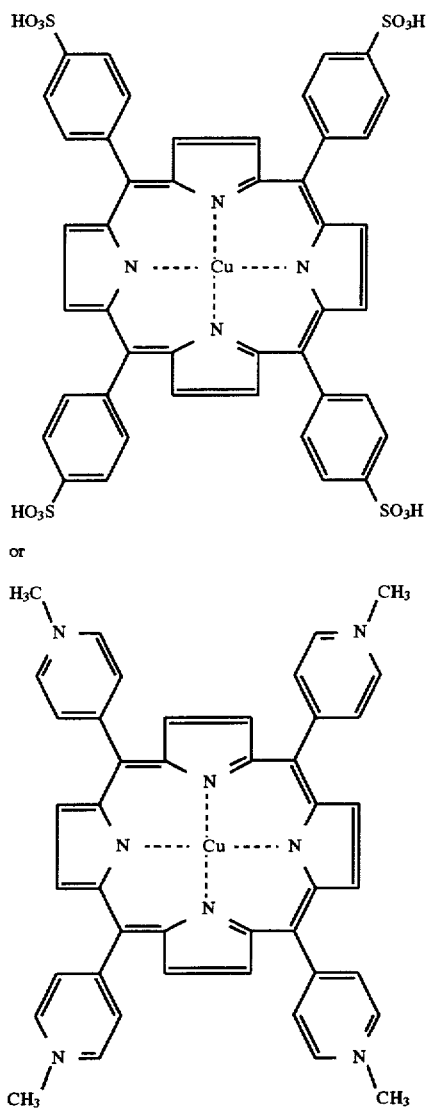

wherein the copper ion can also be substituted with a cobalt ion. It is also understood that in the case of CuTPPS4 or CoTPPS4, the sulfuric acid moieties may be substituted with salts when in solution, such as sodium salts. The colorant solution may be stabilized with about 0.1% to 10% wt/wt porphine, more preferably about 0.3% to 1% wt/wt porphine, and more preferably about 0.5% wt/wt porphine.

In another embodiment described in Example 38, the colorant stabilizing additive can also optionally be dimethyl amino benzoic acid quat (designated DMABAQ), represented by the following structure:

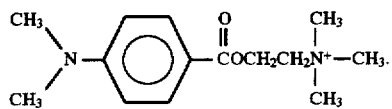

The colorant solution may be stabilized with about 0.1% to 15% wt/wt DMABAQ, more preferably about 0.5% to 10% wt/wt DMABAQ, and more preferably about 1% to 5% wt/wt DMABAQ.

In another embodiment described in Example 39, the colorant stabilizing additive can also optionally be a basic fuschin hydrazone, represented by the following structure:

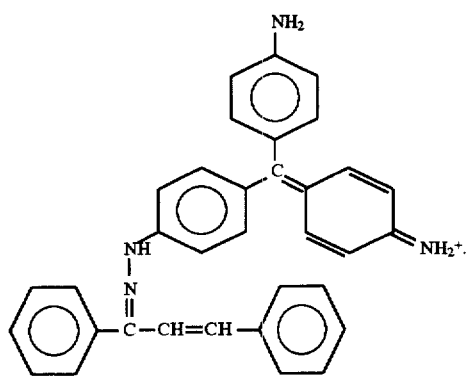

The colorant solution may be stabilized with about 0.1% to 15% wt/wt hydrazone, more preferably about 0.5% to 10% wt/wt hydrazone, and more preferably about 1% to 5% wt/wt hydrazone.

In addition, another embodiment of the colorant stabilizing additive of this invention as described in Example 40, is a benzophenone, of the general formula:

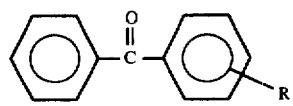

wherein R represents any substituents which permit the benzophenone to function as a colorant stabilizer. Suitable substituents include substituents which improve the solubility of the benzophenone in aqueous solutions and/or provide a high electron density next to the aromatic ring of the benzophenone. Suitable substituents include, but are not limited to, hydroxyl groups, alkyl ether groups, and sulfonic acid groups. The colorant solution may be stabilized with about 0.01% to 15% wt/wt benzophenone, more preferably about 0.3% to 5% wt/wt benzophenone, and more preferably about 0.5% to 1% wt/wt benzophenone.

Although not wanting to be limited by the following, it is theorized that the above stabilizing compounds of the present invention, either admixed with a colorant solution or on or in a substrate to which the colorant is applied, act by quenching the excited state of a dye molecule by efficiently returning it to a ground state. This reduces the likelihood of an oxidative or other chemical reaction occurring which would render the dye chromophore colorless.

The quenching process can occur by a number of processes. One such process is referred to as the heavy atom effect (internal or external) in which atoms with a high atomic number, such as iodine and xenon, can effect the excited electronic transitions of the dye molecule by allowing here to fore forbidden electronic transitions to occur and by decreasing the excited state lifetimes. This effect permits the rapid return of the dye to its ground state.

Another quenching process involves back electron transfer, in this case, quenching of the excited dye molecule occurs through sequential electron transfer. The additive or quencher, and dye form an ion pair through electron donation within which back electron transfer leads to an overall deactivation of the excited energy donor, i.e., the dye.

Another quenching process involves a condition in which the quencher (additive) molecule has an excited energy state lower than the excited dye. In this case, it may be possible to transfer the excited energy to the quencher thereby allowing the dye molecule to return to its ground state. These mechanisms are more fully discussed in Chemistry and Light, Suppan, P., Published by The Royal Society of Chemistry, 1994, pgs 65–69 which is incorporated herein by reference.

In all cases, it is optionally desirable to add a molecular includant to the colorant solution. The molecular includant can be inorganic or organic in nature. In certain embodiments, the chemical structure of the molecular includant is adapted to form a molecular inclusion complex. Examples of molecular includants are, by way of illustration only, clathrates or intercalates, zeolites, and cyclodextrins. Examples of cyclodextrins include, but are not limited to, α-cyclodextrin, β-cyclodextrin, γ-cyclodextrin, δ-cyclodextrin, hydroxypropyl β-cyclodextrin, hydroxyethyl β-cyclodextrin, hydroxyethyl α cyclodextrin, carboxymethyl α cyclodextrin, carboxymethyl β cyclodextrin, carboxymethyl γ cyclodextrin, octyl succinated α cyclodextrin, octyl succinated β cyclodextrin, octyl succinated γ cyclodextrin and sulfated β cyclodextrin and sulfated γ-cyclodextrin (American Maize-Products Company, Hammond, Ind.).

The term "derivatized cyclodextrin" as used herein means a cyclodextrin having more than two leaving groups covalently coupled to each molecule of cyclodextrin. The term "leaving group" is used herein to mean any leaving group capable of participating in a bimolecular nucleophilic substitution reaction. Examples of derivatized cyclodextrin includes, but is not limited to, hydroxypropyl β-cyclodextrin, hydroxyethyl β-cyclodextrin, hydroxyethyl α cyclodextrin, carboxymethyl α cyclodextrin, carboxymethyl β cyclodextrin, carboxymethyl γ cyclodextrin, octyl succinated α cyclodextrin, octyl succinated β cyclodextrin, octyl succinated γ cyclodextrin and sulfated β and γ-cyclodextrin. A desired derivatized cyclodextrin is ethyl-hydroxy β-cyclodextrin.

A desired molecular includant is γ-cyclodextrin. Another desirable molecular includant is β-cyclodextrin. In other embodiments, the molecular includant is an ethyl hydroxy β-cyclodextrin. Although not wanting to be bound by the following theory, it is believed that the molecular includant inhibits the aggregation of the colorant molecule in solution. Other aggregation inhibitors that can be used in practicing the present invention are starches, pectins, amyloses, clathrates and the crown ethers. It is to be understood that the addition of derivatized cyclodextrins to an ink formulation for the purpose of inhibiting aggregation and/or stabilizing the dyes in the inks is considered one aspect of the present invention.

In some embodiments, the colorant and the colorant stabilizers are associated with the molecular includant. The term "associated", in its broadest sense, means that the colorant and/or the colorant stabilizers are at least in close proximity to the molecular includant. For example, the colorant and/or the colorant stabilizers can be maintained in close proximity to the molecular includant by hydrogen bonding, van der Waals forces, ionic bonding, hydrogen bonding, dipole-dipole interactions or the like.

Alternatively, either or both of the colorant and the colorant stabilizers can be covalently bonded to the molecular includant. In certain embodiments, the colorant will be associated with the molecular includant by means of hydrogen bonding and/or van der Waals forces or the like, while the stabilizing molecule is covalently bonded to the molecular includant. In other embodiments, the colorant is at least partially included within the cavity of the molecular includant, and the colorant stabilizer is located outside of the cavity of the molecular includant.

As a practical matter, the colorant, the colorant stabilizer and molecular includant are likely to be solids depending upon the constituents used to prepare the molecules. However, any or all of such materials can be a liquid. The colored composition can be a liquid either because one or more of its components is a liquid, or, when the molecular includant is organic in nature, a solvent is employed. Suitable solvents include, but are not limited to, amides, such as N,N-dimethylformamide; sulfoxides, such as dimethylsulfoxide; ketones, such as acetone, methyl ethyl ketone, and methyl butyl ketone; aliphatic and aromatic hydrocarbons, such as hexane, octane, benzene, toluene, and the xylenes; esters, such as ethyl acetate; water; and the like. When the molecular includant is a cyclodextrin, particularly suitable solvents are the amides and sulfoxides.

In an embodiment where the composition of the present invention is a solid, the effectiveness of the above compounds on the colorant is improved when the colorant and the selected compounds are in intimate contact or in an association that approaches van der Waals radii. To this end, the thorough blending of the components, along with other components which may be present, is desirable. Such blending generally is accomplished by any of the means known to those having ordinary skill in the art. When the colored composition includes a polymer, blending is facilitated if the colorant and the colorant stabilizer are at least partly soluble in softened or molten polymer. In such case, the composition is readily prepared in, for example, a two-roll mill. Alternatively, the composition of the present invention can be a liquid because one or more of its components is a liquid.

For some applications, the composition of the present invention typically will be utilized in particulate form. In other applications, the particles of the composition should be very small. Methods of forming such particles are well known to those having ordinary skill in the art.

The colored composition optionally may also contain a carrier, the nature of which is well known to those having ordinary skill in the art. For many applications, the carrier will be a polymer, typically a thermosetting or thermoplastic polymer, with the latter being the more common.

Examples of thermoplastic polymers include, but are not limited to: end-capped polyacetals, such as poly (oxymethylene) or polyformaldehyde, poly (trichloroacetaldehyde), poly(n-valeraldehyde), poly (acetaldehyde), poly(propionaldehyde), and the like; acrylic polymers, such as polyacrylamide, poly(acrylic acid), poly (methacrylic acid), poly(ethyl acrylate), poly(methyl methacrylate), and the like; fluorocarbon polymers, such as poly(tetrafluoroethylene), perfluorinated ethylenepropylene copolymers, ethylenetetrafluoroethylene copolymers, poly-(chlorotrifluoroethylene), ethylene-chlorotrifluoroethylene copolymers, poly(vinylidene fluoride), poly(vinyl fluoride), and the like; epoxy resins, such as the condensation products of epichlorohydrin and bisphenol A; polyamides, such as poly(6-aminocaproic acid) or poly(ε-caprolactam), poly (hexamethylene adipamide), poly(hexamethylene sebacamide), poly(11-aminoundecanoic acid), and the like; polyaramides, such as poly(imino-1,3-phenyleneiminoisophthaloyl) or poly(m-phenylene isophthalamide), and the like; parylenes, such as poly-p-xylylene, poly(chloro-p-xylene), and the like; polyaryl ethers, such as poly(oxy-2,6-dimethyl-1,4-phenylene) or poly(p-phenylene oxide), and the like; polyaryl sulfones, such as poly(oxy-1,4-phenylenesulfonyl-1,4-phenyleneoxy-1,4-phenylene-isopropylidene-1,4-phenylene), poly (sulfonyl-1,4-phenyleneoxy-1,4-phenylenesulfonyl-4,4-biphenylene), and the like; polycarbonates, such as poly (bisphenol A) or poly(carbonyldioxy-1,4-phenyleneisopropylidene-1,4-phenylene), and the like; polyesters, such as poly(ethylene terephthalate), poly (tetramethylene terephthalate), poly(cyclohexylene-1,4-dimethylene terephthalate) or poly(oxymethylene-1,4-cyclohexylenemethyleneoxyterephthaloyl), and the like; polyaryl sulfides, such as poly(p-phenylene sulfide) or poly (thio-1,4-phenylene), and the like; polyimides, such as poly (pyromellitimido-1,4-phenylene), and the like; polyolefins, such as polyethylene, polypropylene, poly(1-butene), poly (2-butene), poly(1-pentene), poly(2-pentene), poly(3-methyl-1-pentene), poly(4-methyl-1-pentene), 1,2-poly-1,3-butadiene, 1,4-poly-1,3-butadiene, polyisoprene, polychloroprene, polyacrylonitrile, poly(vinyl acetate), poly (vinylidene chloride), polystyrene, and the like; and copolymers of the foregoing, such as acrylonitrile-butadienestyrene (ABS) copolymers, styrene-n-butylmethacrylate copolymers, ethylene-vinyl acetate copolymers, and the like.

Some of the more commonly used thermoplastic polymers include styrene-n-butyl methacrylate copolymers, polystyrene, styrene-n-butyl acrylate copolymers, styrenebutadiene copolymers, polycarbonates, poly(methyl methacrylate), poly(vinylidene fluoride), polyamides (nylon-12), polyethylene, polypropylene, ethylene-vinyl acetate copolymers, and epoxy resins.

Examples of thermosetting polymers include, but are not limited to, alkyd resins, such as phthalic anhydrideglycerol resins, maleic acid-glycerol resins, adipic acidglycerol resins, and phthalic anhydride-pentaerythritol resins; allylic resins, in which such monomers as diallyl phthalate, diallyl isophthalate diallyl maleate, and diallyl chlorendate serve as nonvolatile cross-linking agents in polyester compounds; amino resins, such as aniline-formaldehyde resins, ethylene urea-formaldehyde resins, dicyandiamide-formaldehyde resins, melamine-formaldehyde resins, sulfonamide-formaldehyde resins, and urea-formaldehyde resins; epoxy resins, such as cross-linked epichlorohydrinbisphenol A resins; phenolic resins, such as phenolformaldehyde resins, including Novolacs and resols; and thermosetting polyesters, silicones, and urethanes.

In addition to the colorant, colorant stabilizer, and optional molecular includant, the colored composition of the present invention also can contain additional components, depending upon the application for which it is intended. Examples of such additional components include, but are not limited to, charge carriers, stabilizers against thermal oxidation, viscoelastic properties modifiers, cross-linking agents, plasticizers, charge control additives such as a quaternary ammonium salt; flow control additives such as hydrophobic silica, zinc stearate, calcium stearate, lithium stearate, polyvinylstearate, and polyethylene powders; and fillers such as calcium carbonate, clay and talc, among other additives used by those having ordinary skill in the art. Charge carriers are well known to those having ordinary skill in the art and typically are polymer-coated metal particles. The identities and amounts of such additional components in the colored composition are well known to one of ordinary skill in the art.

When the colorant stabilizers of the present invention are used to stabilize the dyes in ink jet inks, it is desirable to filter the compositions through a small pore filter (0.45μ) such as a Millipore® filter before the ink formulation is placed in an ink jet cartridge. This will reduce or eliminate clogging of the cartridge ink nozzles due to particulate matter.

Treated Substrates

As stated above, colorant stabilizers may be present in a colorant solution, or present on or in a substrate to which the colorant is to be applied. When a colorant stabilizer is present in or on a substrate, the substrate is referred to as a "treated substrate". In one embodiment of the present invention, a treated substrate contains a reducing agent thereon or therein. In another embodiment, a treated substrate contains a molecular includant thereon or therein. In yet another embodiment, a treated substrate contains a molecular includant and a reducing agent thereon or therein. The term "stabilizing agent" is used to denote the colorant stabilizer in or on a substrate.

The substrate may be, but is not limited to, paper, wood, a wood product or composite, woven fabric, nonwoven fabric, textile, plastic, glass, or any other substrate that would benefit from having a stabilized colorant thereon. A plastic substrate includes, but is not limited to, a plastic film, a plastic nonwoven web, or a plastic woven web. A preferred substrate is paper. Any existing or future type of paper or paper products may be used in the present invention.

Examples of paper or paper products include, but not limited to, printing and writing papers, packaging and industrial papers, paperboard, and tissue papers. Examples of printing and writing papers include, but are not limited to the following: wood-free coated papers; wood-containing coated papers; wood-free uncoated papers such as bond and writing paper, envelopes, offset and opaque circular, carbonless, tablet, forms bond, ledger, mimeograph, and manifold, duplication, fax base, thermal base, technical papers, supercalandered, and specialty papers; uncoated wood-containing papers such as supercalandered, directory, specialty converting and publishing; bristols such as coated bristols, uncoated bleached bristols, tag, coated tag papers, file folders, and tabulating; and thin papers such as cigarette paper, bible paper, lightweight paper, lightweight specialty, manifold, cotton fiber papers, and specialty thin papers.

Examples of Packaging and industrial papers include, but are not limited to the following: breached Kraft paper such as grocers bags, shipping sacks, wrapping paper, and converting paper; unbleached Kraft paper such as grocers bags, shipping sacks converting paper, wrapping paper, and envelopes. Examples of paperboard include, but are not limited to the following: containerboard such as unbleached linerboard, bleached linerboard, corrugated medium, and chip and filler board; folding boxboard/folding cartonboard such as solid bleached sulfite, bleached and unbleached bristols, coated recycled board, coated unbleached Kraft, milk, cup, plate and foodservice stock (coated or uncoated), and folding board; gypsum wallboard; and tube/can and drum paperboard. Examples of tissue papers include, but are not limited to, sanitary tissues such as bathroom tissue, facial tissue, napkins, toweling, wiper stock, and other sanitary tissue papers.

Molecular Includant

As stated above, a molecular includant is defined as any substance having a chemical structure which defines at least one cavity, wherein a cavity includes any opening or space of a size sufficient to accept at least a portion of a compound, such as, but not limited to, a colorant. The molecular includant can be inorganic or organic in nature. In certain embodiments, the chemical structure of the molecular includant is adapted to form a molecular inclusion complex. Molecular includants include, but are not limited to, clathrates or intercalates, zeolites, crown ethers, calixarenes, valinomycin type natural antibiotics, various polyether compounds, nigericin type natural antibiotics, or cyclic compounds containing a plurality of pyranose rings, for example, those having formed cyclic compounds through 1,4 and 1,6 bonding of monosaccharides such as glucose, fructose, galactose, etc. and disaccharides such as saccharose, maltose, lactose etc.

The cyclic compounds also include cyclodextrins such as alpha-cyclodextrin (or α-cyclodextrin), beta-cyclodextrin (or β-cyclodextrin), gamma-cyclodextrin (or γ-cyclodextrin), delta-cyclodextrin (or 6-cyclodextrin), and derivatives thereof such as hydroxypropyl β-cyclodextrin, hydroxyethyl β-cyclodextrin, hydroxyethyl α-cyclodextrin, carboxymethyl α-cyclodextrin, carboxymethyl β-cyclodextrin, carboxymethyl γ-cyclodextrin, octyl succinated α cyclodextrin, octyl succinated β-cyclodextrin, octyl succinated γ-cyclodextrin, sulfated β-cyclodextrin and sulfated γ-cyclodextrin, hydroxyethyl γ-cyclodextrin, hydroxyisopropyl γ-cyclodextrin, hydroxypropyl γ-cyclodextrin, octyl succinate γ-cyclodextrin, and carboxymethyl γ-cyclodextrin.

The α-cyclodextrins contain 6 glucopyranose rings, the β-cyclodextrins contain 7 glucopyranose rings, the γ-cyclodextrins contain 8 glucopyranose rings, and the Δ-cyclodextrins contain 9 glucopyranose rings. Cyclodextrins with 10, 11, or 12 glucopyranose rings may also be used in the present invention. A desirable cyclodextrin is any γ-cyclodextrin that is water soluble. In particular, hydroxyethyl γ-cyclodextrin, hydroxyisopropyl γ-cyclodextrin, and hydroxypropyl γ-cyclodextrin are desirable molecular includants for the present invention. Another desirable cyclodextrin is any β-cyclodextrin that is water soluble. In particular, hydroxyethyl γ-cyclodextrin is a preferred cyclodextrin.

The cyclodextrins suitable for the inks of the present invention can also, if desired, be modified by the addition of substituents. Substituents generally replace either the entire hydroxyl group or the hydrogen atom on one or more of the hydroxyl groups of the cyclodextrin ring. Examples of substituents include acyl groups, wherein one or more of the hydroxyl groups is replaced with groups such as —OAc, —OC(O)CH$_2$CH$_3$, —OC(O)(CH$_2$)$_2$CH$_3$, —OC(O)(CH2)$_3$CH$_3$, —OC(O)CF$_3$, —OC(O)Ph, or the like; alkyl and aryl groups, wherein one or more of the hydroxyl groups is replaced with groups such as —OCH$_3$, —OCH$_2$CH$_3$, —O(CH$_2$)$_2$CH$_3$, —OC (CH$_3$)$_3$, —OPh, or the like; tosyl (4-methylbenzenesulfonyl, or Ts) or related groups, wherein one or more of the hydroxyl groups is replaced with —OTs or the like; mesyl (methanesulfonyl, or Ms) or related groups, wherein one or more of the hydroxyl groups is replaced with —OMs or the like; amino groups, wherein one or more of the hydroxyl groups is replaced with groups such as a primary, secondary, or tertiary amine group, including cyclic amines and aromatic amines or the like; azido groups, wherein one or more of the hydroxyl groups is replaced with —N$_3$ or the like; halo substituents, wherein one or more of the hydroxyl groups is replaced with a halogen atom, such as —F, —Cl, —Br, or —I; nitro groups, wherein one or more of the hydroxyl groups is replaced with —ONO$_2$; phosphorus-containing groups, wherein one or more of the hydroxyl groups is replaced with groups such as —OPO$_3$H$_2$, —OPO$_3$R$_2$ (wherein R is alkyl or aryl), —OPO$_3$HR, or wherein two adjacent hydroxyl groups are replaced with groups such as —OP(O)(CH$_3$)O—, or the like; imidazole groups and their derivatives; pyridine groups and their derivatives; sulfur-containing functional groups, wherein one or more of the hydroxyl groups is replaced with groups such as —SCH$_3$, —SCH$_2$CH$_3$, —S(CH$_2$)$_2$CH$_3$, —SC(CH$_3$)$_3$, —OSO$_3^-$Na$^+$, —OCH$_2$SO$_3^-$Na$^+$, —OCH$_2$CH$_2$SO$_3^-$Na$^+$, —O(CH$_2$)$_3$SO$_3^-$Na$^+$, or the like; alcohol, aldehyde, ketone, or oxime groups; carboxylic acid groups and their derivatives; carbonate and carbamate groups; silicon, boron, or tin containing groups, wherein one or more of the hydroxyl groups is replaced with groups such as —$OSi(CH_3)_3$, —$OSi(CH_3)_2H$, —$CH_2OSi(CH_3)_3$, —$CH_2OSi(CH_3)_2H$, —$OB(CH_2CH_2)_2$, —$CH_2OB(CH_2CH_2)_2$, —$CH_2OSn((CH_2)_3CH_3)_3$, or the like; hydroxyalkyl groups, such as hydroxy ethyl groups, hydroxypropyl groups, or the like; or any other suitable substituent.

In another embodiment, substituent or substituents in the cyclodextrin molecules are bonded to an oxygen atom in a ring glucose unit. For example, the substituent can be an alkyl radical, desirably having up to about six carbon atoms. Another example of such a substituent has the formula —$(CH—CHR^1—O—)_n$—H wherein $R^1$ is selected from the class consisting of hydrogen and alkyl groups having up to about six carbon atoms. In the above formula, n is a small whole number having a value up to about six; desirably, n is equal to 1. Preferred substituents of this type are hydroxyethyl and hydroxypropyl.

Yet another type of substituent on the cyclodextrin is a bridging group that links two cyclodextrin moieties. The bridging groups have the formula —$CHR^1$—$CHOH$—$CHR_1$— wherein $R_1$ has the same significance as above. In these polymeric cyclodextrins, the number of cyclodextrin rings so bridged is from two to about six. In other words, there can be two cyclodextrin rings linked by the bridging group, or there can be three of the rings linked by two bridging groups, and so on, such that there can be six rings linked by five bridging groups. It is to be understood that higher polymers can be used in the invention if they have properties analogous to the polymers within the range given above, and the increased size or molecular weight does not confer an undesirable property to the extent that it makes the material unsuitable for use in the invention. The polymeric cyclodextrins may have substituents in addition to the group that links or bridges two cyclodextrin moieties. For example, the cyclodextrin moieties may have one or more carboxyalkyl (—R—COOH) substituents, wherein R is a lower alkylene radical having up to about 4 carbon atoms.

Cyclodextrin rings can also be bound together to form polymers by processes such as linking the cyclodextrin rings together with suitable multifunctional agents. For example, a poly-β-cyclodextrin can be formed that is crosslinked with epichlorohydrin; this material is commercially available from American Tokyo Kasei, Inc., 9211 N. Harborgate St., Portland, Oreg. 97203. It is to be understood that any method known to one of ordinary skill in the art may be used to covalently bind two or more molecular includants together. A desired embodiment is to have crosslinked γ-cyclodextrins in or on a substrate.

Cyclodextrins are commercially available from, for example, American Maize-Products Company, of Hammond, Ind. Additional information regarding cyclodextrins and modified cyclodextrins is widely available in the chemical literature, and is summarized in, for example, "Synthesis of Chemically Modified Cyclodextrins," A. P. Croft and R. A. Bartsch, *Tetrahedron*, Vol. 39, No. 9, pages 1417 to 1474 (1983), the disclosure of which is totally incorporated herein by reference. Substituted cyclodextrins are also shown in the publication "Molecusol™: Your Research Solution," Pharmetec, Inc. (1988), the disclosure of which is totally incorporated herein by reference. The hydroxypropyl substituted cyclodextrin is also suitable for the prevent invention.

Additionally, it is to be understood that the molecular includants of the present invention may have one or more of the stabilizer molecules discussed above, which may be admixed into a colorant solution, associated therewith. The term "associated", in its broadest sense, means that the stabilizer molecule is at least in close proximity to the molecular includant. For example, the stabilizer molecule can be maintained in close proximity to the molecular includant by hydrogen bonding, van der Waals forces, ionic bonding, hydrogen bonding, dipole-dipole interactions or the like.

The molecular includant in association with a colorant stabilizes the colorant. More particularly, the molecular includant stabilizes a colorant when it is present on or in the substrate upon which the colorant is applied.

In the embodiment where the molecular includant is present on or in the substrate, the molecular includant may be introduced onto or into the substrate by any method known to one of ordinary skill in the art, wherein the method does not destroy the molecular includant's ability to stabilize a colorant. In one embodiment, a treated substrate is one wherein the molecular includant is applied to the substrate in solution form and the substrate is subsequently dried to produce the substrate in the form it is to be utilized. Any substrate may be used, wherein the substrate does not destroy the molecular includant's ability to stabilize a colorant. A preferred substrate is paper. Any existing or future type of paper or paper products may be used in the present invention.

The molecular includant may be applied while the substrate is being manufactured, or it may be applied after the substrate has been manufactured. Where the substrate is paper, the molecular includant may be admixed into the pulp during the process of manufacturing the paper. An amount of molecular includant is admixed with the pulp so that the paper produced contains an amount of molecular includant effective to stabilize a colorant thereon. Desirably, between approximately 30 to 80% molecular includant by weight is admixed with the pulp. More desirably, between 50 to 65% molecular includant by weight is admixed with the pulp. A desirable amount of molecular includant in the final paper product is between 3% and 50% wt/wt. A more desired amount of molecular includant in the paper product is between 5 and 20%. Even more desired is between 7 and 10% of molecular includant in the paper product. Any method known in the art may be used to admix the molecular includant with the pulp, and produce the final paper product, wherein the molecular includant maintains its ability to stabilize a colorant. The above also applies to the manufacturing of wood pulp or composite substrates.

Alternatively, the molecular includant may be applied to a substrate after it has been manufactured, by dipping the substrate in a solution of the molecular includant, spraying the substrate, coating the substrate, or soaking the substrate with a solution of the molecular includant. Any method known in the art to apply a solution to a substrate and to dry the substrate may be used in the present invention so long as the molecular includant maintains its ability to stabilize a colorant. An amount of molecular includant solution is applied to the substrate so that after drying, the substrate contains an amount of molecular includant effective to stabilize a colorant thereon or therein.

Desirably, the concentration of the molecular includant solution is between 3% and 80% wt/wt. A more desired concentration is between 5 and 65%. An even more desired concentration is between 10 and 50%. A desirable amount of molecular includant in or on the treated substrate is between 1% and 50% wt/wt. A more desired amount of molecular includant in or on the treated substrate is between 3 and 25%. Even more desired is between 5 and 20% of molecular includant in or on the treated substrate. One embodiment of coating a molecular includant onto paper is fully described in Example 34.

In another embodiment, both the molecular includant and the colorant may be present within the substrate. The molecular includant and the colorant may be admixed with paper pulp, wood pulp, or monomers or oligomers, during the process of manufacturing paper, wood products, or plastics respectively. Alternatively, one of the above components can be introduced during the manufacturing process and the second component can be applied after the manufacturing process.

Examples 35 and 36 report the fade testing results of various magenta inks on treated and untreated paper. The magenta inks were studied as they tend to be the least stable of the widely used inks. More particularly, Hewlett-Packard (HP), American Ink Jet (AIJ), and Canon magenta ink jet inks, either with or without the stabilizing additives of the present invention, were printed on treated and untreated Hewlett-Packard premium paper and then exposed to an Atlas Weatherometer for a total of 77 hours. The inks containing the additives of the present invention contained 5% wt/wt of the basic fuschin imine adduct prepared in Example 7, 0.25 eq of tetramethylammonium iodide, and 2% wt/wt of hydroxyethyl β-cyclodextrin. It is to be understood that the molar equivalents of the various stabilizing compounds can be varied.

In Example 35, the treated paper was coated with γ-cyclodextrin as described in Example 34, such that the treated paper contained 7% wt/wt of the γ-cyclodextrin. After 77 total hours of exposure the change of color is measured and the ΔE* values compared. The ΔE* values reported in Example 35 for the HP and AIJ inks show that the molecular includant is an effective colorant stabilizer without the presence of additional stabilizing additives. More particularly, the ΔE* value for HP ink with no additives on untreated paper is 64, whereas the value for HP ink with no additives on cyclodextrin coated paper is 31.5. The ΔE* value for AIJ ink with no additives on untreated paper is 37, whereas the value for AIJ ink with no additives on cyclodextrin treated paper is 13.7

Additionally, the ΔE* values reported in Example 35 for the HP inks shows that the additives are an effective colorant stabilizer without the presence of the molecular includant in the paper. More particularly, the ΔE* value for HP ink with additives on untreated paper is 25.0, whereas the ΔE* value for HP ink with no additives on untreated paper is 64.0.

The ΔE* values reported in Example 35 also show that the molecular includant treated paper with the additive-containing ink yields unexpectedly superior colorant stabilization results. More particularly, the ΔE* value for HP ink with no additives on untreated paper is 64, with no additives on treated paper is 31.5, with additives on untreated paper is 25.0, and with additives on treated paper is 14.7. Accordingly, the ΔE* values show that although the additives alone stabilize the HP and AIJ inks, and treated paper alone stabilizes the HP and AIJ inks, the most lightfast colorant is stabilized by being associated with the additives in the solution and being printed on the treated paper.

In Example 36, three types of treated paper were studied along side of an uncoated paper. More particularly, HP Premium Ink Jet paper was treated with a 50% γ-cyclodextrin solution, a 20% sodium thiosulfate solution, or a 20% γ-cyclodextrin/10% sodium thiosulfate solution.

The uncoated paper that was also studied is Kimberly-Clark Bright White paper. After printing, and exposure in the Atlas Weatherometer for 77 hours, the ΔE* values were measured.

The ΔE* values reported in Example 36 also show that although the additives alone stabilize the HP and AIJ inks, and treated paper alone stabilizes the HP and AIJ inks, the most lightfast colorant is stabilized by being associated with the additives in the solution and being printed on the treated paper.

With respect to the Bright White paper stabilization results reported in Example 36, these results are not readily comparable to the stabilization results obtained regarding the HP Premium paper. More particularly, most ink jet papers are coated so that the ink is not absorbed into the fibers of the paper and instead remains on the surface of the paper. The coated paper thereby produces a superior ink jet printing quality. The HP Premium paper is an example of such a coated paper.

In contrast, the Kimberly-Clark Bright White paper is not a coated paper. Accordingly, when an ink is printed thereon, the ink is wicked or absorbed into the bulk of the fibers of the paper, and does not remain on the surface of the paper, thereby yielding a different quality of printing. Although not wanting to be bound by the following, it is theorized that the ink that is absorbed into the uncoated paper is protected from degradation from light by the fibers of the paper. In contrast, inks that are printed on coated paper remain on the surface of the paper and receive no protection from the fibers of the paper. Accordingly, the stability and quality of printing of inks that are printed on an uncoated paper cannot be compared directly to inks that are printed on coated paper.

Reducing Agent

In the embodiment where the treated substrate contains a reducing agent, the reducing agent may be, but is not limited to, sodium thiosulfate ($Na_2S_2O_3$), sodium sulfite ($Na_2SO_3$), cysteine, sodium nitrite, sodium phosphite, sodium citrate, citric acid, ascorbic acid, boron hydride, dithionite, hydrazine, thiourea-dioxide, hydrogen sulphite, potassium sulfite, ammonium sulfite, sodium hydrogen sulfite, potassium hydrogen sulfite, ammonium hydrogen sulfite, sodium trithionite, and polyhydric phenols. A desired reducing agent is sodium thiosulfate.

The reducing agent in association with a colorant stabilizes the colorant. The reducing agent stabilizes a colorant when it is present on or in the substrate upon which the colorant is applied, or when it is admixed with the colorant prior to its application to the substrate. Also, the reducing agent may be present both on or in the substrate upon which the colorant is applied and admixed with the colorant prior to its application. Additionally, the reducing agent may be applied to the colorant after the colorant has been applied to a substrate.

In the embodiment where the reducing agent is present on or in the substrate, the reducing agent may be introduced onto or into the substrate by any method known to one of ordinary skill in the art, wherein the method does not destroy the reducing agent's ability to stabilize a colorant. The reducing agent may be applied while the substrate is being manufactured, or it may be applied after the substrate has been manufactured. It is to be understood that when a reducing agent is present on or in a substrate in the form it is to be utilized, the substrate is referred to as a "treated substrate". In one embodiment, a treated substrate is one wherein the reducing agent was applied to the substrate in solution form and the substrate has been subsequently dried to produce the substrate in the form it is to be utilized.

Any substrate may be used, wherein the substrate does not destroy the reducing agent's ability to stabilize a colorant. As stated above, the substrate may be, but is not limited to, paper, wood, a wood product or composite, woven fabric, nonwoven fabric, textile, plastic, glass, or any other substrate that would benefit from having a stabilized colorant thereon. A preferred substrate is paper. Any existing or future type of paper may be used in the present invention, including, but not limited to, newsprint, coated wood containing paper, super calendared paper, fine paper, paperboard, and ink jet paper.

Where the substrate is paper, the reducing agent may be admixed into the pulp during the process of manufacturing the paper. An amount of reducing agent is admixed with the pulp so that the paper produced contains an amount of reducing agent effective to stabilize a colorant thereon. Desirably, between approximately 2 to 50% reducing agent by weight is admixed with the pulp. More desirably, between 3 to 30% reducing agent by weight is admixed with the pulp. A desirable amount of reducing agent in the final paper product is between 1% and 50% wt/wt. A more desired amount of reducing agent in the paper product is between 2 and 20%. Even more desired is between 3 and 10% of reducing agent in the paper product. Any method known in the art may be used to admix the reducing agent with the pulp, and produce the final paper product, wherein the reducing agent maintains its ability to stabilize a colorant. The above also applies to the manufacturing of wood pulp or composite substrates.

Alternatively, the reducing agent may be applied to a substrate after it has been manufactured, or in its final form, by dipping the substrate in a solution of the reducing agent, spraying the substrate, coating the substrate, or soaking the substrate with a solution of the reducing agent. Any method known in the art to apply a solution to a substrate and to dry the substrate may be used in the present invention so long as the reducing agent maintains its ability to stabilize a colorant. An amount of reducing agent solution is applied to the substrate so that after drying, the substrate contains an amount of reducing agent effective to stabilize a colorant thereon or therein.

Desirably, the concentration of the reducing agent solution is between 1% and 50% wt/wt. A more desired concentration is between 3 and 40%. An even more desired concentration is between 5 and 20%. A desirable amount of reducing agent in or on the treated substrate is between 1% and 50% wt/wt. A more desired amount of reducing agent in or on the treated substrate is between 2 and 20%. Even more desired is between 3 and 10% of reducing agent in or on the treated substrate. One method of coating a substrate with a reducing agent is fully described in Example 34.

In another embodiment, both the reducing agent and the colorant may be present within the substrate. The reducing agent and the colorant may be admixed with paper pulp, wood pulp, or monomers or oligomers, during the process of manufacturing paper, wood products, or plastics respectively. Alternatively, one of the above components can be introduced during the manufacturing process and the second component can be applied after the manufacturing process.

In yet another embodiment, the colorant and reducing agent are admixed in one solution and applied to a substrate simultaneously. For example, a colorant and an amount of reducing agent effective to stabilize the colorant can be in an ink jet ink cartridge in an ink jet printer. It is to be understood that any commercially available ink can be admixed with a reducing agent to stabilize the colorant therein. Desirably, the concentration of the reducing agent in ink is between 1 and 50% by weight. A more desired concentration is between 3 and 40%. An even more desired concentration is between 5 and 20%.

Examples 30 and 31 report the fade testing results of Hewlett Packard yellow ink printed on sodium thiosulfate treated paper and untreated paper. More particularly, yellow Hewlett Packard ink was printed on untreated paper and paper that had been dipped in a 10% wt/wt aqueous sodium thiosulfate solution and then dried. The papers were then exposed to an Atlas Weatherometer for a total of 51 hours. Visual and color measurements ($\Delta E^*$) show that the treated paper reduces the fade of the yellow ink. In particular, the $\Delta\Delta E^*$ values after 24 hours were 28.33 for the untreated paper, and 2.29 for the treated paper. The $\Delta E^*$ values after 51 hours were 54.96 for the untreated paper, and 12.08 for the treated paper. Accordingly, the $\Delta E^*$ values indicate little or no color change of the yellow ink on the treated paper over 51 the hours of exposure. These $\Delta E^*$ values therefore show that the reducing agent is an effective colorant stabilizer.

Although the reducing agent alone stabilizes a colorant, it is also desirable that the reducing agent be utilized with one or more of the above stabilizers. Example 29 reports the fade testing results of Hewlett Packard magenta ink admixed with various combinations of stabilizing compounds of the present invention printed on treated and untreated paper. More particularly, three molar equivalents of the triiodophenol sugar produced in Example 25, four molar equivalents of the trimethylphenol sugar produced in Example 23, and two molar equivalents of sodium iodide were admixed with HP magenta ink having already admixed therein 5% by weight β-hydroxyethyl cyclodextrin. This admixture is the additive-containing ink. It is to be understood that the molar equivalents of the various stabilizing compounds can be varied.

The magenta additive-containing ink or the commercially available magenta Hewlett Packard ink (control) was printed on untreated paper and paper that had been dipped in a 10% wt/wt aqueous sodium thiosulfate solution and then dried (the treated paper). The papers were then exposed to an Atlas Weatherometer for a total of 15 hours. Visual and color measurements ($\Delta E^*$) show that the control ink on untreated paper faded the most, the additive-containing ink on untreated paper faded less, and the additive-containing ink on treated paper barely faded at all, and faded the least. In particular, the $\Delta E^*$ values are as follows: 34.24 for control ink on untreated paper; 20.53 for additive-containing ink on untreated paper; and 11.09 for additive-containing ink on treated paper. Accordingly, the $\Delta E^*$ values show that although the additives alone stabilize the magenta colorant, the reducing agent in the paper further stabilizes the colorant in the presence of these additives.

Additionally, the substrate itself may be treated with one or more of the above reducing agents, one or more of the above molecular includants, or combinations thereof. In one embodiment, the substrate is treated with both a reducing agent and a molecular includant. Desirably, the reducing agent is sodium thiosulfate and the molecular includant is γ-cyclodextrin.

It is most desirable to treat a substrate with a reducing agent when the ink to be printed thereon is relatively pure. Although not wanting to be limited by the following, it is theorized that if ink containing a relatively substantial amount of impurities is printed on reducing agent-treated paper, the reducing agent will react with the impurities thereby decreasing its color stabilizing properties.

It has been unexpectedly discovered that the presence of a reducing agent in paper decreases the amount of yellowing that occurs on the paper upon exposure to the radiation. Example 28 reports the testing of treated and untreated paper for reduction of yellowing. More particularly, sheets of paper were dipped in the following: (1) a sodium iodide and sodium thiosulfate solution; (2) a sodium iodide solution; or (3) a sodium thiosulfate solution, and then dried. The above sheets and control sheets (which untreated) were placed into an Atlas Weatherometer overnight. The results are as follows: the sheets treated with solution (1) turned yellow; the sheets treated with solution (2) turned dark yellow; the sheets treated with solution (3) did not change, and remained white; and the control sheets turned a very pale yellow.

Example 28 illustrates that one of the colorant stabilizers of the present invention, namely, sodium iodide, increases the yellowing of paper. In contrast, the presence of the reducing agent, sodium thiosulfate, inhibits the yellowing of paper. Further, the presence of the reducing agent decreases the amount of yellowing resulting from the sodium iodide.

The present invention is further described by the examples which follow. Such examples, however, are not to be construed as limiting in any way either the spirit or scope of the present invention. In the examples, all parts are parts by weight unless stated otherwise.

EXAMPLE 1

Preparation of the Imine Adduct

To a 500 ml round bottomed flask is added 10.0 g chalcone (Aldrich), 8.3 g 2-amino benzene sulfonic acid (Aldrich), 200 ml of absolute ethanol, and 3 drops of dimethylamino ethanol (Aldrich). The reaction mixture is refluxed for one hour after which the solvent is removed to yield a pale yellow crystalline solid. The yield is 16.5 grams (95%). The reaction is represented as follows:

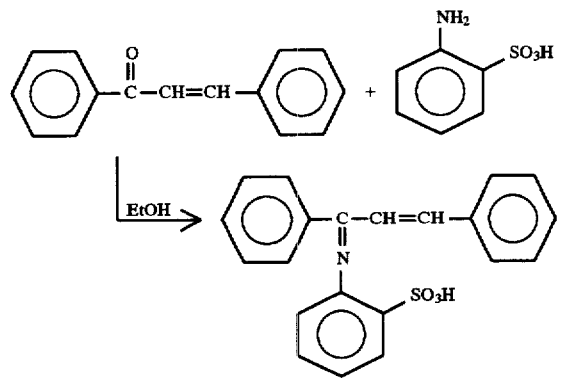

EXAMPLE 2

Preparation of Triiodophenolate Sodium Salt

To 25 g of triiodophenol (Aldrich) in a 250 ml round bottomed flask is added 100 ml diethyl ether. 52.5 ml of 1M sodium hydroxide (Fisher) is then added and the solution is stirred for 1 hour. The mixture is then rotoevaporated under reduced pressure to yield an off-brown solid which is used without further purification.

EXAMPLE 3

Effect of Triiodophenolate Sodium Salt and Triiodophenol on Degradation of Magenta Dye 1.5 equivalents to dye of triiodophenolate sodium salt from Example 2 or 1.5 equivalents of triiodophenol is added to 5 g of standard Hewlett Packard magenta ink jet ink formulation (Hewlett Packard, Palo Alto, Calif., Part No. HP 51640M). 2% (wt/wt) of ethyl hydroxy β-cyclodextrin is added to the ink samples. The sample is drawn down on a transparency (Hewlett-Packard, Palo Alto, Calif., Cat. No. HPC 3834A). The sample is then exposed for 10 minutes to a fusion lamp (Fusion UV Curing Systems Corp., Rockville, Md., Model F300+D-bulb) having a water cooled Pyrex filter. All absorbency measurements in these Examples were made on a Perkin-Elmer UV/VIS spectrophotometer (Perkin-Elmer Corporation, Norwalk, Conn., Model LAMBDA-14P). The results are shown in the following table.

| Time (min) | Control | Triiodophenolate | Triiodophenol |
|---|---|---|---|
| 0 | 0.8 | 0.87 | 0.74 |
| 10 | 0.27 | 0.77 | 0.70 |

EXAMPLE 4

Effect of Sodium Iodide on Degradation of Magenta Dye 10 and 2 equivalents of sodium iodide are added respectively to two aliquots of 5 g of standard Hewlett Packard magenta ink jet ink formulation (Hewlett Packard, Palo Alto, Calif., Part No. HP 51640 M). 2% (wt/wt) of ethyl hydroxy β-cyclodextrin is added to the ink samples. The sample is drawn down on a transparency (Hewlett-Packard, Palo Alto, Calif., Cat. No. HPC 3834A). The sample is then exposed for 10 minutes to a fusion lamp having a water cooled Pyrex filter. The results are shown in the following table.

| Time (min) | Control | NaI (10 eq.) | NaI (2 eq.) |
|---|---|---|---|
| 0 | 0.8 | 0.88 | 0.91 |
| 2 | 0.55 | 0.88 | 0.9 |
| 4 | 0.45 | 0.88 | 0.85 |
| 6 | 0.37 | 0.84 | 0.79 |
| 8 | 0.34 | 0.81 | 0.73 |
| 10 | 0.27 | 0.77 | 0.7 |

EXAMPLE 5

Effect of Imine Adduct on Degradation of Magenta Dye 1.5 equivalents of the imine adduct from Example 1 is added to 5 g of standard Hewlett Packard magenta ink jet ink formulation (Hewlett Packard, Palo Alto, Calif., Part No. HP 51640 M). 2% (wt/wt) of ethyl hydroxy β-cyclodextrin is added to the ink samples. The sample is drawn down on a transparency (Hewlett-Packard, Palo Alto, Calif., Cat. No. HPC 3834A). The sample is then exposed for 10 minutes to a fusion lamp having a water cooled Pyrex filter. The results are shown in the following table.

| Time (min) | Absorbency |
|---|---|
| 0 | 0.92 |
| 10 | 0.84 |

EXAMPLE 6

Effect of Imine Adduct on Degradation of Cyan Dye 4 equivalents or 1.5 equivalents to dye of the imine adduct from Example 1 is added to 5 g of standard Hewlett Packard cyan ink jet ink formulation (Hewlett Packard, Palo Alto, Calif., Part No. HP 51640 C). 2% (wt/wt) of ethyl hydroxy β-cyclodextrin is added to the ink samples. The sample is drawn down on a transparency (Hewlett-Packard, Palo Alto, Calif., Cat. No. HPC 3834A). The samples are then exposed for 10 minutes to a fusion lamp having a water cooled Pyrex filter. The results are shown in the following table.

| Time (min) | Control | Imine Adduct (4 eq.) | Imine Adduct (1.5 eq.) |
|---|---|---|---|
| 0 | 0.83 | 0.92 | 0.83 |
| 10 | 0.06 | 0.86 | 0.52 |

EXAMPLE 7

Preparation of the Imine Adduct of Basic Fuschin

A solution of 5.0 g basic fuschin (Aldrich) and 3.2 g chalcone (Aldrich) in 300 ml of absolute ethanol with 3 drops of dimethylamino ethanol is refluxed for 1 hour after which the solvent is removed to yield a green crystalline powder. The powder is placed under reduced pressure for 1 hour. The reaction is summarized as follows, wherein the product is referred to as "chalcone fuschin imine":

transparency (Hewlett-Packard, Palo Alto, Calif., Cat. No. HPC 3834A). The sample is then exposed for 10 minutes to a fusion lamp having a water cooled Pyrex filter. The results are shown in the following table.

| Time (min) | Control | Basic Fuschin Adduct |
|---|---|---|
| 0 | 0.99 | 0.80 |
| 10 | 0.38 | 0.78 |

EXAMPLE 9

Effect of Iodide Salts on Degradation of Magenta Dye 10 molar equivalents of sodium iodide, potassium iodide or tetramethylammonium iodide (($CH_3$)$_4$NI) to dye are added to 5 g of standard Hewlett Packard magenta ink jet ink formulation (Hewlett Packard, Palo Alto, Calif., Part No. HP 51640 M). 2% (wt/wt) of ethyl hydroxy β-cyclodextrin is added to the ink samples. The sample is drawn down on a transparency (Hewlett-Packard, Palo Alto, Calif., Cat. No. HPC 3834A). The samples is exposed for 10 minutes to a fusion lamp having a water cooled Pyrex filter. The results are shown in the following table.

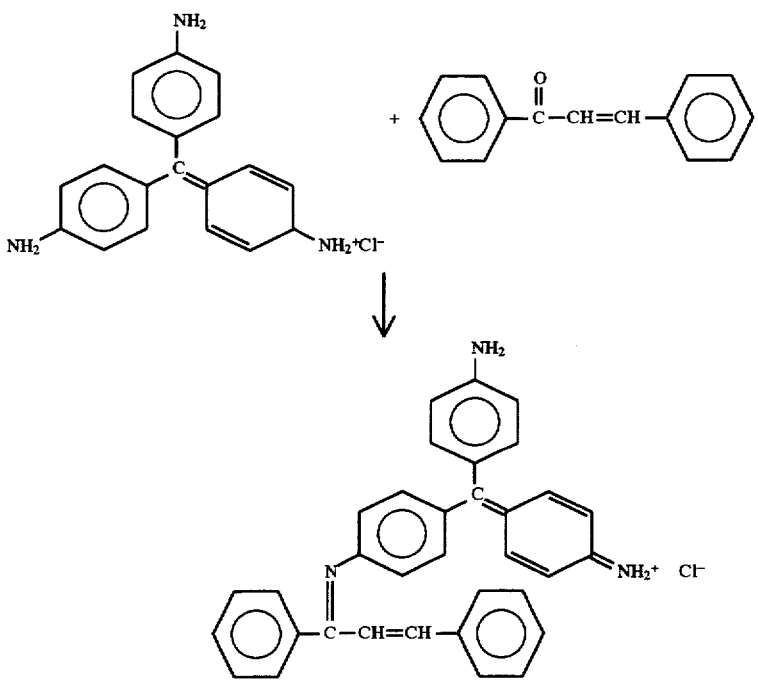

EXAMPLE 8

Effect of Basic Fuschin Imine Adduct on Degradation of Cyan Ink

As a control, basic fuschin dye (Aldrich) is dissolved in water (10% wt/wt) and applied to an HP transparency. The imine adduct from Example 7 is dissolved in water (10% wt/wt). 2% (wt/wt) to dye of the imine adduct from Example 7 is added to 5 g of standard Hewlett Packard cyan ink jet ink formulation (Hewlett Packard, Palo Alto, Calif., Part No. HP 51640 C). 2% (wt/wt) of ethyl hydroxy β-cyclodextrin is added to the ink samples. The sample is drawn down on a

| Time (min) | Control | NaI (10 eq.) | KI (10 eq.) | ($CH_3$)$_4$NI (10 eq.) |
|---|---|---|---|---|
| 0 | 0.80 | 0.96 | 0.73 | 0.80 |
| 10 | 0.27 | 0.79 | 0.47 | 0.68 |

EXAMPLE 10

Effect of Imine Adduct on Degradation of Magenta Dye under a Xenon Lamp 2 molar equivalents of the imine from Example 1 to dye is added to 5 g of standard Hewlett Packard magenta ink jet ink formulation (Hewlett Packard, Palo Alto, Calif., Part No. HP 51640 M). 2% (wt/wt) of ethyl hydroxy β-cyclodextrin is added to the ink samples. The sample is drawn down on a transparency (Hewlett-Packard, Palo Alto, Calif., Cat. No. HPC 3834A). The sample is then exposed for 4.5 hours to a xenon lamp (Universal Systems, Inc., Azuza, Calif., 1000 Watt Short-Arc Lamp, Model LPS-255HR.). The results are shown in the following table.

| Time (hrs) | Control | Imine Adduct |
|---|---|---|
| 0 | 0.81 | 0.91 |
| 4.5 | 0.33 | 0.83 |

EXAMPLE 11

Effect of the Combination of Triiodophenol and Tetramethylammonium Iodide on Degradation of Magenta Dye under a Fusion Lamp 2 molar equivalents of triiodophenol (Aldrich) to dye and 0.5 equivalents of $(CH_3)_4NI$ are added to 5 g of standard Hewlett Packard magenta ink jet ink formulation (Hewlett Packard, Palo Alto, Calif., Part No. HP 51640 M). 2% (wt/wt) of ethyl hydroxy β-cyclodextrin is added to the ink samples. The sample is drawn down on a transparency (Hewlett-Packard, Palo Alto, Calif., Cat. No. HPC 3834A). The samples are exposed for 10 minutes to a fusion lamp having a water cooled Pyrex filter. The absorbency of the transparency at zero time is 0.95 and after 10 minutes of exposure to the fusion lamp, the absorbency is 0.86 showing good stabilizing activity.

EXAMPLE 12

Effect of Triiodophenol on Degradation of Magenta Dye under a Fusion Lamp 2 molar equivalents of triiodophenol (Aldrich) to dye is admixed with 5 g of standard Hewlett Packard magenta ink jet ink formulation (Hewlett Packard, Palo Alto, Calif., Part No. HP 51640 M). 2% (wt/wt) of ethyl hydroxy β-cyclodextrin is added to the ink samples. The sample is drawn down on a transparency (Hewlett-Packard, Palo Alto, Calif., Cat. No. HPC 3834A). The samples are exposed for 10, 20 and 30 minutes to a fusion lamp having a water cooled Pyrex filter. The results of the test are shown in the following table:

| Time (min) | Absorbency |
|---|---|
| 0 | 0.97 |
| 10 | 0.97 |
| 20 | 0.96 |
| 30 | 0.83 |

EXAMPLE 13

Effect of the Combination of the Imine Adduct of Basic Fuschin and Sodium Iodide on Degradation of Magenta Dye under a Fusion Lamp 5% wt/wt of the imine adduct of basic fuschin from Example 7 and 1.5 equivalents of sodium iodide are admixed with 5 g of standard Hewlett Packard magenta ink jet ink formulation (Hewlett Packard, Palo Alto, Calif., Part No. HP 51640 M). 2% (wt/wt) of ethyl hydroxy β-cyclodextrin is added to the ink samples. The sample is drawn down on a transparency (Hewlett-Packard, Palo Alto, Calif., Cat. No. HPC 3834A). The sample is exposed for zero and 10 minutes to a fusion lamp having a water cooled Pyrex filter. The results of the test are shown in the following table:

| Time (min) | Absorbency |
|---|---|
| 0 | 0.83 |
| 30 | 0.83 |

EXAMPLE 14

Effect of the Combination of the Triiodophenol and Tetramethylammonium Iodide on Degradation of Cyan Dye under a Fusion Lamp 2 equivalents of triiodophenol (Aldrich) and 0.75 equivalents of $(CH_3)_4NI$ are added to 5 g of standard Hewlett Packard cyan ink jet ink formulation (Hewlett Packard, Palo Alto, Calif., Part No. HP 51640 C). 2% (wt/wt) of ethyl hydroxy β-cyclodextrin is added to the ink samples. The sample is drawn down on a transparency (Hewlett-Packard, Palo Alto, Calif., Cat. No. HPC 3834A). The samples is exposed for 10 minutes to a fusion lamp having a water cooled Pyrex filter. The results of the test are shown in the following table:

| Time (min) | Absorbency |
|---|---|
| 0 | 0.83 |
| 30 | 0.83 |

EXAMPLE 15

Effect of Stabilizers on the Viscosity Ink

A 1/16 inch hole is drilled in a Hewlett-Packard magenta ink cartridge and a syringe is used to remove the ink. 2 equivalents of triiodophenol and 2% wt/wt of ethyl hydroxy β-cyclodextrin are added to the ink sample and thoroughly mixed. The admixture is then put back into the cartridge using the syringe. An HP 1200C printer is used and 20 to 30 sheets are printed to get the cartridge to print fully. The viscosity is compared to control (untreated) ink by placing it in a burette and measuring volume poured from the cartridge in 10 seconds. Each value is the result of two pourings. The following table shows that the treated ink had approximately the same viscosity as the control ink.

| Experiment | Control | Additive |
|---|---|---|
| 1 | 6.4 g | 6.3 g |
| 2 | 5.4 g | 5.3 g |
| 3 | 6.0 g | 6.4 g |

EXAMPLE 16

Fade Test on Ink from Example 15

The cartridge prepared in Example 15 is used to print on a transparency (Hewlett-Packard, Palo Alto, Calif., Cat. No. HPC 3834A) so that a square inch of ink gives an absorbency reading of between 0.85 and 0.95. The square is then cut out and exposed to a fusion lamp having a water cooled Pyrex filter. The results of the test are shown in the following table:

| Time | Treated (Absorbency) | Control (Absorbency) |
|---|---|---|
| 0 | 0.97 | 0.88 |
| 10 | 0.97 | 0.83 |
| 20 | 0.96 | 0.59 |
| 30 | 0.83 | 0.42 |

EXAMPLE 17

Effect of Triiodophenol and Tetramethylammonium Iodide on Ink

A hole is drilled in a Hewlett-Packard magenta ink cartridge (Hewlett Packard, Palo Alto, Calif., Part No. HP 51640 M) and a syringe is used to remove the ink. 2 equivalents of triiodophenol and 0.5 equivalents of $(CH_3)_4NI$ and 2% wt/wt of ethyl hydroxy β-cyclodextrin is added to the ink sample and thoroughly mixed. The admixture is then put back into the cartridge using the syringe. The loaded cartridge is then placed in a HP 1200C printer and 20 pages are printed to stabilize the cartridge. Squares are then printed on transparencies according to Example 16. The squares are then cut out and exposed to a fusion lamp having a water cooled Pyrex filter. The results of the test are shown in the following table:

| Time (min) | Treated (Absorbency) | Control (Absorbency) |
|---|---|---|
| 0 | 0.90 | 0.88 |
| 20 | 0.85 | 0.59 |
| 30 | 0.80 | 0.42 |

No leakage or printing problems are observed and the cartridge is used to print 205 pages with no problems.

EXAMPLE 18

Cartridges are prepared according to Example 15 and printed on transparencies according to Example 16. The squares are exposed to xenon lamp radiation with a Pyrex/ water filter. The UV absorption is determined at the indicated times. The results of the test are shown in the following table:

| Time | Treated (Absorbency) | Control (Absorbency) |
|---|---|---|
| 0 hrs | 1.13 | 0.93 |
| 23 hrs | 1.06 | 0.61 |
| 44 hrs | 1.03 | 0.42 |

EXAMPLE 19

Examples of Compounds that did not Significantly Stabilize Dyes

Using protocols similar to those described in the previous examples, the following compounds were tested for their ability to stabilize the dyes in ink jet inks: 2,4,6-triiodobenzoic acid, sodium salt, β-carotene, 3,4-didehydroretinol (Vitamin A), ascorbic acid, 4-iodobenzoic acid, selenium EDTA complex and TINUVIN 936 (Ciba-Geigy Corporation). None of these representative compounds significantly stabilized any of the dyes tested.

EXAMPLE 20

Representative Combinations of Colorant Stabilizers

The following table represents various combinations of the desired colorant stabilizers that can be used to stabilize dyes. The particular combination that will be used will depend upon the final formulation of dye solution. The following table is not meant to be a comprehensive representation of all possible combinations but is only meant to show several possible combinations.

NaI=sodium iodide (NI)

$(CH_3)_4NI$=tetramethylammonium iodide (TI)

CD=cyclodextrin (CD)

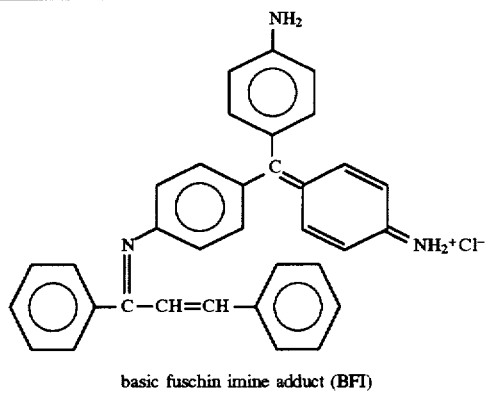

basic fuschin imine adduct (BFI)

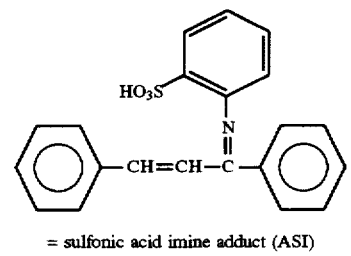

= sulfonic acid imine adduct (ASI)

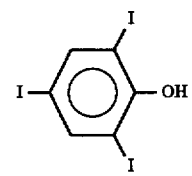

= triiodophenol (TIP)

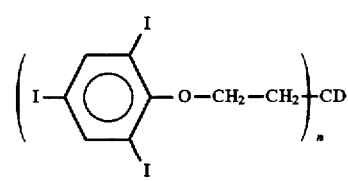

triiodophenol covalently bound to ethylhydroxy β-cyclodextrin. n = 3 (TIP—CD)

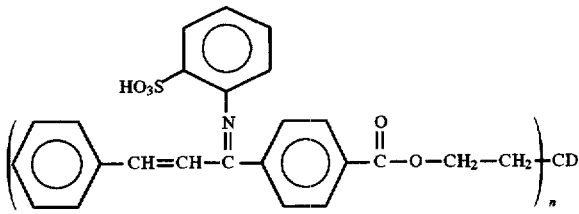

sulfonic acid imine adduct covalently bound to
ethylhydroxy β-cyclodextrin. n = 3 (ASI—CD)

-continued

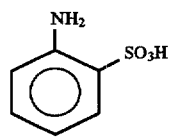

amino sulfonic acid (ASA)

| NI | (CH₃)₄NI | BFI | BFI + CD | BFI + TI | BFI + TI + CD | BFI + NI |
|---|---|---|---|---|---|---|
| TIP | TIP — CD | TIP + NI | TIP + NI + CD | TIP + TI | TIP + TI + CD | BFI + NI + CD |
| ASA | ASA + TI | ASA + TI + CD | ASI | ASI + TI | ASI + CD | ASI + CD + TI |
| NaI + CD | TI | TI+ CD | ASI— CD | ASI— CD + TI | ASI— CD + NI | |
| TIP + CD | TIP — CD | TIP — CD + NI | TIP — CD + TI | | | |
| ASA + CD | ASA + NI | ASA + NI + CD | | | | |

EXAMPLE 21

Preparation of Tosyl Sugar

To a 500 ml round bottom flask fitted with a magnetic stirrer and condenser is placed 75 g of 1,2-o-isopropylidene-D-glucofuranose (Aldrich) and 200 ml of anhydrous pyridine (Aldrich). The flask is cooled in an icebath and then 64.8 g of p-toluene sulfonyl chloride (Aldrich) is added. The mixture is stored overnight and allowed to warm to room temperature. The solvent is removed under reduced pressure, the oil redissolved in ether and washed with saturated copper sulfate solution, dried with MgSO₄, and the solvent removed to yield a light yellow viscous oil. The yield is 108.1 g (85%). The reaction is summarized as follows:

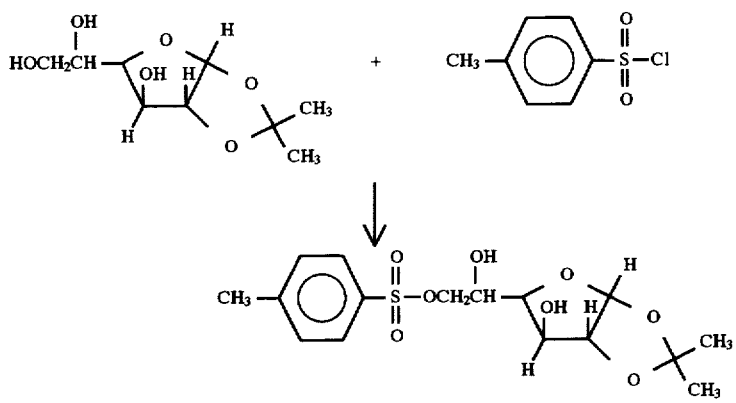

The resulting reaction product has the following reaction parameters:

1H NMR [DMSO-d₆] 7.5–8.8 (m, Tosyl-Aromatic Hs), 1.2–1.6 (m, sugar's ketal CH₃s)

EXAMPLE 22

Preparation of Trimethylphenol Sugar

To a 500 ml three-necked flask fitted with a magnetic stirrer, condenser and gas-inlet tube being continuously flushed with argon, 20.0 g of 2,4,6-trimethylphenol (Aldrich) and 150 ml of dry tetrahydrofuran ("THF") is placed into the flask. 4.2 g of sodium hydride is slowly added over 30 minutes and the gas evolution allowed to subside. The reaction mixture is stirred for 30 minutes after which 55.1 g of the tosyl sugar prepared in Example 21 is added in 50 ml of THF. The reaction mixture is stirred overnight and then refluxed for 60 minutes. The reaction mixture is then filtered and the solvent removed under reduced pressure to yield a brown oil. The oil is then dissolved in 200 ml of ether and 100 ml of 2N sodium hydroxide solution and the mixture stirred for one hour. The organic layer is then separated, dried with MgSO₄, and the solvent removed to yield a pale yellow oil. The yield is 32.1 g (62%). The reaction is summarized as follows:

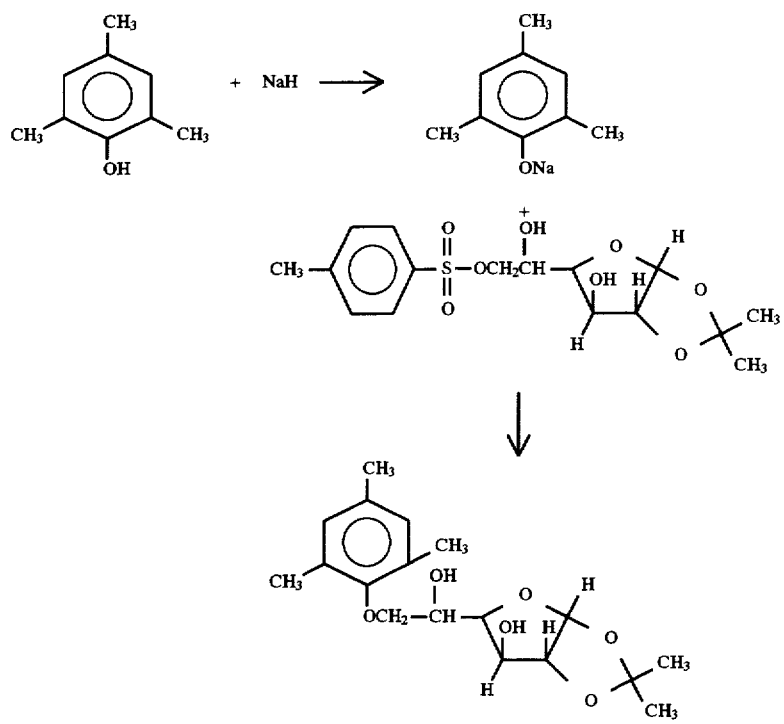

The resulting reaction product, (3aR, 6S, 6aR)-Tetrahydro-6-hydroxy-α-[(mesityloxy)methyl]-2,2-dimethylfuro[2,3-d]-1,3-dioxole-5-methanol, had the following physical parameters:

1H NMR [DMSO-d$_6$] key peaks: 7.3–6.8 (m), 4.8–3.7 (m), 2.2–2.5 (m), 1.5–1.7 (m) ppm.

Mass Spectrum: m/e: 338, 323, 281, 263, 265, 208, 203, 178, 149, 136, 121, 91, 73, 69.

EXAMPLE 23

Removal of Ketal Group

To a three necked flask fitted with a gas inlet and outlet and magnetic stirrer, is placed 20.0 g of the trimethylphenol sugar produced in Example 22 and 200 ml of anhydrous THF. Dry HCl gas (Matheson) is bubbled into the solution until the reaction mixture has a pH of 5–3 on moist Universal Indicator paper. The reaction was stirred at room temperature for one hour and the solvent removed under reduced pressure to yield a light brown oil The oil was found to be highly water soluble. The reaction is summarized as follows:

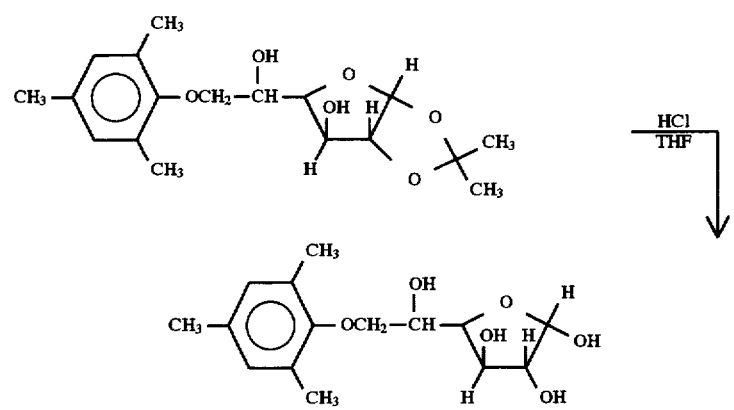

The resulting reaction product, (2S, 3R, 4R)-Tetrahydro-5-[1-hydroxy-2-(mesityloxy)ethyl]-2,3,4-furantriol, had the following physical parameters:

1H NMR [DMSO-d$_6$] showed loss of ketal CH$_3$ groups at 1.5 to 1.7 ppm.

EXAMPLE 24

Preparation of Triiodophenol Sugar

Into a three-necked round bottom flask fitted with a magnetic stirrer, gas inlet, and condenser, is placed 20 g 2,4,6-triiodophenol and 200 ml of dry THF. The flask is

43 cooled in an ice bath and 1.2 g of sodium hydride added slowly over 30 minutes. The mixture is then stirred for 30 minutes and then 15.6 g of tosyl sugar from Example 21 added in 50 ml of THF. The reaction is then heated to reflux overnight. The reaction mixture is then filtered and the solvent removed to yield a dark brown oil. The oil is then stirred in 200 ml of diethyl ether and 200 ml of 2N sodium hydroxide. The organic layer is then separated, dried with MgSO$_4$, and the solvent removed under reduced pressure to yield a pale yellow oil. The yield is 21.3 g (76%). The reaction is summarized as follows:

44

EXAMPLE 25

Removal of Ketal Group

To a 250 ml three necked round bottom flask fitted with gas inlet and outlet is placed 10.0 g of triiodophenol sugar produced in Example 24 and 150 ml of anhydrous THF. Dry HCl gas is bubbled into the reaction mixture until the solution has a pH of 3–5 on moist Universal Indicator paper (Fisher). The reaction mixture is then evaporated under reduced pressure to yield 8.8 g (96%) of a pale yellow oil. The reaction is summarized as follows:

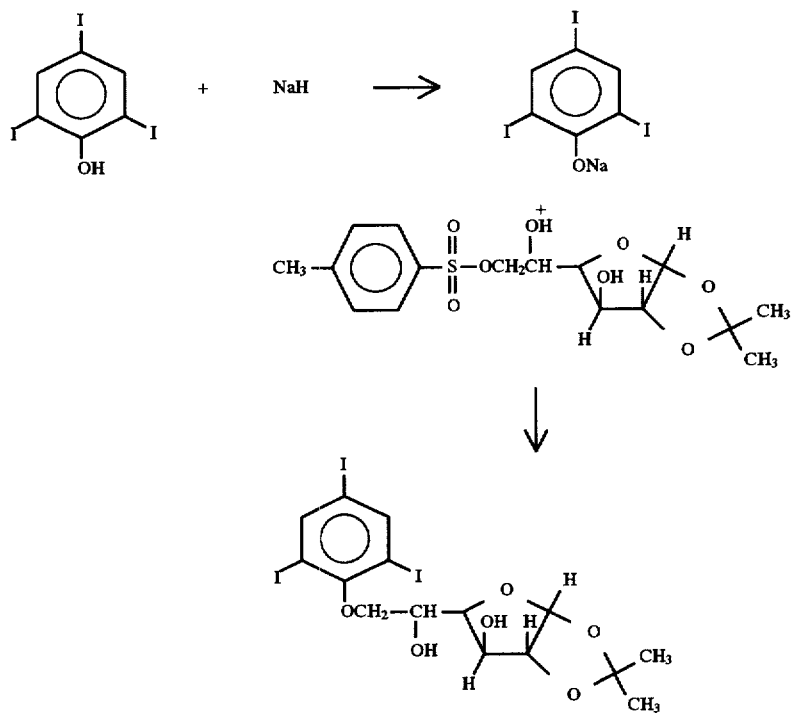

The resulting reaction product, (3aR, 6S, 6aR)-Tetrahydro-6-hydroxy-2,2-dimethyl-α-[(2,4,6-triiodophenoxy)methyl]furo [2,3-d]-1,3-dioxole-5-methanol, has the following physical parameters:

Mass Spectrum: m/e: 529, 460, 431, 402, 358, 289, 275, 231, 145, 129, 73.

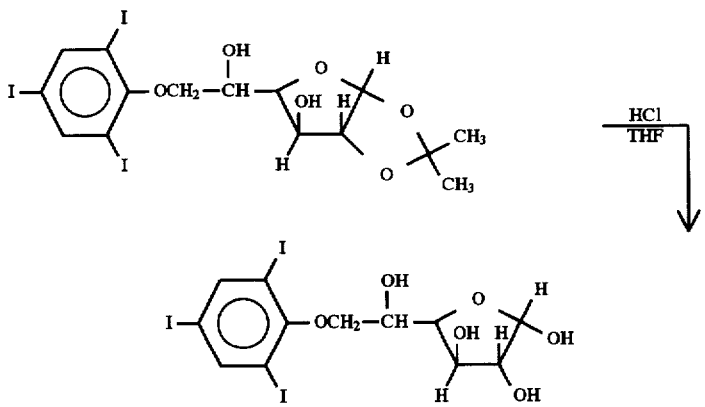

The resulting reaction product, (2S, 3R, 4R)-Tetrahydro-5-[1-hydroxy-2-(2,4,6-triiodophenoxy)ethyl]-2,3,4-furantriol, has the following physical properties:

Mass Spectrum: m/e: 529, 460, 347, 231, 145, 129, 73

EXAMPLE 26

Fade Testing of Hewlett Packard Magenta Ink with Additives Prepared in the Examples Above on Neenah Bond Paper Three Hewlett Packard HP51640M Magenta ink cartridges (Palo Alto, Calif.) are drilled with a ⅛ inch drill and the ink removed via syringe into a 250 ml Erlenmeyer flask. 4.8 g (2% wt/wt) β-hydroxyethyl cyclodextrin (American Maize) is added to the 96.7 g ink and the mixture shaken for 10 minutes to dissolve and disperse the cyclodextrin. Then 8.7 g trimethylphenol sugar (3 molar equivalents, or "eq") produced in Example 23, 19.3 g of triiodophenol sugar (4 eq) produced in Example 25, and 5.6 g of NaI (2 eq), are added to the mixture and shaken and sonicated for 20 minutes. The resultant mixture is then divided evenly into three aliquots, and one aliquot each of the resultant mixture is reintroduced into each of the drilled ink cartridges via syringe and filtered simultaneously through a 0.45 μfilter. The cartridges are then placed into a Hewlett Packard 1600C printer and test sheets are printed out on Neenah Bond, Kimberly Clark Corporation. Sheets number 30–32 are generated and subjected to fade studies against control sheets as described above, except that the sheets are exposed to an Atlas Electric Devices Co. (Chicago, Ill.) Weatherometer, Model No. C135W, radiance is at 0.53 watts/m$^2$ at 340 nm, wherein the black panel is at 32° C., borosilicate filters, and the humidity is 50%. Absorbency is measured after 0 and 66 hours of exposure of the control and experimental samples generated above. Absorbency is measured with a Perkin Elmer UV/Visible Spectrophotometer λ14B.

The results of the fade studies are shown in the tables below. The table below reports the fade study absorbancy results for the control sheet samples at 0 and 66 hours.

CONTROL SHEETS

| Sample No. | Absorbancy at 0 and 66 hours | |
|---|---|---|
| | $T_0$ | $T_{66}$ |
| 1 | 1.2 | 0.00 |
| 2 | 1.2 | 0.10 |
| 3 | 1.2 | 0.15 |
| 4 | 1.2 | 0.14 |
| 5 | 1.2 | 0.13 |
| 6 | 1.18 | 0.15 |

The table below reports the fade study absorbancy results for the experimental sheet samples generated as described above at 0 and 66 hours.

EXPERIMENTAL SHEETS

| Sample No. | Absorbancy at 0 and 66 hours | |
|---|---|---|
| | $T_0$ | $T_{66}$ |
| 1 | 1.07 | 0.90 |
| 2 | 1.10 | 0.85 |
| 3 | 1.10 | 0.80 |
| 4 | 1.05 | 0.85 |
| 5 | 1.10 | 0.85 |

EXAMPLE 27

Fade Testing of Hewlett Packard Magenta Ink on Transparency Sheets

The procedure of Example 26 is repeated except that the control and experimental inks are printed on Hewlett Packard Premium Transparency HPC 3834A sheets instead of on Neenah Bond paper. The control sheet absorbancy values after 66 hours are 0.09 for sample 1, and 0.02 for sample 2. The experimental absorbancy value after 66 hours is 0.79 for sample 1.

EXAMPLE 28

Testing of Treated Paper for Reduction of Yellowing

The yellowing of paper is tested by dipping the paper in a solution as described below, drying the paper, and then exposing the paper in a weatherometer for 12 hours. More particularly, the paper is placed in a container to soak in the solution, hung on a line in a fumehood to drip dry, and then oven dried as described below.

Solution A Sodium Iodide+Sodium Thiosulfate

A 6.7% wt/wt sodium iodide and 10% wt/wt sodium thiosulfate solution in water is prepared. Strips of Neenah bond paper are dipped into the solution and then dried in a vacuum oven at 60° C. for 15 minutes. The paper is then placed into an Atlas Weatherometer and exposed to the following conditions for twelve hours: 0.53 W/m$^2$, 50% humidity, 32° C.

Solution B Sodium Iodide

A 6.7% wt/wt solution of sodium iodide is prepared and Neenah bond paper strips are dipped therein, dried, and exposed in a weatherometer as described above.

Solution C Sodium Thiosulfate

A 10% wt/wt solution of sodium thiosulfate is prepared and Neenah bond paper strips are dipped therein, dried, and exposed in a weatherometer as described above.

Control

Strips of Neenah bond paper were cut and exposed in a weatherometer as described above.

The results of exposing the treated and control strips of paper are as follows: The paper treated with solution A turned yellow. The paper treated with solution B turned dark yellow. The paper treated with solution C did not change, and remained white. The control samples turned very pale yellow. Accordingly, treating paper with sodium thiosulfate reduces the amount of yellowing that occurs over time.

EXAMPLE 29

Fade Testing of Hewlett Packard Inks Printed on Sodium Thiosulfate Treated Paper This example determines if sodium thiosulfate treated paper enhances the resistance to fade of Hewlett Packard Ink admixed with the colorant stabilizers of the present invention.

Several sheets of Hewlett Packard premium ink jet paper are soaked in a 10% wt/wt aqueous solution of sodium thiosulfate, and then dried in a vacuum oven at 60° C. for 15 minutes at 0.1 mm Hg. These sheets are referred to as the "treated paper".

The Hewlett Packard ink cartridge (magenta ink) is prepared as described above, by drilling a hole in the cartridge, removing the ink via a syringe, and placing the ink in an Erlenmeyer flask. 5% wt/wt of hydroxyethyl-β-cyclodextrin is put into the flask, and the mixture shaken for 10 minutes. Afterwards, 3 equivalents of triiodophenol sugar produced in Example 25, 4 equivalents of trimethylphenol sugar produced in Example 23, and 2 equivalents of sodium iodide are added to the mixture and shaken for 20 minutes It is to be understood that "equivalents" above are molar equivalents to the dye in the ink. The Ink mixture is then reinjected into the ink jet cartridge via syringe with 0.45μ filter attachment. This cartridge is referred to as the additive containing cartridge.

Test sheets are printed using control cartridges (other Hewlett Packard ink jet cartridges, including magenta, yellow, and cyan, without the above additives) and the additive containing cartridge on treated and untreated paper. More particularly, treated and untreated sheets are printed with Hewlett Packard magenta, yellow, and cyan ink cartridges that do not contain additives. Additionally, treated and untreated sheets are printed with Hewlett Packard yellow and cyan ink cartridges that do no contain additives and with the additive containing cartridge that contains magenta ink. The paper is then placed in the Atlas Weatherometer and exposed for 15 hours to the following conditions: 0.53 W/m$^2$ at 340 nm, 50% humidity, borosilicate filters, and 32° C.

The change in color is measured by the Xrite Colorimeter (Model 938, SpectroDensitometer, Grandville, Mich.) which measures the ΔE* values, based on the L, a*, b* as described by Cielab, D-50-2.

Visual and actual measurements show the control magenta ink on untreated paper faded the most, the additive-containing magenta ink on untreated paper faded less, and the additive-containing magenta ink on treated paper barely faded at all, and faded the least. More particularly, the ΔE* values are as follows:

| Paper | Magenta Ink | ΔE* Values |
| --- | --- | --- |
| Untreated | Control | 34.24 |
| Untreated | Additives | 20.53 |
| Treated | Additives | 11.09 |

Percentage wise, additive containing ink is 40% better in fade resistance than control ink (both on untreated paper), and additive containing ink on treated paper is 68% better in fade resistance than control ink on untreated paper, after 15 hours exposure.

Examination of the % Reflectance graphs of the samples before and after fading shows that the magenta dye does not fade or its concentration change when the additive is present in the ink and it is printed on the treated paper. However, the control clearly shows loss of the dye chromophore. In contrast, the additive system in the ink protects the loss of dye, however the ΔE* values show that the additive system yellows somewhat upon exposure to light, hence yielding the ΔE* value. The treated paper therefore decreases this yellowing of the additive thus giving the smallest ΔE* (color change) after 15 hours of exposure.

EXAMPLE 30

Fade Testing of Yellow Hewlett Packard Inks Printed on Sodium Thiosulfate Treated Paper and Untreated Paper This example determines if sodium thiosulfate treated paper enhances the resistance to fade of yellow Hewlett Packard Ink.

The papers exposed to the Atlas Weatherometer in Example 29 also had yellow and cyan squares printed thereon in boxes next to the magenta squares. Although some of the magenta squares contained the stabilizing additives, all of the yellow and cyan squares did not contain the additives.

Accordingly, yellow Hewlett Packard Ink is printed on both treated and untreated Hewlett Packard premium ink jet paper and then exposed to the Atlas Weatherometer under the conditions listed in Example 29. It is to be understood that the treated paper is soaked in a 10% wt/wt solution of sodium thiosulfate and dried in a vacuum oven under the conditions listed in Example 29.

The yellow ink on the weatherometer-exposed treated paper has little or no fading in comparison with the yellow ink on the unexposed treated paper. However, the yellow ink on the weatherometer-exposed untreated paper is substantially faded in comparison with the yellow ink on the unexposed untreated paper. Accordingly, the treated paper reduces the fade of the yellow ink in comparison to the untreated paper.

EXAMPLE 31

Fade Testing of Yellow Hewlett Packard Inks Printed on Sodium Thiosulfate Treated Paper and Untreated Paper This example determines if sodium thiosulfate treated paper enhances the resistance to fade of yellow Hewlett Packard Ink.

Additional ink samples were printed of Hewlett Packard inks, including yellow ink, on treated and untreated paper using the method described in Example 29. The samples were placed in the Atlas Weatherometer under the conditions listed in Example 29, except that the samples were exposed for a total of 51 hours.

Visual and color measurements (ΔE*) show that the treated paper reduces the fade of the yellow ink. More particularly, the ΔE* values for the yellow ink are as follows:

| Hours of Exposure | ΔE* Values for Untreated Paper | ΔE* Values for Treated Paper |
| --- | --- | --- |
| 24 | 28.33 | 2.29 |
| 51 | 54.96 | 12.08 |

The ΔE* values indicate little or no color change of the yellow ink on the treated paper over 51 hours.

EXAMPLE 32

Fade Testing of Cyan Hewlett Packard Inks Printed on Sodium Thiosulfate Treated Paper and Untreated Paper Samples were printed of Hewlett Packard inks, including cyan ink, on treated and untreated paper using the method described in Example 29. It is to be understood that none of the cyan inks contained the stabilizing additives listed in Example 29. The samples were placed in the Atlas Weatherometer under the conditions listed in Example 29, except that the samples were exposed for a total of 51 hours.

The treated paper had little or no effect on the fade of the Hewlett Packard cyan ink in comparison to the untreated paper. At 24 hours and 51 hours of total exposure to the Weatherometer, the cyan ink faded to a similar extent on the treated and untreated paper.

EXAMPLE 33

Fade Testing Of Inks Printed On Treated Paper

Fade testing of a magenta American Ink Jet ink jet formulation for a Canon printer is conducted as follows. The magenta ink is printed on cyclodextrin treated paper and sodium thiosulfate treated paper, and then exposed for 100 hours in an Atlas Weatherometer.

More particularly, approximately 10 ml of ink is removed from a small cartridge for a Canon BJC printer by use of a syringe with needle, via the wick plug. The following stabilizing additives are admixed with the magenta ink: 5% wt/wt of basic fuschin imine adduct prepared in Example 7; 0.25 eq tetramethylammonium iodide; and 2% wt/wt hydroxyethyl-γ-cyclodextrin. The ink admixture is placed back into the cartridge via syringe with a 0.45μ filter. The first 15 to 20 sheets printed are discarded to ensure that the ink admixture is being printed on the paper to be exposed to the Atlas Weatherometer.

Sodium Thiosulfate Treated Paper

The sodium thiosulfate treated paper is prepared as follows. A stock solution of 15 g sodium thiosulfate is placed in a beaker of 150 g of water and dissolved. The solution is placed in a Pyrex oven dish and sheets of Hewlett Packard Premium ink jet paper are placed therein, one sheet at a time. After the sheet has soaked in the sodium thiosulfate solution for 3 to 4 minutes, the sheets are removed and placed in a vacuum oven which is heated to 30°–32° C. and the vacuum of 0.1 torr applied for 15 to 20 minutes, producing dried sheets of paper.

By weighing a sheet before submersion in the sodium thiosulfate solution, and after the drying step, the amount of sodium thiosulfate present on or in the paper is calculated to be approximately 12% wt/wt.

Cyclodextrin Treated Paper

The cyclodextrin treated paper is prepared as follows. A 10% wt/wt solution of hydroxyethyl-γ-cyclodextrin is prepared, and sheets of Hewlett Packard Premium ink jet paper are treated as described above. By weighing a sheet before submersion in the cyclodextrin solution, and after the drying step, the amount of cyclodextrin present on or in the paper is calculated as approximately 3.4%.

A series of sheets are printed on the Canon BJC printer using the ink admixture prepared above or the commercially available ink for the printer as the control. Untreated sheets are printed (control), as well as sodium thiosulfate treated sheets and cyclodextrin treated sheets. The sheets are then exposed to light radiation for 100 hours in an Atlas Weatherometer having the following conditions: 0.54 W/m² at 440 nm irradiance; black panel temperature of 45° C.; borosilicate filters; and humidity of 55%. The color change readings (ΔE*) are measured using the X-rite meter. The results are reported below.

| Sample | ΔE* | ΔH* |
|---|---|---|
| Control ink on untreated paper | 47.6 | −3.1 |
| Ink admixture on untreated paper | 15.7 | 15.3 |
| Ink admixture on cyclodextrin paper | 5.9 | 0.6 |
| Ink admixture on thiosulfate paper | 9.3 | 2.8 |

As can be seen above, the stabilizing molecules in the ink admixture improve the light fastness and give a slight shift in hue of the colorant therein upon exposure to radiation. However, the above data clearly shows that the stabilizing molecules in the ink, in combination with the ink being printed on the treated paper, significantly improves the colorants resistance to fade upon exposure to radiation. The cyclodextrin treated paper gave the colorant the greatest improvement in light fastness, with the sodium thiosulfate treated paper giving the colorant the second best improvement in light fastness.

EXAMPLE 34

Preparation of Treated Paper

This examples describes one method of treating paper with either cyclodextrin or sodium thiosulfate. Hewlett-Packard premium ink jet paper is coated and dried to obtain flat treated paper for ink jet fade studies described in Examples 35 and 36.

More particularly, the paper is coated as follows. The paper is rolled between two rollers that are positioned on top of each other, wherein the bottom portion of the bottom roller is submersed in a solution of either cyclodextrin or sodium thiosulfate, and wherein a controlled amount of the same solution is continually dripped onto the top portion of the top roller. It is to be understood that as the paper rolls between the rollers, the paper is coated on its top surface by contact with the lower portion of the top roller which contains the solution thereon, and the solution continues to be applied to the top portion of the top roller as it rolls via contact with the paper. Additionally, as the paper rolls between the rollers, the paper is coated on its bottom surface by contact with the top portion of the bottom roller which contains the solution thereon, and the solution continues to be applied to the lower portion of the bottom roller (which is submersed in the solution) as it rolls via contact with the paper.

After the paper passes through the rollers as described above, it is rolled onto a steel, steam heated drum with a fabric flap to prevent the paper from curling as it is dried thereon.

The γ-yclodextrin treated paper is prepared as follows. The HP premium paper is weighed prior to treatment. A 50% by weight aqueous solution of γ-yclodextrin is prepared and applied to the top and bottom surfaces of the HP premium paper as described above. After the treated paper is dried, the paper is again weighed to yield a 7% wt/wt cyclodextrin content in or on the paper.

The sodium thiosulfate treated paper is prepared as follows. The HP premium paper is weighed prior to treatment. A 20% by weight aqueous solution of sodium thiosulfate is prepared and applied to the top and bottom surfaces of the paper as described above. After the treated paper is dried, the paper is again weighed to yield a 2% wt/wt sodium thiosulfate content on or in the paper.

These treated papers are used in the fade testing studies reported in Examples 35 and 36.

EXAMPLE 35

Fade Testing of Various Magenta Inks on Treated Paper

This example reports the results of fade testing of Hewlett-Packard (HP), American Ink Jet (AIJ), and Canon magenta ink jet inks, either with or without the stabilizing additives of the present invention, on treated or untreated Hewlett-Packard Premium paper.

The inks having the stabilizing additives of the present invention are prepared as described in the above examples, wherein the ink is removed from the appropriate cartridge, mixed with the additives, shaken and then sonicated for 20 minutes, then injected into the original cartridge via syringe fitted with a 0.45μ filter. The resultant ink contains the following additives: 5% wt/wt of the basic fuschin imine adduct prepared in Example 7; 0.25 eq of tetramethylammonium iodide; and 2% wt/wt hydroxyethyl β-cyclodextrin.

The magenta inks are printed onto HP premium paper and the treated paper prepared in Example 34. The Hewlett-Packard inks and the American Ink Jet inks are printed using a Hewlett-Packard 1600C printer and the Canon inks are printed using a BJC-600 printer.

The sheets were then placed in the Atlas Weatherometer and exposed for a total of 77 hours under the following conditions: 0.54 W/m$^2$ at 440 nm, borosilicate filters, 55% humidity, and 45° C. black panel temperature.

The change in color of the magenta ink is measured by the Xrite Colorimeter (Model 938, SpectroDensitometer, Grandville, Mich.) which measures the ΔE* values, based on the L, a*, b* as described by Cielab, D-50-2. The results are reported in the table below.

| | ΔE* Values | | | |
|---|---|---|---|---|
| Samples | 24 Hrs. | 45 Hrs. | 63 Hrs. | 77 Hrs. |
| HP Ink on HP Paper | 12.5 | 24.6 | 41.1 | 64.0 |
| HP Ink on CD Treated Paper | 9.1 | 13.3 | 20.0 | 31.5 |
| HP Ink + Additives on HP Paper | 5.3 | 9.9 | 17.1 | 25.0 |
| HP Ink + Additives on CD Paper | 7.4 | 9.9 | 12.3 | 14.7 |
| AIJ Ink on HP Paper | 6.3 | 12.1 | 22.0 | 37.0 |
| AIJ Ink on CD Treated Paper | 2.7 | 4.3 | 8.0 | 13.7 |
| AIJ Ink + Additives on CD Paper | 1.2 | 1.6 | 1.7 | 3.5 |
| Canon Ink on HP Paper | 5.6 | 6.0 | 7.0 | 9.0 |
| Canon Ink + Additives on Thiosulfate Treated Paper | 1.6 | 1.8 | 2.0 | 2.4 |

As shown above, the additives reduce fade, and when the ink containing the additives is printed on treated paper, the amount of fade is even further reduced.

EXAMPLE 36

Fade Testing of Various Magenta Inks on Treated Paper

This example reports the results of fade testing of Hewlett-Packard (HP), American Ink Jet (AIJ), and Canon magenta ink jet inks, either with or without the stabilizing additives of the present invention, on treated or untreated paper. More particularly, the paper is untreated Hewlett-Packard Premium paper, Kimberly-Clark Bright White ink jet paper, or Hewlett-Packard Premium paper treated as described in Example 34. Three types of treated paper are prepared using one of the following three aqueous solutions: 50% wt/wt γ-yclodextrin; 20% wt/wt sodium thiosulfate; or 20% wt/wt γ-yclodextrin and 10% wt/wt sodium thiosulfate.

As stated above in Example 34, the 50% cyclodextrin treated paper has a 7% wt/wt cyclodextrin content in or on the paper, and the 20% sodium thiosulfate treated paper has a 2% wt/wt sodium thiosulfate content in or on the paper. The paper treated with the 20% wt/wt γ-cyclodextrin and 10% wt/wt sodium thiosulfate solution is weighed before and after treatment, to yield a 4 to 5% wt/wt total content of cyclodextrin and sodium thiosulfate in or on the paper.

The treated and untreated paper is printed with the additive containing inks prepared in Example 35 or with the corresponding non-additive containing inks. The HP and AIJ inks were printed from HP 1600 cartridges using an HP 1600C printer. The Canon ink was printed with a BJC-600 printer.

The sheets were then placed in the Atlas Weatherometer and exposed for a total of 77 hours under the following conditions: 0.54 W/m$^2$ at 440 nm, 55% humidity, 45° C. black panel temperature, borosilicate filters.

The change in magenta color is measured by the Xrite Colorimeter (Model 938, SpectroDensitometer, Grandville, Mich.) which measures the ΔE* values, based on the L, a*, b* as described by Cielab, D-50-2. The results are reported in the table below.

| | Values at 77 Hours | |
|---|---|---|
| Paper | ΔE* | ΔH* |
| HP Inks With Additives | | |
| Hewlett-Packard Paper | 25.0 | 13.3 |
| 50% Cyclodextrin | 14.7 | 9.0 |
| 20% Cyclodextrin/10% Thiosulfate | 15.7 | 8.0 |
| 20% Thiosulfate | 20.4 | 12.2 |
| Kimberly-Clark Bright White | 16.0 | — |
| HP Inks (No Additives) | | |
| Hewlett-Packard Paper | 64.0 | 11.3 |
| 50% Cyclodextrin | 31.5 | 10.5 |
| 20% Cyclodextrin/10% Thiosulfate | 21.0 | 10.3 |
| 20% Thiosulfate | 27.2 | 13.6 |
| Kimberly-Clark Bright White | 32.5 | 10.8 |
| AIJ Inks With Additives | | |
| Hewlett-Packard Paper | 11.8 | 0.12 |
| 50% Cyclodextrin | 3.5 | 0.1 |
| 20% Cyclodextrin/10% Thiosulfate | 10.0 | 1.9 |
| 20% Thiosulfate | 11.4 | 1.5 |
| Kimberly-Clark Bright White | 8.0 | 2.0 |
| AIJ Inks (No Additives) | | |
| Hewlett-Packard Paper | 37.0 | −3.11 |
| 50% Cyclodextrin | 13.7 | −3.7 |
| 20% CD/10% Thiosulfate | 21.2 | 16.6 |
| 20% Thiosulfate | 5.6 | 4.0 |
| Kimberly-Clark Bright White | 13.8 | −0.47 |
| Canon Inks With Additives | | |
| Hewlett-Packard Paper | 8.2 | 2.7 |
| 50% Cyclodextrin | 4.3 | 3.2 |
| 20% Cyclodextrin/10% | 2.4 | 1.3 |

-continued

| Paper | Values at 77 Hours | |
|---|---|---|
| | ΔE* | ΔH* |
| Thiosulfate | | |
| 20% Thiosulfate | 2.4 | 0.01 |
| Kimberly-Clark Bright White | 7.0 | — |
| Canon Inks (No Additives) | | |
| HP Paper | 9.0 | 2.0 |
| 20% Thiosulfate | 2.4 | 0.1 |

EXAMPLE 37

Preparation of Heat Sealable Media Products Containing Colorant Stabilizer Additives This example describes the preparation of heat sealable media products containing colorant stabilizing additives of the present invention. In this example, the colorant stabilizing additive is a molecular includant, such as hydroxypropyl β-cyclodextrin. Heat sealable media products provide many uses. For example, such a media product can be constructed of a substrate layer such as paper, coated with at least one polymer containing the colorant stabilizing additive of the present invention. These media products can be used as an alternative to laminating products, in order to provide a lightfast and waterfast media product.

Additionally, such media products can be heat transfer products as described for example in U.S. Pat. No. 4,863,781, U.S. Pat. No. 5,242,739 and U.S. Pat. No. 5,501,902, which are hereby incorporated by reference. Generally, heat transfer products comprise a substrate layer, such as paper, coated with at least one polymer which releases a printable material upon the application of pressure and heat. Such heat transfer products are commonly used for melt printing designs on articles of clothing, for example. Additionally, heat transfer papers have been developed specifically for transferring graphics printed with an ink jet printer.

The thermoplastic polymers coating one or both sides of the substrate layer are typically selected from polyolefins, polyesters, ethylene-vinyl acetate copolymers or nylons. Additional components include humectants, ink viscosity modifiers, weak acids, surfactants, and binders, for example.

The present invention provides that from about 2% to 20% wt/wt molecular includant may be added to the coating polymer as a colorant stabilizing additive. The example below describes the production of two such media product coatings. The following ingredients were combined to make coating Formula A:

1) 217 parts water
2) 35 parts styrene maleic anhydride
3) 4.4 parts 28% solution ammonia in water
4) 88 parts 25% solution ethylene acrylic acid (available as MICAM PRIME from Michaelman Inc.)
5) 88 parts nylon copolymer 6/12, (available as ORGOSOL from Elf Atachem) having the formula
6) 88 parts polyvinyl alcohol
7) 38 parts 30% solution hydroxypropyl β-CD All ingredients were combined in a beaker, and blended with a mechanical stirrer into a smooth white paste. The paste was then milled for further consistency.

Suitable variations of the above formula will be apparent to those skilled in the art through routine experimentation. For example, in one alternative formulation, coating Formula B, elements 1–6 were combined in the same proportions, however, 456 parts 30% solution hydroxypropyl β-CD was used instead of 38 parts. As can be seen in the results below, the higher molecular includant content Formula B coating produced a more fade resistant media product. The results support a range of colorant stabilizer additive amounts.

The media coatings were then separately applied to a substrate, HP premium paper, by drawing down with a zero draw down bar. The wet coating was then dried in a vacuum oven to produce a coated media product. Ink B3, prepared as described below, was then printed onto the samples. The ink was fused to the media coating by briefly heating at about 300 degrees Fahrenheit for about 30 seconds.

When vinyl is used as an underlying coating layer, such as in a heat transfer product, the coating can be preferably adhered thereto by the addition of an intermediate coating layer, such as 50% wt of a polyvinyl acetate and silica, mill ground for consistency.

Printed sheets of media product from this example were placed in the Atlas weatherometer and exposed for the designated number of hours under the following conditions:

0.54 W/m² at 440 nm, 55% humidity, 45° C. black panel temperature, borosilicate filters.

The change in magenta color is measured by the Xrite Colorimeter (Model 938, SpectroDensitometer, Grandville, Mich.) which measures the ΔE* values, based on the L, a*, b* as described by Cielab, D-50-2. The results are reported in the tables below.

| B3 Ink | DI Water | 85.11% |
|---|---|---|
| | 2 Pyrrolidone | 10.00 |
| | Giv Guard DXN | 00.20 |
| | Cobratec 99 | 00.10 |
| | Triethanolamine | 00.50 |
| | Reactive Red 120 | 2.89 |
| | Acid Red 52 | 1.20 |

Fade Testing Results of Coated Media Products

| | 21 Hour | |
|---|---|---|
| Sample | ΔE* | ΔH* |
| B3 Ink on Formula A Coated Paper | 3.2 | −3.7 |
| B3 Ink on Formula B Coated Paper | 0.85 | 0.07 |
| B3 on Control Paper | 3.7 | 3.2 |

EXAMPLE 38

Preparation and Testing of Inks Containing Porphine Colorant Stabilizers

This example reports the results of fade testing of various inks, either with or without the stabilizing additives of the present invention, on treated or untreated paper. More particularly, the paper is untreated Hewlett-Packard premium paper, or treated Hewlett-Packard premium paper prepared using a solution of about 50% wt/wt hydroxypropyl γ-cyclodextrin to ink, in or on the paper in a concentration of about 5 to 15% wt/wt solution to paper.

The stabilizing additives of this example can be porphines. Specifically, the porphines Cu-meso-tetra-(4-sulfanatophenyl)-porphine (designated CuTPPS4) and Cu-meso-tetra-(N-methyl-4-pyridyl)-porphine (designated CuTMPS4) (available from Porphyrin Products, Inc., Logan, Utah) were used, which are represented by the following structures, respectively:

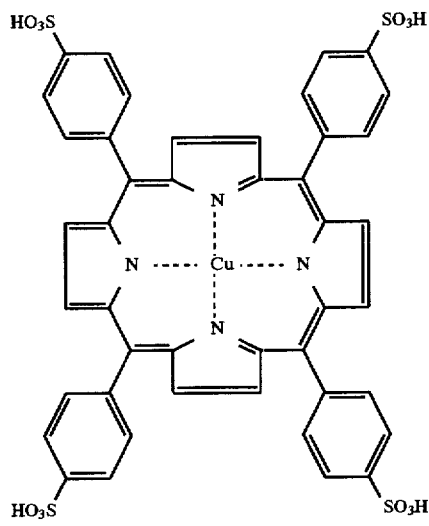

and

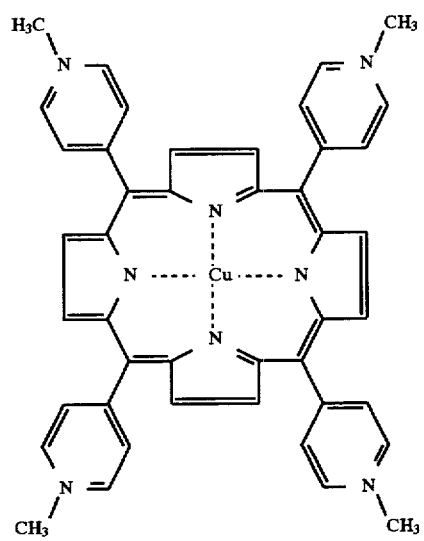

The invention provides that the metal ion Co or Cu may be used interchangeably in the porphine structures of the present invention. Additional background on the chemistry of porphines can be found in Kubat et al. "Photophysical properties of metal complexes of meso-tetrakis (4-sulphonatophenyl) Porphyrin," *Journal of Photochemistry and Photobiology A:Chemistry* 96 (1996) 93–97, and references cited therein, hereby incorporated by reference.

The stabilizing additive of this example can also optionally be dimethyl amino benzoic acid quat (designated DMABAQ), which can be produced as shown in the following reaction.

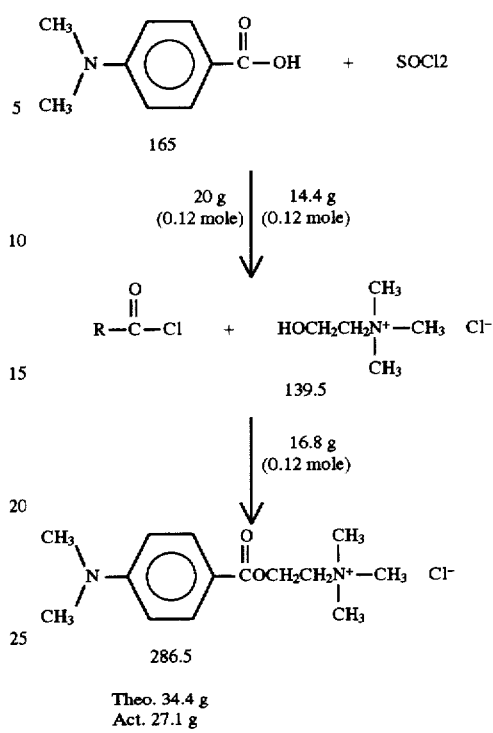

Theo. 34.4 g
Act. 27.1 g

Into a 3 necked 500 ml. round bottomed flask fitted with magnetic stirrer and condenser was added 20 g (0.12 moles) dimethyl amino benzoic acid (Aldrich) and 100 ml. of toluene. The Dean-Stark adapter was fitted and 80 ml. of toluene (Aldrich anhydrous grade) 14.4 g (0.12 mole) thionyl chloride added and the mixture heated at reflux for 2 hours. Toluene was then distilled off as more (100 ml.) was added. 16.8 g (0.12 mole) of choline chloride (Aldrich) dried in 50 ml. of toluene (Dean Stark) was added and the mixture refluxed overnight. The solution was then filtered hot and poured into a beaker chilled in an ice bath. The DMABAQ solid was then filtered and dried in a vacuum oven at 30° overnight.

Printed sheets of paper were placed in the Atlas weatherometer and exposed for the designated number of hours under the following conditions: 0.54 W/m$^2$ at 440 nm, 55% humidity, 45° C. black panel temperature, borosilicate filters.

The change in magenta color is measured by the Xrite Colorimeter (Model 938, SpectroDensitometer, Grandville, Mich.) which measures the $\Delta E^*$ values, based on the L, a*, b* as described by Cielab, D-50-2. The results are reported in the tables below.

The treated and untreated paper is printed with inks designated A1, A2, A3, A4, B1, B2, B3, B4, C1, C2, C3, and C4, prepared as follows:

| A1 Ink | DI Water | 84.80% |
|---|---|---|
| | 2 Pyrrolidone | 10.00 |
| | Giv Guard DXN | 00.20 |
| | Cobratec 99 | 00.10 |
| | Triethanolamine | 00.50 |
| | Reactive Red 120 | 4.00 |
| | Acid Red 52 | 0.40 |
| A2 Ink | DI Water | 85.40% |
| | 2 Pyrrolidone | 10.00 |

-continued

| | | |
|---|---|---|
| | Giv Guard DXN | 00.20 |
| | Cobratec 99 | 00.10 |
| | Triethanolamine | 00.50 |
| | Reactive Red 120 | 3.00 |
| | Acid Red 52 | 0.80 |
| A3 Ink | DI Water | 86.00% |
| | 2 Pyrrolidone | 10.00 |
| | Giv Guard DXN | 00.20 |
| | Cobratec 99 | 00.10 |
| | Triethanolamine | 00.50 |
| | Reactive Red 120 | 2.00 |
| | Acid Red 52 | 1.20 |
| A4 Ink | DI Water | 86.60% |
| | 2 Pyrrolidone | 10.00 |
| | Giv Guard DXN | 00.20 |
| | Cobratec 99 | 00.10 |
| | Triethanolamine | 00.50 |
| | Reactive Red 120 | 1.00 |
| | Acid Red 52 | 1.60 |
| B1 Ink | DI Water | 83.02% |
| | 2 Pyrrolidone | 10.00 |
| | Giv Guard DXN | 00.20 |
| | Cobratec 99 | 00.10 |
| | Triethanolamine | 00.50 |
| | Reactive Red 120 | 5.78 |
| | Acid Red 52 | 0.40 |
| B2 Ink | DI Water | 84.07% |
| | 2 Pyrrolidone | 10.00 |
| | Giv Guard DXN | 00.20 |
| | Cobratec 99 | 00.10 |
| | Triethanolamine | 00.50 |
| | Reactive Red 120 | 4.33 |
| | Acid Red 52 | 0.80 |
| B3 Ink | DI Water | 85.11% |
| | 2 Pyrrolidone | 10.00 |
| | Giv Guard DXN | 00.20 |
| | Cobratec 99 | 00.10 |
| | Triethanolamine | 00.50 |
| | Reactive Red 120 | 2.89 |
| | Acid Red 52 | 1.20 |
| B4 Ink | DI Water | 86.16% |
| | 2 Pyrrolidone | 10.00 |
| | Giv Guard DXN | 00.20 |
| | Cobratec 99 | 00.10 |
| | Triethanolamine | 00.50 |
| | Reactive Red 120 | 1.44 |
| | Acid Red 52 | 1.60 |
| C1 Ink | DI Water | 82.62% |
| | 2 Pyrrolidone | 10.00 |
| | Giv Guard DXN | 00.20 |
| | Cobratec 99 | 00.10 |
| | Triethanolamine | 00.50 |
| | Reactive Red 120 | 6.18 |
| | Acid Red 52 | 0.40 |
| C2 Ink | DI Water | 82.62% |
| | 2 Pyrrolidone | 10.00 |
| | Giv Guard DXN | 00.20 |
| | Cobratec 99 | 00.10 |
| | Triethanolamine | 00.50 |
| | Reactive Red 120 | 4.63 |
| | Acid Red 52 | 0.80 |
| C3 Ink | DI Water | 84.91% |
| | 2 Pyrrolidone | 10.00 |
| | Giv Guard DXN | 00.20 |
| | Cobratec 99 | 00.10 |
| | Triethanolamine | 00.50 |
| | Reactive Red 120 | 3.09 |
| | Acid Red 52 | 1.20 |
| C4 Ink | DI Water | 86.06% |
| | 2 Pyrrolidone | 10.00 |
| | Giv Guard DXN | 00.20 |
| | Cobratec 99 | 00.10 |
| | Triethanolamine | 00.50 |
| | Reactive Red 120 | 1.54 |
| | Acid Red 52 | 1.60 |

The above inks were fade tested with the following results.

| Inks Without Additives | | |
|---|---|---|
| | 63H | |
| Ink ID # | $\Delta E^*$ | $\Delta H^*$ |
| A1 | 47.8 | 7.5 |
| A2 | 57.5 | 21.6 |
| A3 | 60.7 | 33.8 |
| A4 | 62.1 | 43.2 |
| B1 | 38 | −0.54 |
| B2 | 46.4 | 14.8 |
| B3 | 56.3 | 28.4 |
| B4 | 64.7 | 39.1 |
| C1 | 69.4 | 2.6 |
| C2 | 64.3 | 11.3 |
| C3 | 72.4 | 20.5 |
| C4 | 83.9 | 22.7 |

The A2 ink was prepared with additives as described below and fade tested on HP paper and HP γ-CD paper with the following results.

| A2 Inks | | | | |
|---|---|---|---|---|
| | 15h | | 78h | |
| | $\Delta E^*$ | $\Delta H^*$ | $\Delta E^*$ | $\Delta H^*$ |
| HP Paper | | | | |
| 50% DMABAQ | 65.3 | 24.4 | | |
| 50% DMABAQ | 62.1 | 26.5 | 77.1 | 21.5 |
| 0.5% CuTPPS4 + 0.5% DMABAQ | 33.2 | 20.9 | 40.9 | 23.1 |
| 0.5% CuTPPS4 + 0.1% DMABAQ | 34.1 | 20.5 | 42.6 | 22.2 |
| HP γ-CD Paper | | | | |
| 50% DMABAQ | 4.1 | 2.4 | 4.9 | 2 |
| 50% DMABAQ | 6.3 | 4.5 | 7.7 | 5 |
| 0.5% CuTPPS4 + 0.5% DMABAQ | 4.2 | −2.1 | 5.2 | −2.5 |
| 0.5% CuTPPS4 + 0.1% DMABAQ | 3.5 | −0.34 | 5.4 | −3.1 |

The A3 ink was prepared with additives as described below and fade tested on HP paper and HP γ-CD paper with the following results.

| B3 Inks | | | | |
|---|---|---|---|---|
| | 15h | | 78h | |
| | $\Delta E^*$ | $\Delta H^*$ | $\Delta E^*$ | $\Delta H^*$ |
| HP Paper | | | | |
| 50% DMABAQ | 59.8 | 28.2 | 75.8 | 26.6 |
| 0.5% CuTPPS4 + 0.5% DMABAQ | 36.2 | 26.4 | 43.8 | 28.5 |
| 0.5% CuTPPS4 + 0.1% DMABAQ | 43.3 | 28.1 | 52.5 | 30.3 |
| HP γ-CD Paper | | | | |
| 50% DMABAQ | 6.1 | 4.9 | 7.6 | 5.5 |
| 50% DMABAQ | 10.4 | 8.4 | 12.4 | 9.7 |
| 0.5% CuTPPS4 + 0.5% DMABAQ | 6 | −2.9 | 7 | −3.2 |
| 0.5% CuTPPS4 + 0.1% DMABAQ | 4.1 | −0.69 | 6.1 | −2.1 |

The inks were prepared with about 0.5% $CuTPPS_4$ stabilizing additive and fade tested on HP paper and HP γ-CD paper with the following results.

| Inks made with 0.5% CuTPPS₄ on HP premium paper |||||||
|---|---|---|---|---|---|---|
| Samples | 15H || 78H || 94H ||
| ID # | ΔE* | ΔH* | ΔE* | ΔH* | ΔE* | ΔH* |
| A1 | 9.6 | 4.8 | 34.7 | 12.1 | 41.6 | 12.8 |
| A2 | 14.7 | 12.8 | 41.8 | 23.8 | 48.8 | 24.9 |
| A3 | 19.6 | 18.7 | 42.7 | 31.9 | 47 | 32.7 |
| A4 | 29.6 | 28.9 | 51.8 | 42.4 | 55.5 | 42.1 |
| B1 | 8.2 | 1.8 | 30.6 | 8.8 | 38.2 | 9.2 |
| B2 | 8.3 | 6.3 | 32.3 | 17.8 | 37.8 | 18.8 |
| B3 | 14.9 | 13.8 | 39.0 | 27.5 | 44.5 | 28.6 |
| B4 | 25.2 | 24.6 | 47.7 | 38.3 | 51.6 | 38.5 |
| C1 | 14.3 | -7.71 | 41.8 | 8.9 | N/A | N/A |
| C2 | 7.9 | -2.7 | 33.7 | 13.9 | N/A | N/A |
| C3 | 9.2 | 6.9 | 37.9 | 23.6 | N/A | N/A |
| C4 | 23.1 | 22.2 | 48.6 | 37.7 | N/A | N/A |

| Inks with 0.5% CuTPPS₄ on Hydroxy-Propyl γ-CD paper |||||||
|---|---|---|---|---|---|---|
| Samples | 15H || 78H || 94H ||
| ID # | ΔE* | ΔH* | ΔE* | ΔH* | ΔE* | ΔH* |
| A1 | 1.5 | -0.2 | 6.6 | -3.2 | 8 | -4.1 |
| A2 | 1.2 | 0.28 | 4.1 | -0.8 | 5.4 | -1.3 |
| A3 | 2.8 | 2.14 | 5 | 4.3 | 5.2 | 4.3 |
| A4 | 4.9 | 4.7 | 10.4 | 9.8 | 10.2 | 9.5 |
| B1 | 3.1 | -1.5 | 9.4 | -5.5 | 11.2 | -6.9 |
| B2 | 2.3 | -2.4 | 7.7 | -5.2 | 8.3 | -5.7 |
| B3 | 1.2 | 1.1 | 4.1 | 0.13 | 4.7 | -0.79 |
| B4 | 2.9 | 2.6 | 7.2 | 6.3 | 7.7 | 6.5 |
| C1 | 4 | -3.3 | 17.1 | -13.8 | N/A | N/A |
| C2 | 3 | -2.6 | 3.4 | -2.8 | N/A | N/A |
| C3 | 1.6 | -1.5 | 5.2 | -3.3 | N/A | N/A |
| C4 | 1.4 | 1.1 | 4.7 | 3.5 | N/A | N/A |

Additionally, HP-1600 magenta ink was prepared with about 0.5% CuTPPS₄ stabilizing additive and fade tested on HP paper and HP γ-CD paper with the following results.

| 15 Hour Multiple Samples |||
|---|---|---|
| Samples ID # | ΔE* | ΔH* |
| HP #1 | 14.68 | 13.13 |
| HP #2 | 20.86 | 19.50 |
| HP #3 | 17.01 | 15.55 |
| HP #4 | 13.04 | 11.15 |
| HP #5 | 13.11 | 10.57 |
| HP #6 | 13.09 | 11.10 |
| HP γ-CD #1 | 2.66 | -1.47 |
| HP γ-CD #2 | 1.20 | -.53 |
| HP γ-CD #3 | 2.44 | -.53 |
| HP γ-CD #4 | 1.30 | -.47 |
| HP γ-CD #5 | 1.74 | -.30 |
| HP γ-CD #6 | 1.35 | -.34 |

The HP-1600 magenta ink was also prepared with about 0.5% CuTMPS₄ stabilizing additive and fade tested on HP paper and HP γ-CD paper with the following results.

| 15 Hour Multiple Samples |||
|---|---|---|
| HP #1 | 13.94 | 11.39 |
| HP #2 | 13.58 | 11.11 |
| HP #3 | 13.98 | 11.57 |
| HP #4 | 14.16 | 11.56 |
| HP γ-CD #1 | 2.32 | -.99 |
| HP γ-CD #2 | 1.44 | -1.05 |
| HP γ-CD #3 | 2.17 | -.67 |
| HP γ-CD #4 | 1.98 | -1.21 |
| HP γ-CD #5 | 2.14 | -1.38 |
| HP γ-CD #6 | 1.79 | -.85 |
| HP γ-CD #7 | .36 | .15 |

EXAMPLE 39

Preparation of Basic Fuschin Hydrazone

Another colorant stabilizer of the present invention is a basic fuschin hydrazone, prepared as follows. To a 500 ml round bottom flask, fitted with a magnetic stirrer and a heating mantle, was placed 50 g (0.46 mole) phenyl hydrazine (Aldrich), 96.3 g (0.46 mole) chalcone (Aldrich), and 300 ml. of anhydrous ethanol. The reaction mixture refluxed overnight and then cooled to room temperature. A white precipitate formed and was filtered to yield a white solid which was washed with cold ether. 128 g (93%) chalcone hydrazone was obtained. This reaction is shown below.

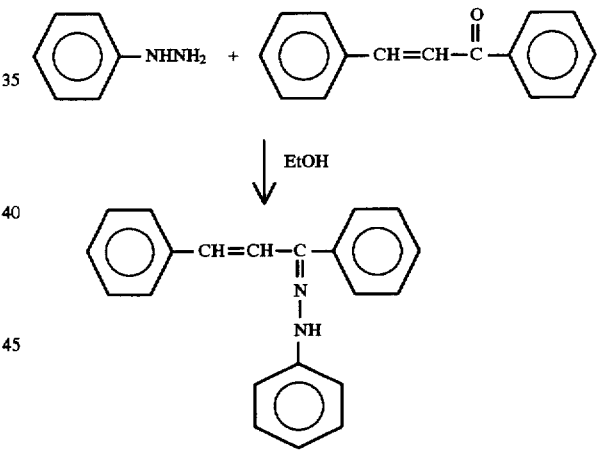

To a 500 ml three necked flask fitted with a condenser, Argon bubbles and a magnetic stirrer, was placed 20 g (0.09 mole) 4,4'-diamino benzophenone (Aldrich), 27.1 g (0.09 mole) chalcone hydrazone (produced above), 10.1 g phosphorous oxy chloride (Aldrich) and 200 ml of dried dioxane. The mixture was refluxed for two days to yield a red solution. The reaction mixture was chilled in an ice bath and the red precipitate filtered to yield 35.2 g (78%). Addition of hexane to the solution generated an extra 3 g The compound was purified by neutralization from 3% ethanol in 97.1% chloroform. It was also run down a column (silica gel) with 1% ethanol in $CHCl_3$ to elute impurities, then the product was eluted with 10% ethanol in chloroform. This reaction is shown below.

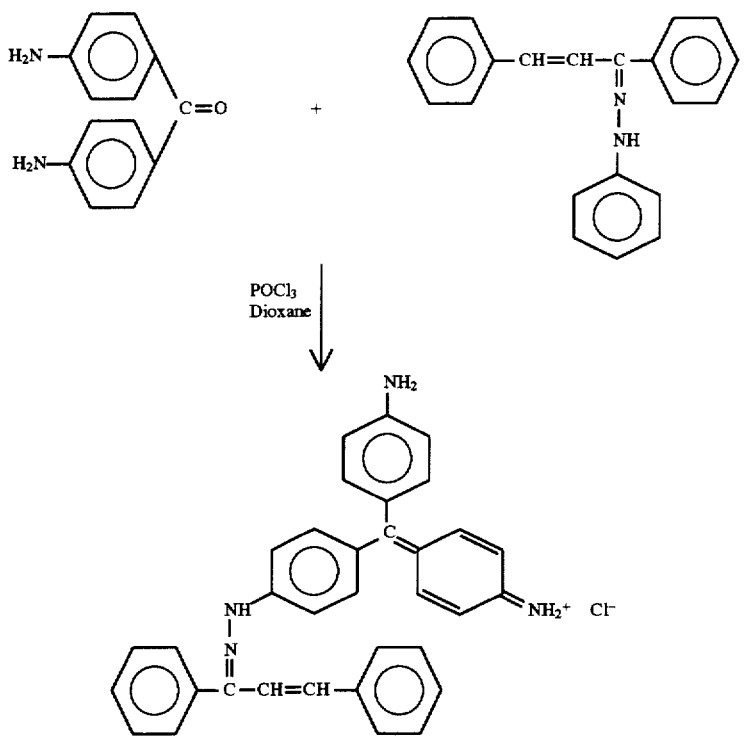

EXAMPLE 40

Preparation and Testing of Inks on Paper Containing Benzophenone Colorant Stabilizer Additives This example reports the results of fade testing of magenta ink jet inks on Hewlett-Packard premium paper containing another stabilizing additives of the present invention. In particular, the additive of this example is a benzophenone, of the general formula:

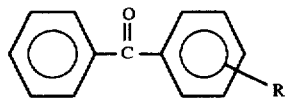

wherein R represents any substituents which permit the benzophenone to function as a colorant stabilizer.

More specifically, in this example the benzophenone derivative is 2-hydroxy-4-methoxy-benzophenone-5-sulfonic acid (designated HMBPD, or simply U) (available from Lancaster Synthesis Ltd., Windham, N.H.), represented by the following structure:

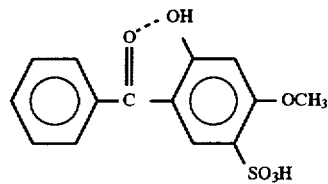

In addition, the colorant stabilizing additive can be a molecular includant, such as a cyclodextrin. The paper containing the additives was prepared as follows:

Pre-complexation of Additive U with β-CD 5.0 g (0.02 mole) of 2-hydroxy-4-methoxy-benzophenone-5-sulfonic acid (additive U), 27.2 g (0.02 mole) β-cyclodextrin and 136 ml water was placed in a beaker and stirred on a hot-plate stirrer. The suspension was heated to 65° C. at which point the mixture became a clear solution.

Paper Coating Solution 0.7 ml of SURFYNOL 420 surfactant and 30.0 g (0.02 mole) γ-CD was then added to the above solution and stirred while maintaining 65° C. The heated clear solution was used to coat the HP Premium ink jet paper. The surface tension of the heated solution was 48–52 dyne/cm.

Coating Papers Procedure

Pre-weighed Hewlett-Packard Premium ink jet paper #51634Y was placed on a stack of 20 sheets of NEENAH BOND® paper and a draw-down bar placed at the top of the paper. Using a Pasteur pipette, the hot additives solutions were placed on the paper at the edge of the draw-down bar. The draw-down bar was then drawn-down on the paper sheet with light pressure to yield a wet film. The paper was then placed in a vacuum oven and dried under 0.1 mm Hg vacuum at 35° C. for 20 minutes. The dried paper was re-weighed and the add-on calculated. The sheets were then used directly for printing.

| Wire Draw Down Bar # | Approx. Add-on % |
| --- | --- |
| 0 | 3–5 |
| 12 | 5–8 |
| 24 | 9–20 |

For testing, an Atlas Ci35 weatherometer controlled irradiance exposure system was used which provides high intensity daylight simulation with xenon source set at an average temperature of 63° C., an irradiance of 1.10 W/m$^2$/nm (at 420 nm), and a humidity of 30% in an industry standard test environment (ASTM G-26 Method 3).

Color measurement was determined by an X-Rite 938 Spectrodensitometer measurement and storage of full spectral curves. Three measurements of each sample with averaging were performed with automatic calculation of CIELAB values. CIELAB calculated for D-50 standard lighting conditions. The results are reported in the table below.

|  | 70 h | |
| --- | --- | --- |
|  | ΔE* | ΔH* |
| HP 1600 on HP Control | 70 | 7 |
| HP 1600 on HP with β-CD (14.0%) | 30 | 8 |
| HP 1600 on HP with γ-CD (5.5%) | 30 | 4 |
| HP 855 on HP Control | 26 | 8 |
| HP 855 on HP with β-CD | 14 | 4 |
| HP 855 on HP with γ-CD (5.5%) | 9 | 4 |

Additional tests yielded the following results.

|  | 15 h | | 30h | | 70h | | 115h | | 200h | |
| --- | --- | --- | --- | --- | --- | --- | --- | --- | --- | --- |
|  | ΔE* | ΔH* | ΔE* | ΔH* | ΔE* | ΔH* | ΔE* | ΔH* | ΔE* | ΔH* |
| HP 1600 on HP (Control) | 20 | 13 | — | — | 70 | 7 | color-less | color-less | color-less | color-less |
| HP 1600 on HP with Additive U with β and γ CD) | 5 | 3 | 5 | 3 | 11 | 5 | 13 | 5 | 21 | 6 |
| HP 855 on HP (Control) | 10 | 9 | — | — | 26 | 8 | 39 | 8 | 57 | 8 |
| HP 855 on HP with Additive U with β and γ CD) | 4 | 3 | 4 | 3 | 4 | 3 | 6 | 3 | 10 | 3 |

Additional tests yielded the following results.

Accelerated Fade Study of HP1600 on Coated Paper

|  | 15h | | 70h | |
| --- | --- | --- | --- | --- |
|  | ΔE* | ΔH* | ΔE* | ΔH* |
| HP Control | 20 | 13 | 70 | 7 |
| β-CD (9.2%) | 18 | 13 | 42 | 10 |
| β-CD (14.0%) | 14 | 11 | 30 | 8 |
| *HMPBS (3.1%) | — | — | 30 | 19 |
| *HMPBS (5.1%) | — | — | 33 | 21 |
| *HMPBS (8.6%) | — | — | 27 | 11 |
| *HMPBS + β-CD (5.7%) | — | — | 28 | 11 |
| *HMPBS + γ-CD (5.7%) | — | — | 29 | 16 |
| γ-CD (5.5%) | — | — | 30 | 4 |
| γ-CD (10%) | 8 | 7 | 29 | 5 |
| *HMPBS + β + γ (4.0%) (No precomplexation) | — | — | 37 | 16 |
| *HMPBS + β + γ (9.0%) (No precomplexation) | 5 | 3 | 7 | 4 |
| β-CD + γ-CD (15.0%) | 18 | 11 | 29 | 10 |

( ) Dry add-on wt. wt on the sheet
*Additive U
— Data point not taken

Additional tests yielded the following results.

Accelerated Fade Study of HP855 on Coated Papers

|  | 15h | | 70h | |
| --- | --- | --- | --- | --- |
|  | ΔE* | ΔH* | ΔE* | ΔH* |
| HP Control | 10 | 9 | 26 | 18 |
| β-CD (3.8%) | — | — | 10 | 4 |
| β-CD (8.7%) | 7 | 5 | 14 | 4 |
| β-CD (13.0%) | 6 | 5 | 14 | 10 |
| *HMBPS (2.8%) | — | — | 14 | 10 |
| *HMBPS (3.8%) | — | — | 13 | 10 |
| *HMBPS (4.6%) | — | — | 11 | 9 |
| γ-CD (5.5%) | — | — | 9 | 4 |
| γ-CD (10.5%) | 8 | 6 | 18 | 6 |
| *HMBPS + β + γ (3.0%) (No precomplexation) | — | — | 20 | 13 |
| *HMBPS + β + γ (8.1%) (No precomplexation) | 5 | 4 | 5 | 4 |
| *HMBPS + β + γ (8.1%) (repeat) (No precomplexation) | — | — | 4 | 4 |
| β + γ (15%) | 6 | 4 | 18 | 4 |

( ) Dry add-on wt. wt on the sheet
*Additive U
— Data point not taken

The results suggest that pre-complexation of Additive U with β-CD gives superior results than when added separately. Pre-complexation of Additive U with β-CD followed by mixing with γ-CD gives maximally superior results. Additive U when coated on HP paper without cyclodextrin provides some improvement. γ-CD and β-CD applied separately and together provides some improvement in lightfastness.

Having thus described the invention, numerous changes and modifications hereof will be readily apparent to those having ordinary skill in the art, without departing from the spirit or scope of the invention.

What is claimed is:

1. A composition comprising a colorant and a stabilizing agent, wherein the stabilizing agent is a porphine.

2. The composition of claim 1, wherein the porphine is Cu-meso-tetra-(4-sulfanatophenyl)-porphine or Cu-mesotetra-(N-methyl-4-pyridyl)-porphine, having the following structures, respectively:
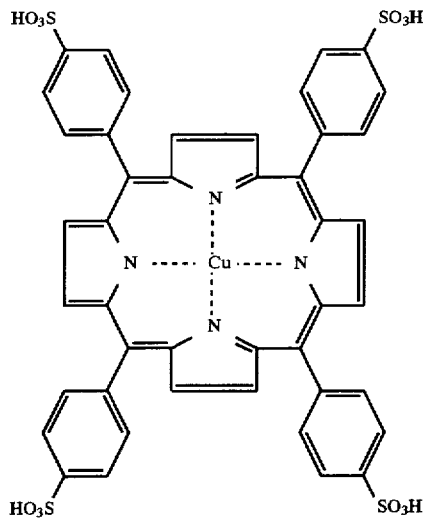
or
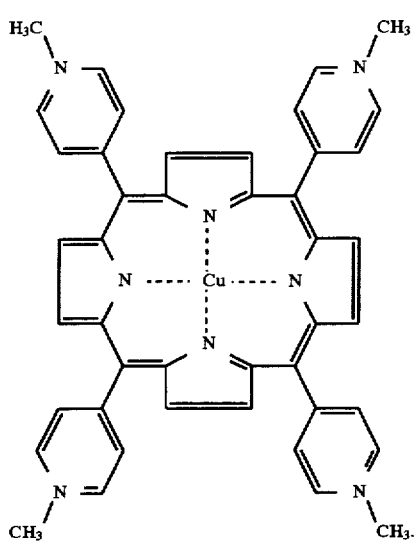
3. The composition of claim 1, wherein the porphine is Co-meso-tetra-(4-sulfanatophenyl)-porphine or Co-meso-
tetra-(N-methyl-4-pyridyl)-porphine, having the following structures, respectively:
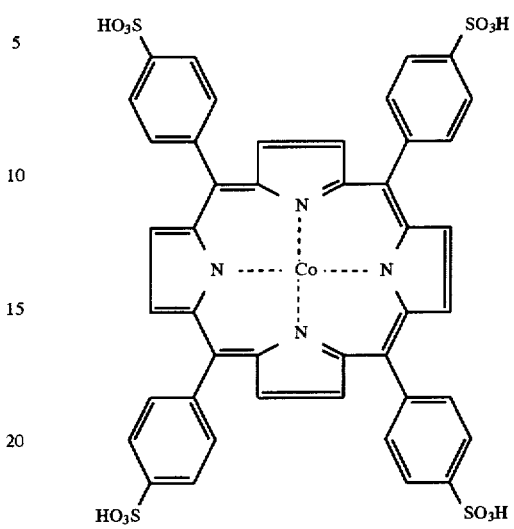
or
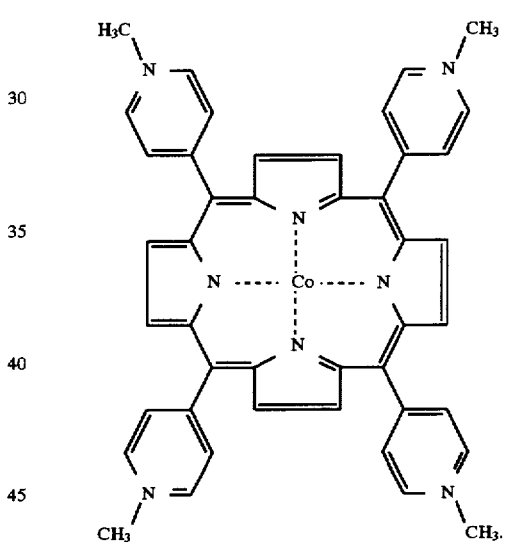

4. The composition of claim 2, wherein the porphine is Cu-meso-tetra-(4-sulfanatophenyl)-porphine having the following structure:

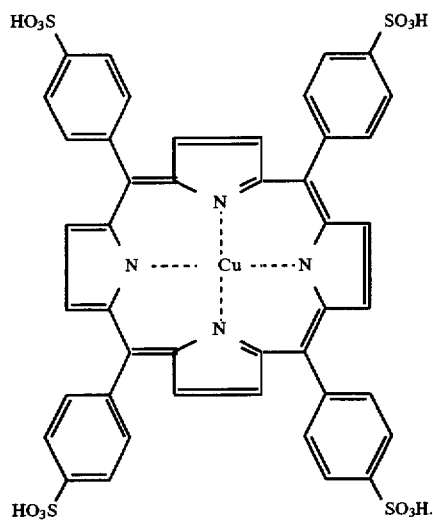

5. The composition of claim 2, wherein the porphine is Cu-meso-tetra-(N-methyl4-pyridyl)-porphine having the following structure:

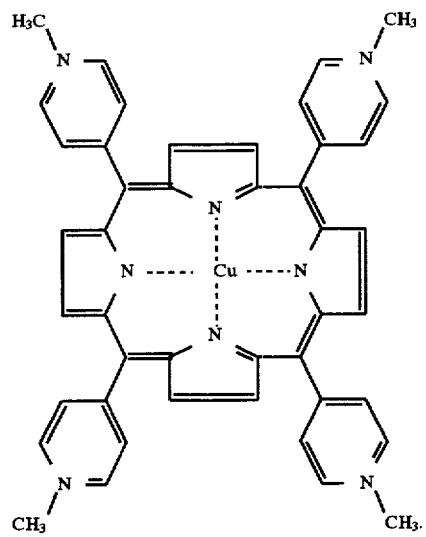

6. The composition of claim 1, wherein the porphine is a sodium salt of Cu-meso-tetra-(4-sulfanatophenyl)-porphine having the following structure:

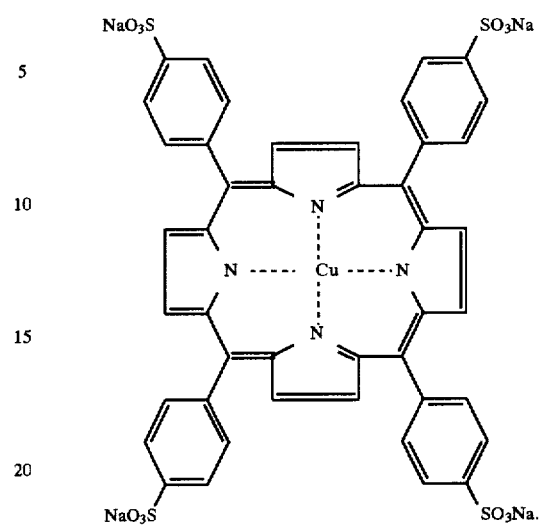

7. The composition of claim 3, wherein the porphine is Co-meso-tetra-(4-sulfanatophenyl)-porphine having the following structure:

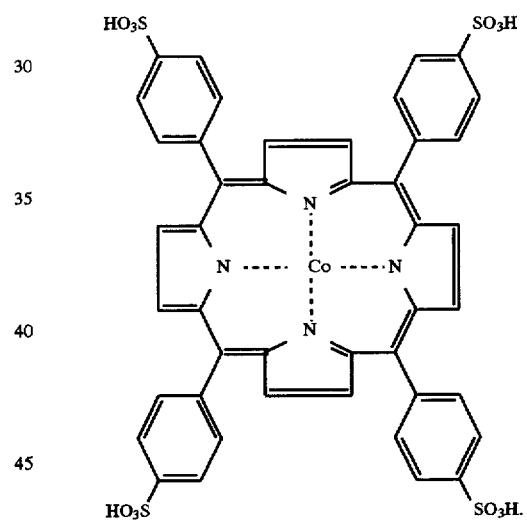

8. The composition of claim 3, wherein the porphine is Co-meso-tetra-(N-methyl-4-pyridyl)-porphine having the following structure:

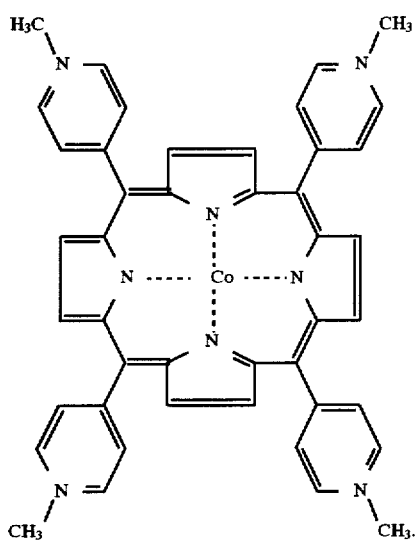

9. The composition of claim 1, wherein the porphine is a sodium salt of Co-meso-tetra-(4-sulfanatophenyl)-porphine having the following structure:

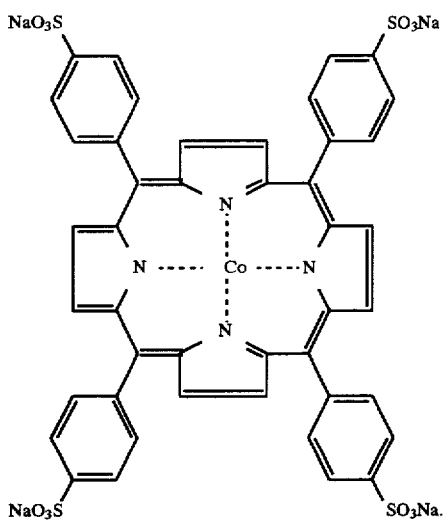

10. The composition of claim 1, further comprising a molecular includant.

11. A composition comprising a colorant and a stabilizing agent, wherein the stabilizing agent is dimethyl amino benzoic acid quat, represented by the following structure:

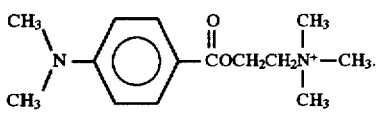

12. The composition of claim 11, further comprising a molecular includant.

13. A composition comprising a colorant and a stabilizing agent, wherein the stabilizing agent is a basic fuschin hydrazone, represented by the following structure:

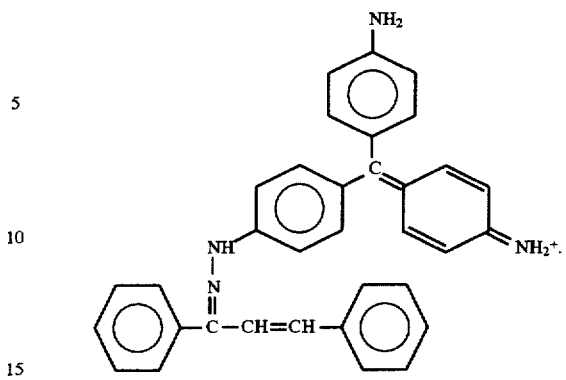

14. A composition comprising a colorant, a molecular includant, and a stabilizing agent, wherein the stabilizing agent is a benzophenone of the general formula:

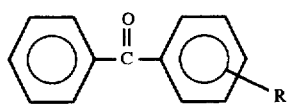

wherein R represents one or more substituents selected from the group consisting of hydroxyl groups, alkyl ether groups and sulfonic acid groups.

15. The composition of claim 14, wherein the benzophenone is 2-hydroxy-4-methoxy-benzophenone-5-sulfonic acid, represented by the following structure:

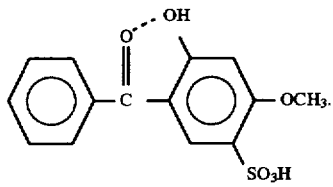

16. The composition of claim 15, wherein the molecular includant is a clathrate, intercalate, zeolite, crown ether, calixarene, valinomycin natural antibiotic, nigericin natural antibiotic, or cyclic compound containing a plurality of pyranose rings.

17. The composition of claim 16, wherein the cyclic compound is α-cyclodextrin, β-cyclodextrin, γ-cyclodextrin, δ-cyclodextrin, hydroxypropyl β-cyclodextrin, hydroxyethyl β-cyclodextrin, hydroxyethyl α-cyclodextrin, carboxymethyl α-cyclodextrin, carboxymethyl β-cyclodextrin, carboxymethyl γ-cyclodextrin, octyl succinated α-cyclodextrin, octyl succinated β-cyclodextrin, octyl succinated γ-cyclodextrin, sulfated β-cyclodextrin, sulfated γ-cyclodextrin, hydroxyethyl γ-cyclodextrin, hydroxyisopropyl γ-yclodextrin, or hydroxypropyl γ-cyclodextrin.

18. A method of light-stabilizing a colorant composition, comprising associating a colorant composition with a porphine.

19. The method of claim 18, wherein the porphine is Cu-meso-tetra-(4-sulfanatophenyl)-porphine or Cu-meso-tetra-(N-methyl-4-pyridyl)-porphine, having the following structures, respectively:

71
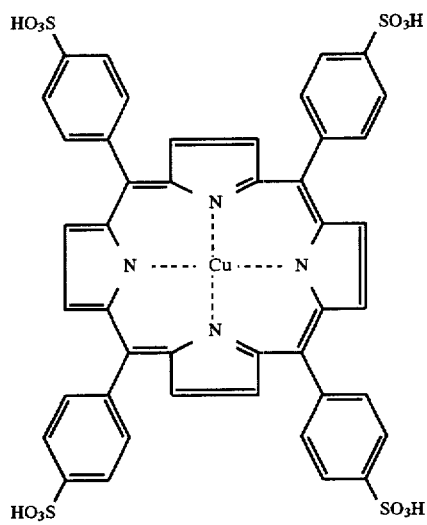
or
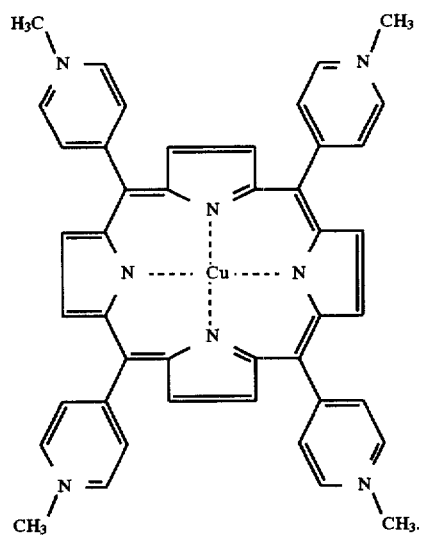
20. The method of claim 16, wherein the porphine is Co-meso-tetra-(4-sulfanatophenyl)-porphine or Co-meso-tetra-(N-methyl-4-pyridyl)-porphine, having the following structures, respectively:
72
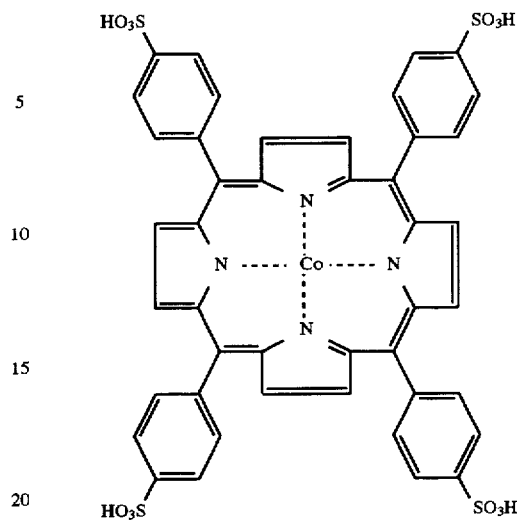
or
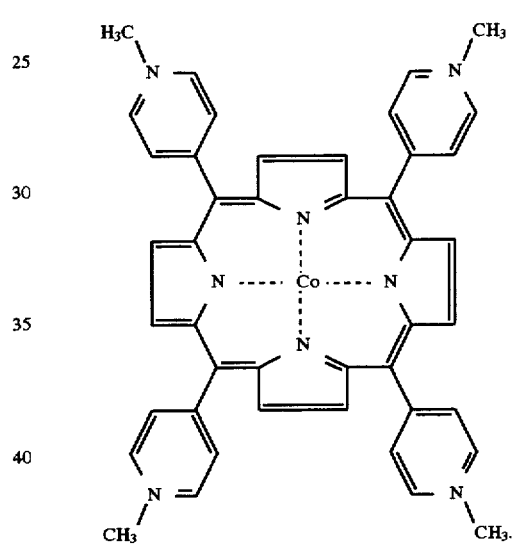
21. The method of claim 19, wherein the porphine is Cu-meso-tetra-(4-sulfanatophenyl)-porphine having the following structure:

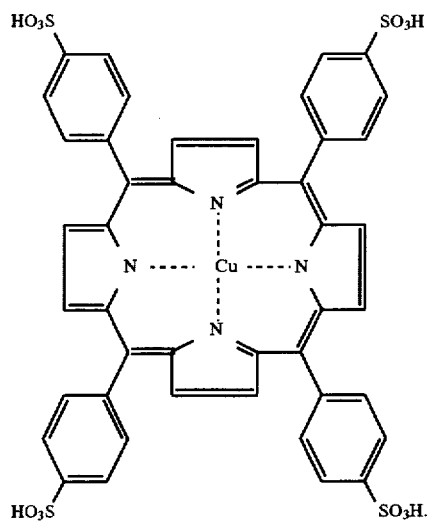

22. The method of claim 19, wherein the porphine is Cu-meso-tetra-(N-metyl-4-pyridyl)-porphine having the following structure:

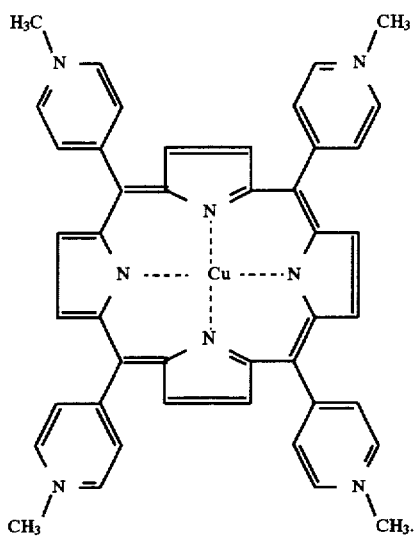

23. The method of claim 18, wherein the porphine is a sodium salt of Cu-meso-tetra-(4 sulfanatophenyl)-porphine having the following structure:

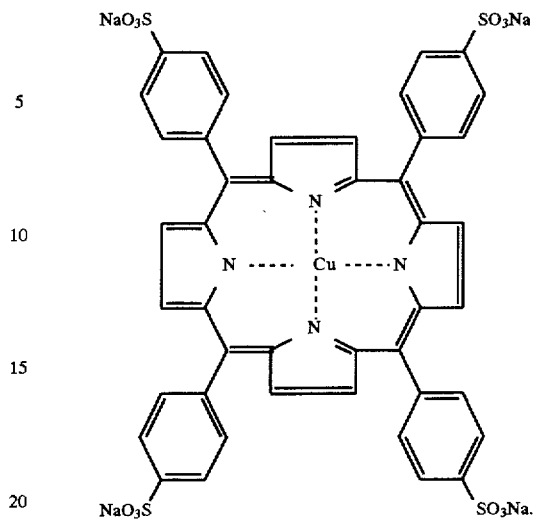

24. The method of claim 20, wherein the porphine is Co-meso-tetra-(4-sulfanatophenyl)-porphine having the following structure:

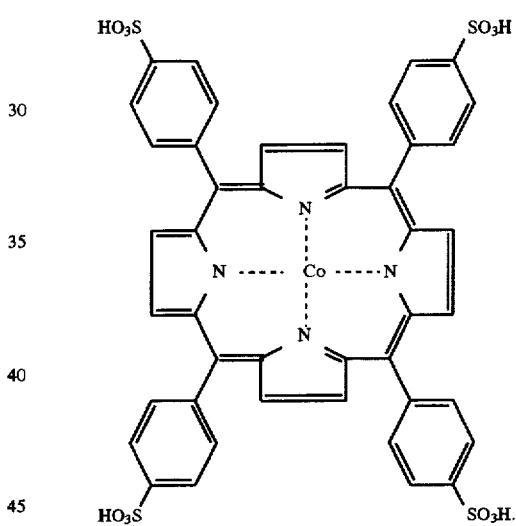

25. The method of claim 20, wherein the porphine is Co-meso-tetra-(N-methyl-4-pyridyl)-porphine having the following structure:

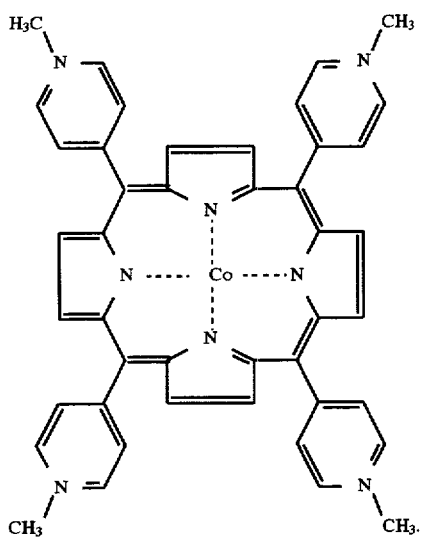

26. The method of claim 18, wherein the porphine is a sodium salt of Co-meso-tetra-(4-sulfanatophenyl)-porphine having the following structure:

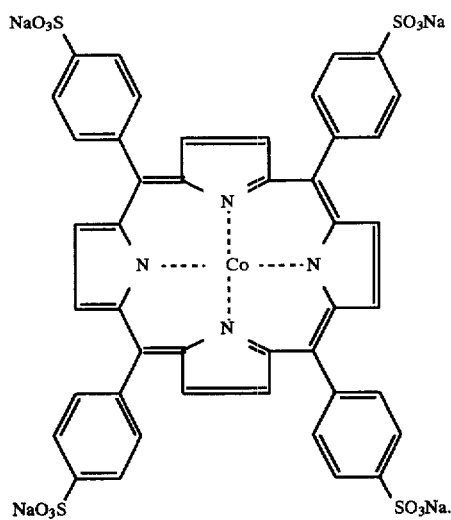

27. The method of claim 18, further comprising associating a molecular includant with the colorant composition and the porphine.

28. A method of light-stabilizing a colorant composition, comprising associating a colorant composition with a basic fuschin hydrazone represented by the following structure:

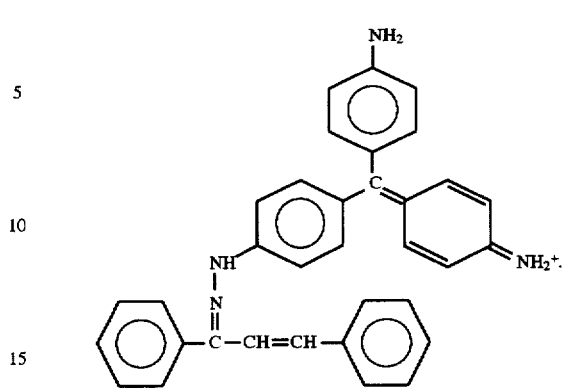

29. A method of light-stabilizing a colorant composition, comprising associating a colorant composition with a molecular includant and a benzophenone of the general formula:

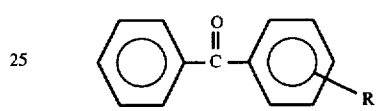

wherein R represents one or more substituents selected from the group consisting of hydroxyl groups, alkyl ether groups and sulfonic acid groups.

30. The method of claim 29, wherein the benzophenone is 2-hydroxy-4-methoxy-benzophenone-5-sulfonic acid, represented by the following structure:

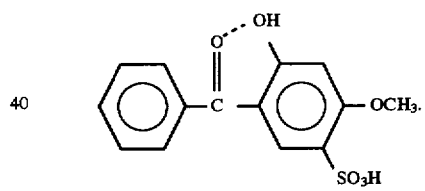

31. A composition comprising a colorant and a stabilizing agent, wherein the stabilizing agent is Cu-meso-tetra-(4-sulfanatophenyl)-porphine, a sodium salt of Cu-meso-tetra-(4-sulfanatophenyl)-porphine or Cu-meso-tetra-(N-methyl-4-pyridyl)-porphine, having the following structures, respectively:

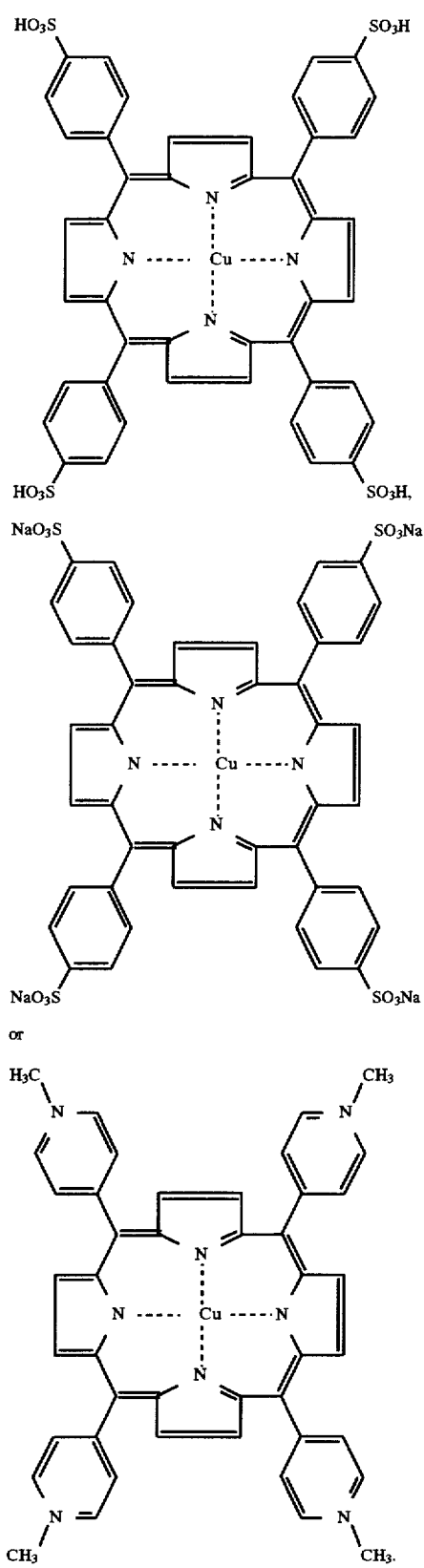
32. A composition comprising a colorant and a stabilizing agent, wherein the stabilizing agent is Co-meso-tetra-(4-sulfanatophenyl)-porphine, a sodium salt of Co-meso-tetra-(4-sulfanatophenyl)-porphine or Co-meso-tetra-(N-methyl-4-pyridyl)-porphine, having the following structures, respectively:
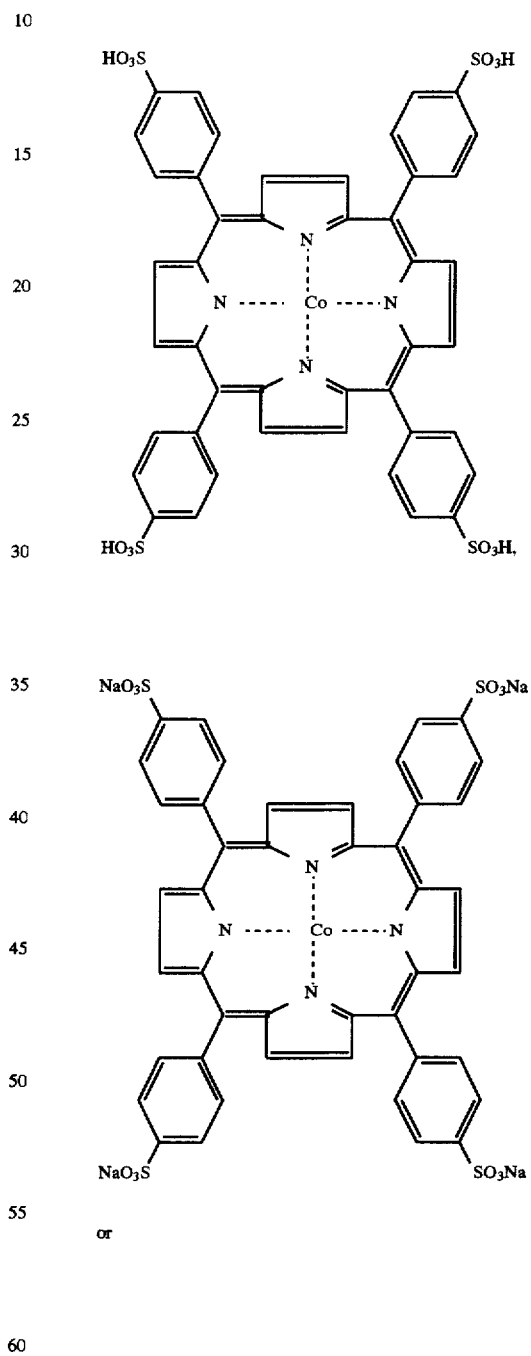
or

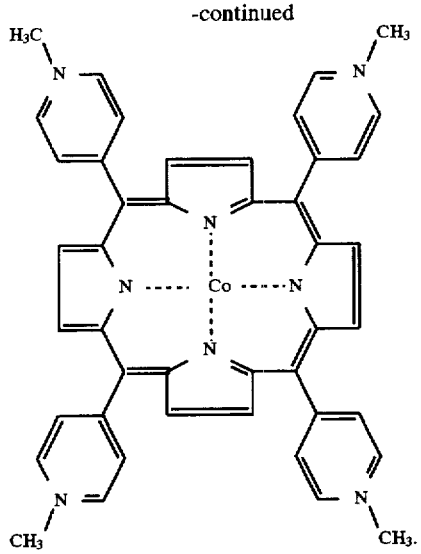

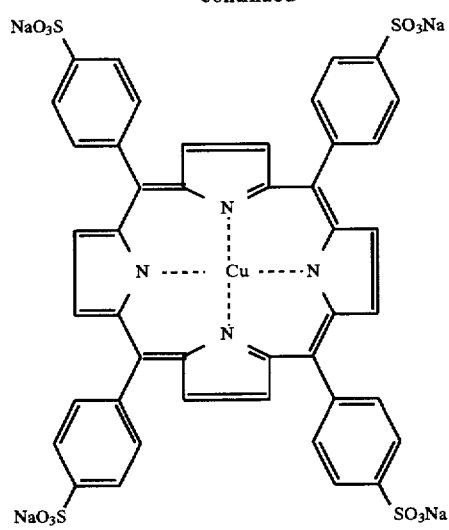

33. A composition comprising a colorant, a molecular includant and a stabilizing agent, wherein the stabilizing agent is a porphine.

34. A method of light-stabilizing a colorant composition, the method comprising:

associating a colorant composition with Cu-meso-tetra-(4-sulfanatophenyl)-porphine, a sodium salt of Cu-meso-tetra-(4-sulfanatophenyl)-porphine or Cu-meso-tetra-(N-methyl-4-pyridyl)-porphine, having the following structures, respectively:

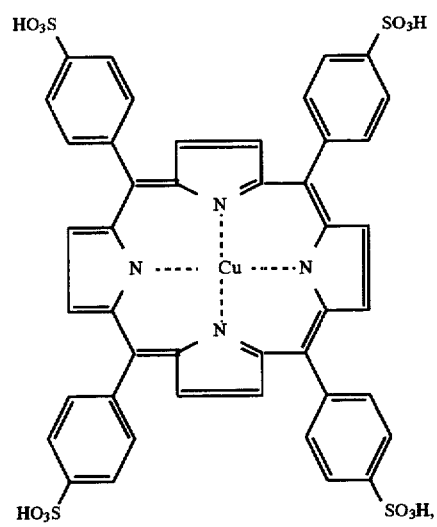

or

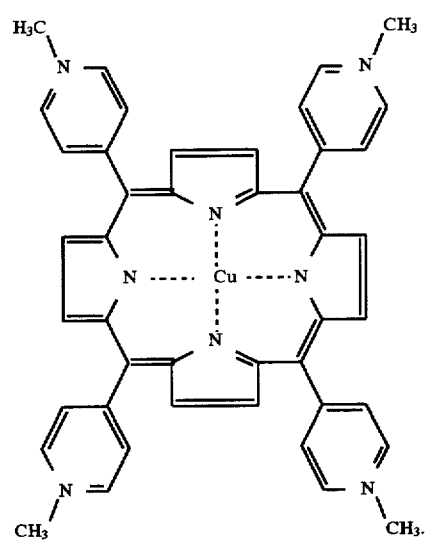

35. A method of light-stabilizing a colorant composition, the method comprising:

associating a colorant composition with Co-meso-tetra-(4-sulfanatophenyl)-porphine, a sodium salt of Co-meso-tetra-(4-sulfanatophenyl)-porphine or Co-meso-tetra-(N-methyl-4-pyridyl)-porphine, having the following structures, respectively:

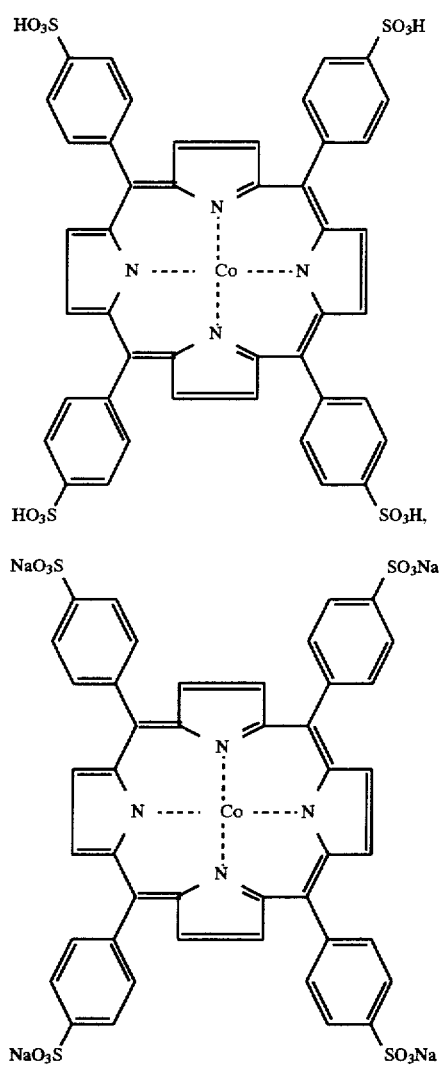
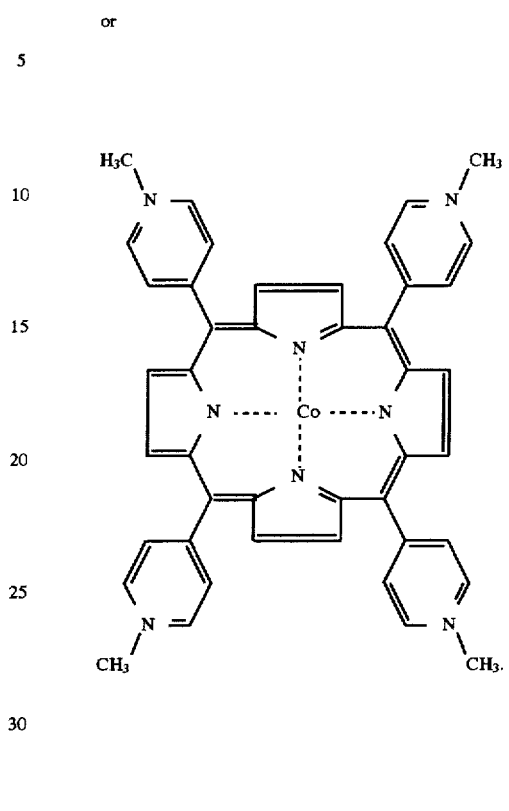
36. A method of light-stabilizing a colorant composition, the method comprising:
associating a colorant composition with a molecular includant and a porphine.
* * * * *